(12) United States Patent
van Kilsdonk et al.

(10) Patent No.: US 11,985,960 B2
(45) Date of Patent: *May 21, 2024

(54) LIVE INSECTS TRANSPORT DEVICE

(71) Applicant: Protix B.V., Dongen (NL)

(72) Inventors: Jaap van Kilsdonk, Veldhoven (NL);
Eric Holland Schmitt, Antwerp (BE);
Ralf Henricus Wilhelmina Jacobs,
Eindhoven (NL); **Henricus Petrus
Johannes Simons**, Den Bosch (NL);
Maurits Petrus Maria Jansen, Bavel
(NL); Ward Tollenaar, Dongen (NL)

(73) Assignee: Protix B.V., Dongen (NL)

( * ) Notice: Subject to any disclaimer, the term of this patent is extended or adjusted under 35 U.S.C. 154(b) by 234 days.

This patent is subject to a terminal disclaimer.

(21) Appl. No.: 17/615,590

(22) PCT Filed: May 20, 2020

(86) PCT No.: PCT/NL2020/050321
§ 371 (c)(1),
(2) Date: Dec. 1, 2021

(87) PCT Pub. No.: WO2020/246873
PCT Pub. Date: Dec. 10, 2020

(65) Prior Publication Data
US 2022/0304287 A1   Sep. 29, 2022

Related U.S. Application Data

(60) Provisional application No. 62/857,842, filed on Jun. 6, 2019.

(30) Foreign Application Priority Data

Jun. 14, 2019 (NL) .................................. 2023315
Nov. 21, 2019 (WO) ................ PCT/NL2019/050767

(51) Int. Cl.
*A01K 67/033* (2006.01)
*B04C 5/18* (2006.01)

(52) U.S. Cl.
CPC .............. *A01K 67/033* (2013.01); *B04C 5/18* (2013.01)

(58) Field of Classification Search
CPC ......... A01K 67/033; A01K 1/004; B04C 5/15
(Continued)

(56) References Cited

U.S. PATENT DOCUMENTS 3,223,237 A   12/1965   Harrod et al.
3,893,420 A    7/1975   Vasilievich et al.
(Continued)

FOREIGN PATENT DOCUMENTS

CN   104285913 A   *  1/2015   ........... A01K 67/033
NL      2020153 B1      7/2019
(Continued)

*Primary Examiner* — Timothy D Collins
*Assistant Examiner* — Maria E Graber
(74) *Attorney, Agent, or Firm* — N.V. Nederlandsch Octrooibureau

(57) ABSTRACT

The invention relates to a device for use in large-scale industrial insect farming. More in particular, the invention relates to an insects transport device for transporting live insects from a first location to a predetermined second location, the insects transport device comprising a gas guiding unit, a gas discharge member and a feeder arrangement, wherein the insects transport device is configured to receive live insects such as freshly hatched neonate larvae, for example of black soldier fly, or mites, wherein the live insects are directly taken up in a laminar flow of gas after exiting the feeder arrangement in a free fall under influence of gravitation such that the live insects do not contact any surface of the insects transport device, and while in said gas are transported to a predetermined location in the insects transport device. Furthermore, the invention relates to the use of the device in industrial insect farming, such as large-scale farming of black soldier flies or mites. The invention also relates to a method of dosing live insects, wherein for example live insects are dosed which are essentially of the same age (e.g. within an age difference of 1 second-5 minutes), such as freshly hatched neonate larvae. In addition, the invention relates to a single dose of neonate larvae obtained with the method, wherein larvae have a small larvae-to-larvae age difference within the single dose.

20 Claims, 30 Drawing Sheets

(58) Field of Classification Search
USPC .......................................................... 119/6.5
See application file for complete search history.

(56) References Cited

U.S. PATENT DOCUMENTS

| | | | |
|---|---|---|---|
| 5,594,654 A | 1/1997 | Shuman et al. | |
| 5,927,004 A | 7/1999 | Stocker | |
| 10,051,845 B1 * | 8/2018 | Massaro | A01K 29/005 |
| 10,058,080 B2 * | 8/2018 | Leo | A23K 20/20 |
| 2011/0139075 A1 * | 6/2011 | Shapiro | A01K 67/033 |
| | | | 119/6.5 |
| 2018/0049414 A1 | 2/2018 | Leo | |

FOREIGN PATENT DOCUMENTS

| | | | | |
|---|---|---|---|---|
| RU | 2336696 C1 * | 10/2008 | | A01K 67/033 |
| RU | 2336696 C1 | 10/2008 | | |
| WO | 2019125162 A1 | 6/2019 | | |
| WO | WO-2021007541 A1 * | 1/2021 | | A01K 29/00 |

* cited by examiner

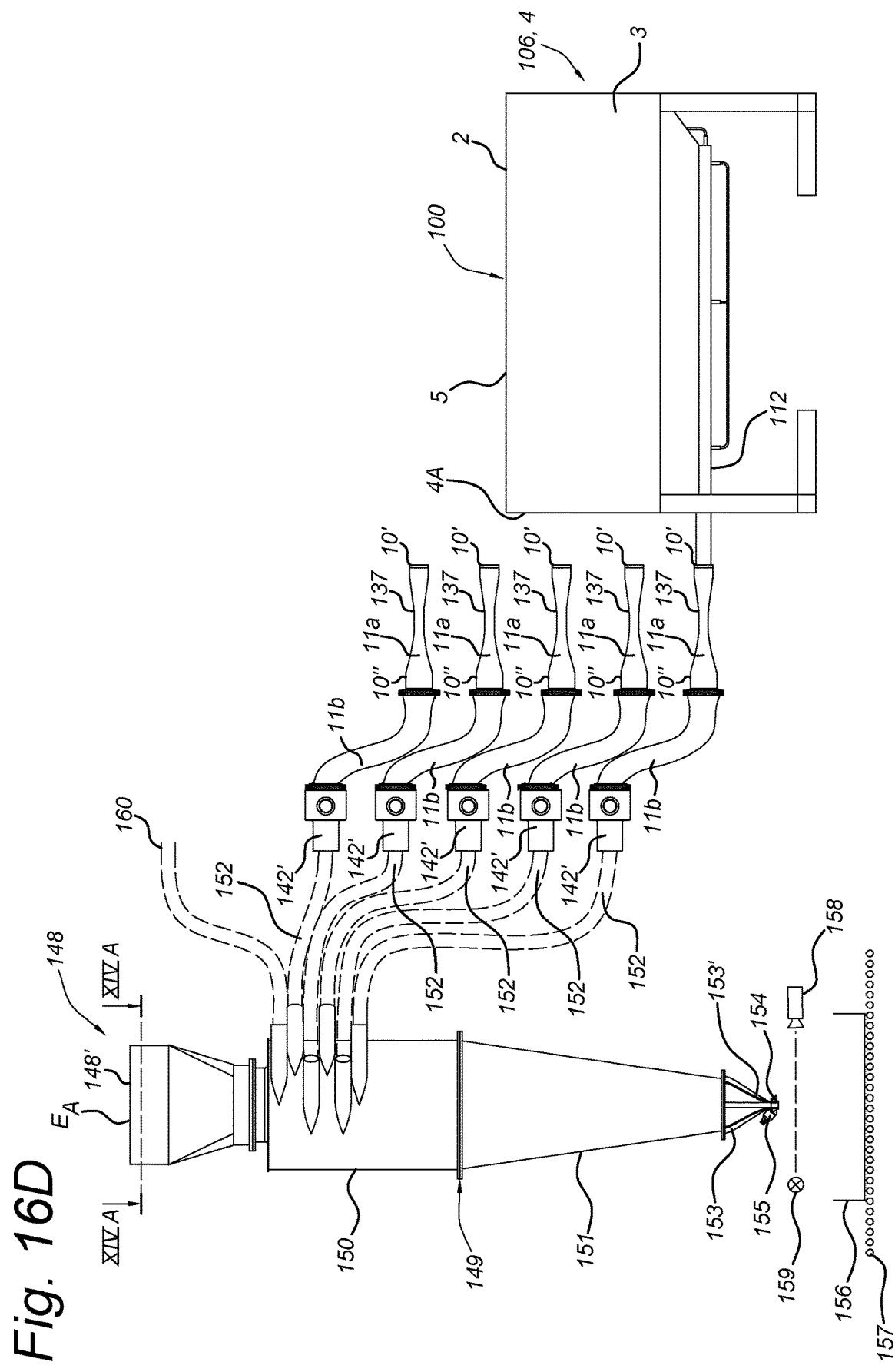

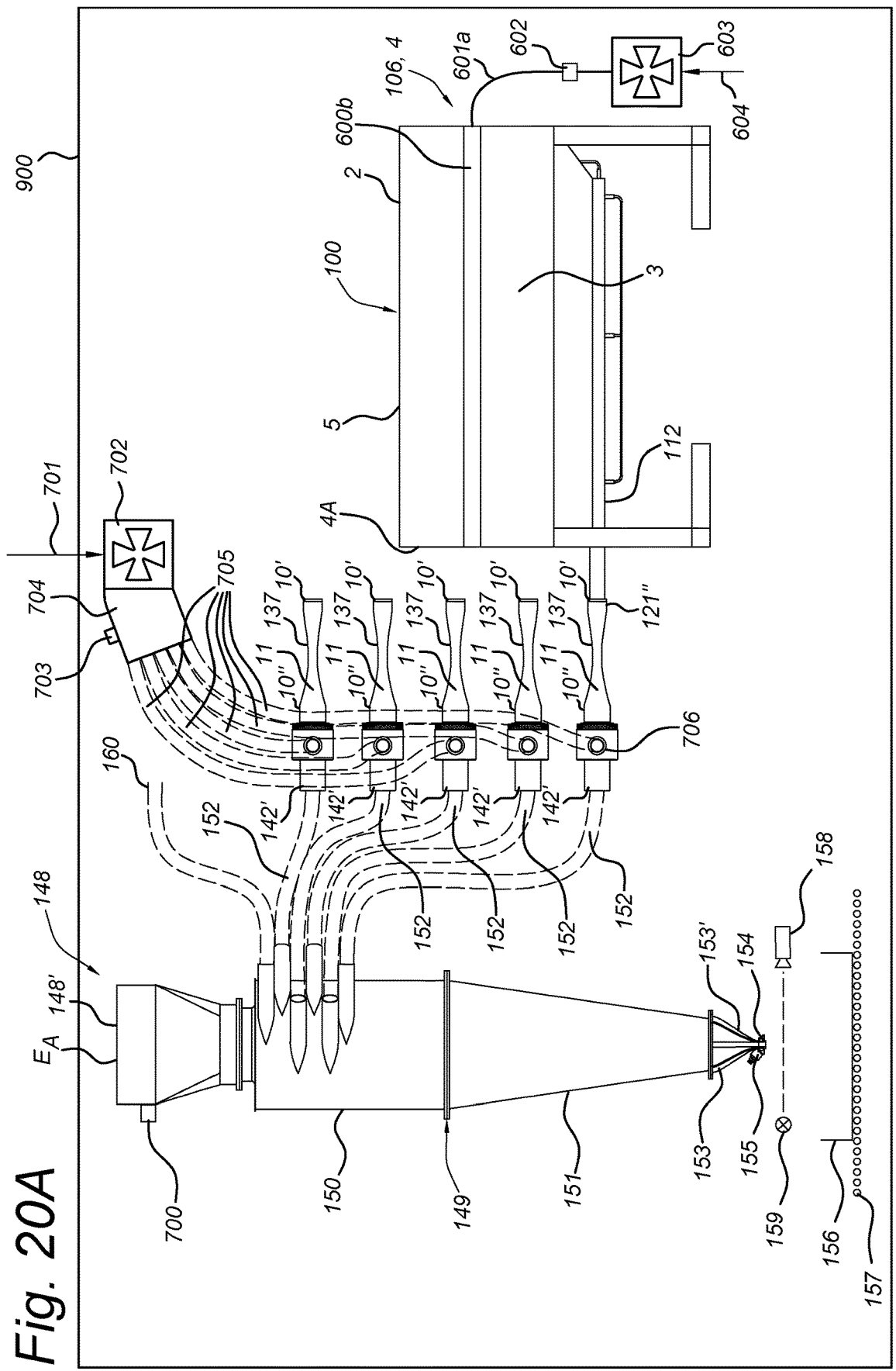

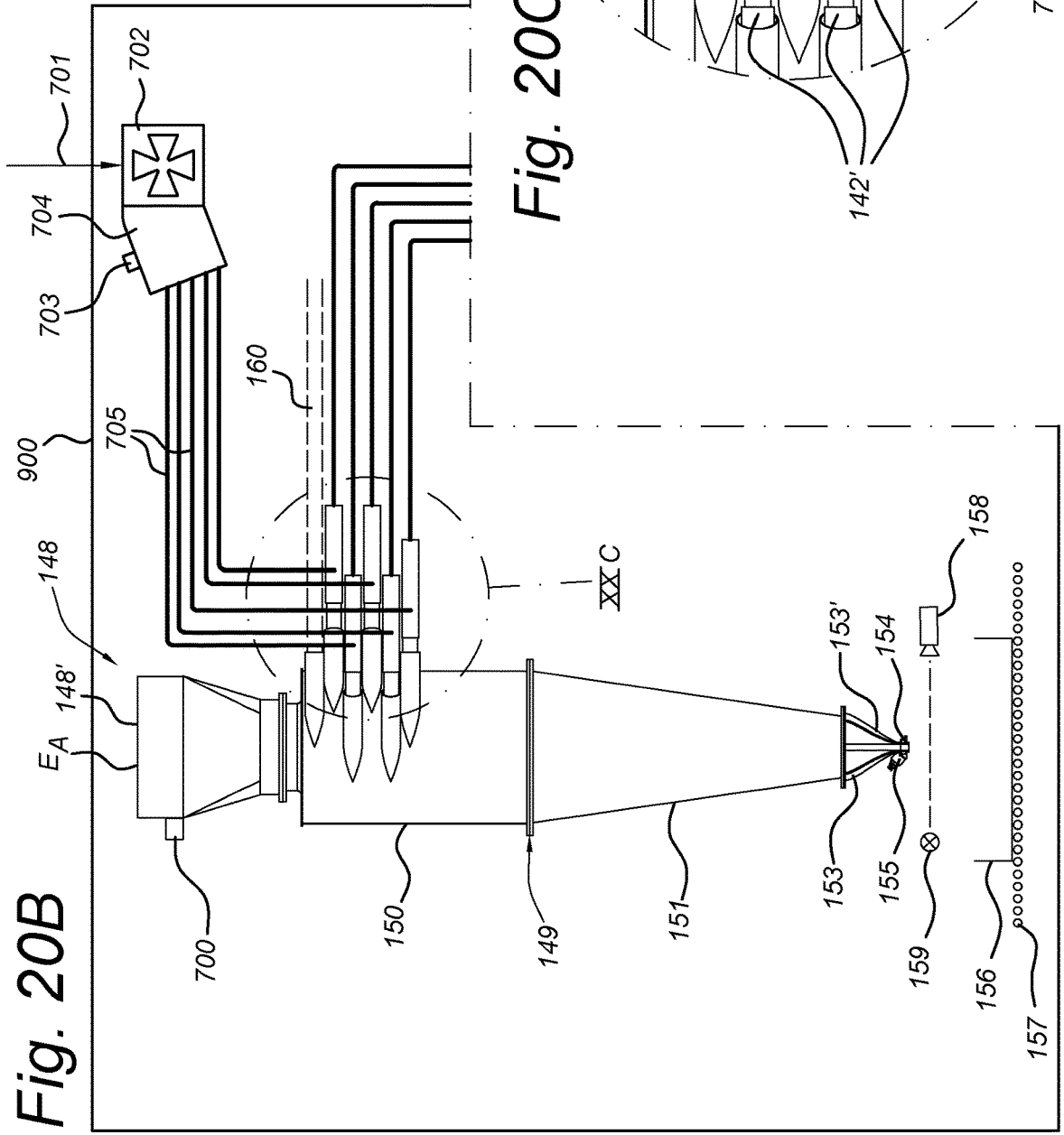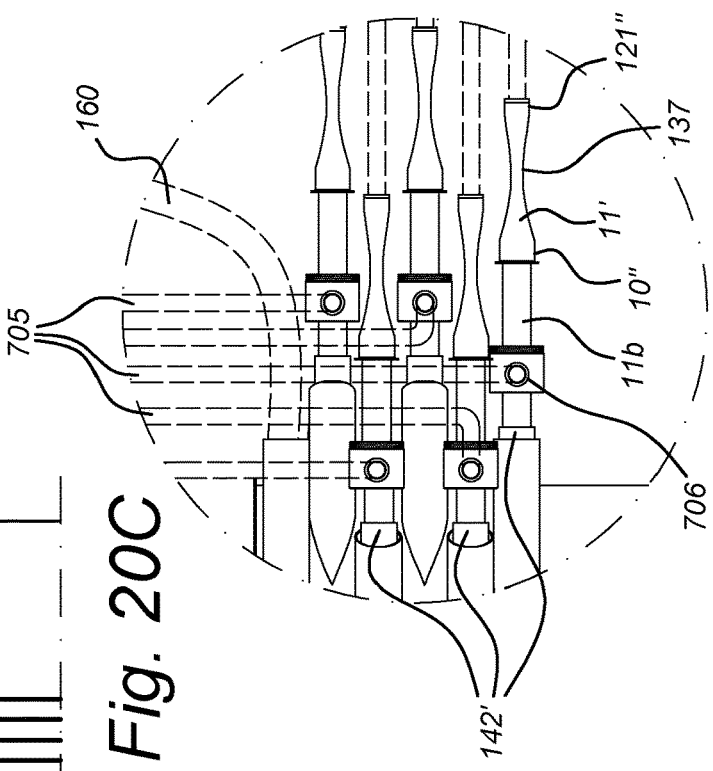

LIVE INSECTS TRANSPORT DEVICE

TECHNOLOGICAL FIELD

The invention relates to a device for use in large-scale industrial insect farming. More in particular, the invention relates to an insects transport device for transporting live insects from a first location to a predetermined second location, the insects transport device comprising a gas guiding unit, a gas discharge member and a feeder arrangement, wherein the insects transport device is configured to receive live insects such as freshly hatched neonate larvae, for example of black soldier fly, or mites, wherein the live insects are directly taken up in a laminar flow of gas after exiting the feeder arrangement in a free fall under influence of gravitation such that the live insects do not contact any surface of the insects transport device, and while in said gas are transported to a predetermined location in the insects transport device. The term 'insects' has to be understood as 'arthropods' throughout the specification, unless stated otherwise. Furthermore, the invention relates to the use of the device in industrial insect farming, such as large-scale farming of black soldier flies or mites. The invention also relates to a method of dosing live insects, wherein for example live insects are dosed which are essentially of the same age (e.g. within an age difference of 1 second-5 minutes), such as freshly hatched neonate larvae. In addition, the invention relates to a single dose of neonate larvae obtained with the method, wherein larvae have a small larvae-to-larvae age difference within the single dose.

BACKGROUND

Insects are considered one of the most promising means for protein and for organic residual recovery. Prominent examples of species proposed for the indicated applications include the black soldier fly (*Hermetia illucens*), the house fly (*Musca domestica*), and the mealworm (*Tenebrio molitor* L.).

Methods improving the efficiency of insect farming relating to improvements in farming colonies of insects having essentially the same age are particularly valuable for large scale production. This, because of the batch wise nature of the the insect farming steps that should be performed in order to be able to arrive at an economically viable scale. Since aiming for large-scale insect farming is a desired industrial activity that involves live animals, synchronization of the age of insects in a colony, which are then essentially in the same stage of the insect life cycle, would contribute to efficient use of farming facilities and would aid in achieving predictable production volumes. Furthermore, synchronization and steering of the age of batches of insect colonies which are in subsequent insect stages would further contribute to efficient use of farming facilities. However, methods and means for efficaciously and beneficially interfering in the life cycle of insects forming a colony, such that within the colony the insects essentially have the same age to the benefit of industrial-scale insect farming, are at present not available in the art.

U.S. Pat. No. 3,893,420 A discloses a method of mass-producing parasitic insects by infecting crop seeds with eggs of a host insect; collecting the imagoes of the host insect where their eggs are accumulated and attaching the imago eggs to a standard carrier; subjecting the eggs to climatic conditions and infecting the imago eggs with parasitic insects under climatic, natural conditions through phototaxis for conditioning the parasitic insect eggs so they are available for use in effective biological control material for controlling agricultural pests.

Russian patent application RU2336696C1 discloses a body for hatching and culturing insect larvae in liquid feed. The liquid feed is first mixed with insect eggs and then delivered in grooves of the body. When larvae have grown, these are collected from the body by applying an air flow over the liquid feed surface in the grooves.

U.S. Pat. No. 3,223,237 discloses a method and means for separating male insect pupae, female insect pupae and insect larvae based on size differences. Larvae and pupae are suspended in water, the suspension flown through a container, and pupae are retained in the container by accumulating at a screen in a container, the screen having an opening smaller the size of pupae.

U.S. Pat. No. 5,927,004 discloses a method and apparatus for coating insects with a tacky substance, and for subsequently delivery of the coated insects at a desired location. Insects are kept in a reservoir and batch-wise dosed to a container for provision with the coating and for subsequent delivery of the coated insects by application of a column of gas current for transport of the coated insects outward the apparatus.

U.S. Pat. No. 5,594,654 discloses a beneficial insect counting and packaging system for collecting and delivering known quantities of beneficial insect larvae and eggs. The system counts larvae and eggs of insects when these drop from plants or from a container. The insect larvae or eggs drop through a container provided with a sensor head, and then into a collection cup.

SUMMARY OF THE INVENTION

It is a first goal of the present invention to take away the above mentioned disadvantages, or at least to provide a useful alternative to the state of the art.

It is an object of the current invention to provide a means for automated and efficient transport of live insects such as live neonate larvae and live insects and other arthropods such as mites, preferably directly after the insects hatched. It is an aim of the invention to switch off any influence of natural behavior of the insects on the automated and efficient transport of live insects. Automation of the transport of the insects shall not depend or rely on any natural behavior, though instead should be controllable such that a controller (farmer) can transport insects at will without being dependent on insect natural behavior.

It is an object of the current invention to provide a means for automated and efficient transport of live insects such as live neonate larvae or mites, wherein the automated transport means does not do harm to the live insects and does not injure or even kill the live insects during transportation or thereafter as a result of the transportation with said means for transport of live insects. It is an aim of the invention to avoid any contact of a surface of the automated transport means with the living insects such as neonate larvae or mites. Killing or wounding insects is preventable this way, during automated transportation, and in addition, clogging of the automated transport means is avoided, for example clogging by accumulating insects at any surface of the automated transport means by adhering or sticking to said surface.

It is another or alternative object to provide a means for automated and efficient transport of live insects such as live neonate larvae or mites from the location where the insects hatch or where the insects are kept in a reservoir, to a location where the live insects are countable and preferably dosable and/or analyzable with regard to the age of the live insects transported by using the means for automated and efficient transport of live insects.

Furthermore, it is yet another or alternative object to transport live insects without imposing any harm to said insects and to transport live insects efficaciously from a first location to a predetermined second location, with minimal losses of insects by fall-out during transportation.

At least one of the above objectives is achieved by an insects transport device for transporting live insects from a first location to a predetermined second location, the insects transport device comprising a gas guiding unit, a first gas discharge member and a feeder arrangement, wherein the insects transport device is configured to receive live insects such as live freshly hatched neonate larvae, for example of black soldier fly, or mites, wherein the live insects are taken up in a laminar flow of gas immediately upon a free fall of the live insects from a reservoir of live insects under influence of gravity, and while in said gas are transported to a predetermined location in the insects transport device, without contacting any surface of the insect transport device. For example, neonate larvae are taken up by the laminar flow of gas current directly after hatching, e.g. within 1 second-10 minutes after hatching, when falling out of a reservoir of eggs, instantaneously after hatching. For example, mites are taken up by the laminar flow of gas current directly after driven through openings in the bottom of a mite reservoir upon applying heat/light upon the reservoir comprising the mites, from above the reservoir in the direction from top to bottom of the reservoir, such that mites migrate away from the source of heat/light, therewith making use of the negative thermotaxis/phototaxis.

The objective of keeping transported insects viable, alive and uninjured during transportation by the insects transport device of the invention, or thereafter as a consequence of the transportation by said insects transport device of the invention, is achieved by applying the insects transport device, according to the invention. That is to say, amongst other defining tests, the inventor established that live insects transported by the insects transport device of the invention are equally viable as live insects not transported by the insects transport device of the invention and otherwise being treated equally. No signs of any injury or increased number of dead insects due to subjecting live insects to transportation by the insects transport device of the invention was indicated, when compared to similar live insects not subjected to the transportation by using the insects transport device of the invention. Tests were performed with freshly hatched neonate larvae of black soldier fly (see the detailed embodiments section below).

Application of the invention is suitable for transporting and dosing e.g. black soldier fly larvae. More in general the device of the invention is suitably applied for the transport and dosing of an arthropod. Typically, the device of the invention is used for transportation and for dosing of any of the species Lacewings (e.g. *Chrysoperla carnea*), for which larvae hatched from eggs placed in the device can be transported in the airstream and dosed in appropriate amounts to get accurate numbers in feeding batches or the end product; Coccinelid beetles (e.g. Cryptolaemus *montrouzieri*), for which collected eggs can be placed in the insect transport device and subsequently larvae can be transported in the airstream and dosed in appropriate amounts to get accurate numbers in feeding batches to rear until pupae/the adult stage or directly as an end product (as larvae); predatory bugs (e.g. *Macrolophus pygmaeus*), for which collected eggs can be placed in the insect transport device and subsequently, nymphs can be transported in the airstream and dosed in appropriate amounts to get accurate numbers in feeding batches to rear until the adult stage or directly as an end product (flightless nymphs). Of course, the device of the invention can be applied with many other insects, such as pollinators (e.g. the onion fly, *Delia antiqua*) and predatory beetles (e.g. the greenhouse rove beetle, *Dalotia coriaria*). Indeed, for terrestric fly species of which the eggs can be collected, these species are suitable application in the device of the invention, e.g. for dosing larvae, eggs. Where appropriate, throughout the specification, and in the claims, the term ‘insects’ can be read as ‘arthropods’, covering for example flies and mites, such as the black soldier fly, more in particular the (neonate) larvae of the black soldier fly, as well as mites, unless it is clear from the context that specifically insects according to the common definition are referred to. It is appreciated by the skilled person that the insect transport device of the invention is also suitable for transport and for dosing of other species such as worms, unrelated to the larval form of arthropods, e.g. insects.

As said, the insects transport device of the invention transports live insects to a predetermined location when in operation. At such predetermined location in the insects transport device, a tunable outflow of live insects is provided for, with regard to the number of live insects exiting the insect transport device per time unit, e.g. per second or per minute, and/or with regard to the number of live insects exiting the insects transport device per volume of fluid in the laminar flow of fluid. Herewith, the insects transport device provides for a means to deliver live insects per time unit and/or per volume in a manner that such transported live insects are for example subsequently countable after exiting the device of the invention and/or are dosable by for example receiving an amount of live insects in a receptacle for a certain period of time in which the insect transport device is in operation, and/or receiving the amount of live insects in a certain volume of gas in the laminar flow of gas exiting the insect transport device when in operation.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

The embodiments of the invention described herein can operate in combination and cooperation, unless specified otherwise.

Furthermore, the various embodiments, although referred to as "preferred" or "e.g." or "for example" or "in particular" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

An aspect of the invention relates to an insects transport device comprising: a gas guiding unit comprising a distal end and a proximal end, and at least one longitudinal gas guiding member comprising a distal end and a proximal end, wherein the distal end of the gas guiding member is arranged at the distal end of the gas guiding unit and wherein the proximal end of the gas guiding member is directed toward the proximal end of the gas guiding unit, wherein the at least one gas guiding member further comprises a smooth top surface extending from the distal end to the proximal end of the gas guiding member, the top surface comprising a live insect larvae receiving portion between the distal end and proximal end of the at least one gas guiding member; a first gas discharge member located at the distal end of the gas guiding unit and being configured to connect to a source of gas, wherein the first gas discharge member is further configured to provide a first laminar flow of gas over the top surface of the at least one gas guiding member from the distal end to the proximal end thereof during operation of the transport device; and wherein the transport device further comprises a feeder arrangement located above the live insect larvae receiving portion of the top surface of the fluid guiding unit, wherein the feeder arrangement is configured to receive at least one reservoir for releasing live insect larvae above the live insect larvae receiving portion, wherein the insect larvae transport device further comprises a casing covering the gas guiding unit and the feeder arrangement.

An embodiment is the insect larvae transport device according to the invention, wherein the first gas discharge member is further configured to provide a continuously flowing first laminar flow of gas over the top surface of the at least one gas guiding member from the distal end to the proximal end thereof during operation of the transport device.

An embodiment is the insects transport device according to the invention, wherein the feeder arrangement is configured to receive at least one reservoir for releasing live insects by gravity-driven free fall through gas medium in the insect transport device, above the insects receiving portion, and therewith in the first laminar flow of gas, such that during operation of the insects transport device insects freely flow without contacting a surface of the gas guiding member(s).

An embodiment is the insects transport device, wherein the feeder arrangement is configured to receive at least one reservoir for releasing live insects by gravity-driven free fall through gas medium present in the insect transport device, above the insects receiving portion, and therewith in the first laminar flow of gas, such that during operation of the insects transport device insects freely flow from the reservoir to and into and with the first laminar flow of gas without contacting a surface of the gas guiding member(s).

An aspect of the invention relates to an insects transport device, in particular an insect larvae transport device and a mite transport device, comprising: a gas guiding unit comprising a distal end and a proximal end, and at least one longitudinal gas guiding member comprising a distal end and a proximal end, wherein the distal end of the gas guiding member is arranged at the distal end of the gas guiding unit and wherein the proximal end of the gas guiding member is directed toward the proximal end of the gas guiding unit, wherein the at least one gas guiding member further comprises a smooth top surface extending from the distal end to the proximal end of the gas guiding member, the top surface comprising a live insects receiving portion, such as a live insect larvae receiving portion or a live mite receiving portion, between the distal end and proximal end of the at least one gas guiding member, and wherein optionally the fluid guiding member is tilted at an angle $\alpha$ relative to the horizontal; a first gas discharge member located at the distal end of the gas guiding unit and being configured to connect to a source of gas, wherein the first gas discharge member is further configured to provide a first laminar flow of gas, for example a continuously flowing first laminar current of gas, over the top surface of the at least one gas guiding member from the distal end to the proximal end thereof during operation of the transport device; and wherein the transport device further comprises a feeder arrangement located above the insects receiving portion of the top surface of the gas guiding unit, wherein the feeder arrangement is configured to receive at least one reservoir for releasing live insects by gravity-driven free fall through gas medium in the insect transport device, above the insects receiving portion, and therewith in the first laminar flow of gas, such that during operation of the transport device insects freely flow without contacting a surface of the gas guiding member(s), wherein the insect transport device further comprises a casing covering the gas guiding unit and the feeder arrangement, and wherein the feeder arrangement optionally further comprises a temperature control unit for controlling the temperature at the inner side of the casing and/or optionally further comprising a unit for controlling relative air humidity at the inner side of the casing.

An aspect of the current invention relates to an insects transport device, comprising: a fluid guiding unit comprising a distal end and a proximal end, and at least one longitudinal fluid guiding member comprising a distal end and a proximal end, wherein the distal end of the fluid guiding member is arranged at the distal end of the fluid guiding unit and wherein the proximal end of the fluid guiding member is directed toward the proximal end of the fluid guiding unit, wherein the at least one fluid guiding member further comprises a smooth top surface extending from the distal end to the proximal end of the fluid guiding member, the top surface comprising a live insects receiving portion between the distal end and proximal end of the at least one fluid guiding member, and wherein the fluid guiding member is tilted at an angle $\alpha$ relative to the horizontal; a first fluid discharge member located at the distal end of the fluid guiding unit and being configured to connect to a source of fluid, wherein the first fluid discharge member is further configured to provide a first laminar flow of fluid over the top surface of the at least one fluid guiding member from the distal end to the proximal end thereof during operation of the transport device; and wherein the transport device further comprises a feeder arrangement located above the live insects receiving portion of the top surface of the fluid guiding unit, wherein the feeder arrangement is configured to receive at least one reservoir for releasing live insects above the live insects receiving portion, wherein the insects transport device further comprises a casing covering the fluid guiding unit and wherein the feeder arrangement further comprises a temperature control unit for controlling the temperature at the inner side of the casing and/or further comprising a unit for controlling relative air humidity at the inner side of the casing.

When in operation, the insect transport device of the invention provides a tunable supply of live insects in the laminar flow of fluid at a predetermined location in the insects transport device, such as for example at the downstream location of the laminar flow of gas, i.e. the proximal end of the gas guiding member. As described, this way, a stream of live insects in a laminar flow of gas is provided that is for example suitable for subsequently feeding for example a live insect analysis arrangement, upon exiting of the live insects from the insects transport device. Typically, a live insect analysis arrangement is an imaging device comprising analysis software, which is capable of imaging live insects exiting the insects transport device and passing through an imaging zone, and capable of providing instant feedback on for example the size and/or shape and/or color and/or weight of the transported live insects. This provides a manner of sorting and/or dosing live insects transported by the insects transport device. For example, transported live insects are collected in a receptacle when a certain predetermined cut-off for a parameter value such as volume, size, etc., is determined, and transported live insects are not collected for example for further farming, when said certain predetermined cut-off fora parameter value is not reached or exceeded, as the case may be. For example, sorting live insects based on a predetermined size, or average size with a certain size tolerance, or size window, improves the synchronization of insect age within a colony consisting of insects having such predetermined size, etc. Use of the insects transport device thus contributes to improved farming performance by contributing to establishment of insect colonies comprising insects with less difference in age than what is obtainable when applying current methods of (small scale) insect farming.

In one embodiment, the insects transport device according to the invention is a device wherein the at least one gas guiding member has a length in the longitudinal direction of between 10 cm and 200 cm, preferably between 20 cm and 140 cm, more preferably between 25 cm and 120 cm, most preferably about 25 cm to 50 cm. In one embodiment, the insects transport device according to the invention is a device wherein the at least one gas guiding member has a length in the longitudinal direction of between 30 cm and 400 cm, preferably between 40 cm and 300 cm, more preferably between 50 cm and 150 cm, most preferably about 65 cm to 120 cm.

In one embodiment, the insects transport device is a device wherein said transport device comprises at most one longitudinal fluid guiding member.

Large scale insect farming implying an industrial scale providing for an output of for example insect derived proteins, amino-acids, oil, lipids, fat, etc., which is economically feasible, is supported by the use of the insects transport device, said device having certain minimal dimensions relating to minimal turnover of transported live insects. It has been established by the current inventors that an insect transport device comprising a gas guiding member with a length in the longitudinal direction of between 10 cm and 200 cm, such as about 100 cm to 150 cm or such as about 60 cm to 80 cm provides for the top surface comprising a live insects receiving portion between the distal end and proximal end of the at least one gas guiding member, wherein said live insects receiving portion has a size suitable for receiving an amount of live insects in the gas of the laminar flow, which is sufficient and enough for transporting numbers of live insects suitable for farming of the insects at the desired large scale.

An embodiment is the insects transport device according to the invention, wherein the casing covering the gas guiding unit and the feeder arrangement is a thermally insulated casing. Providing an insect transport device with thermally insulated top wall and side walls has the advantage that the climate control inside the device is supported. That is to say, due to the thermally insulation, temperature inside the insect transport device is maintained constantly within a small temperature range such that condensation of vapor such as water vapor at any surface inside the device is prevented, which condensation would otherwise occur when for example the temperature inside the device drops upon lowering of the temperature in the space surrounding the device. The inventors established that by applying a thermally insulated casing, the temperature inside the insect transport device is maintained constantly at a value dictated by the temperature of the constantly laminar flowing gas in the gas current applied inside the device. Providing a thermally insulated casing is for example established by implying thermal insulation in or on the walls of the casing, such as implying a material (sheets, plates, film of a material) suitable for thermal insulation in the walls or onto the walls. Herewith, temperature drops or rises at the outside surface of the casing due to changes in the temperature at the exterior side of the device do not influence the temperature inside the device. Provision of layers of thermally insulating material as part of the casing side walls and top wall contributes to maintenance of a temperature difference between the controlled temperature inside the casing and the ambient temperature outside the insects transport device, when such temperature difference between inside and outside the device occurs. As a consequence, relative air humidity inside the insect transport device is solely determined by the constant temperature inside the device, such that condensation of water at surfaces inside the device does not occur. Therefore, incorporating a temperature control unit in the insect transport device is optional though not an essential requirement. The same for an absolute air humidity control unit. Since condensation at surface inside the insects transport device does not occur due to the application of a thermally insulated casing, free transport of live insects in the laminar gas current over the gas guiding member(s) is unhindered by water droplets and the risk for insects contacting wet surfaces while flowing by, and thereby adhering to said surfaces such that unhampered transport is interrupted, is prevented by applying the isolated casing. At least any one or more of the top wall, 1-4 side walls and the bottom floor are thermally insulated in the casing. For example, the top wall and four side walls of the casing are provided with an insulating material.

An embodiment is the insect transport device comprising at most one longitudinal gas guiding member. In one embodiment, the insects transport device according to the invention is a device wherein said transport device comprises at least two imbricatedly coupled longitudinal gas guiding members, the gas guiding members being imbricatedly coupled with a coupler located at the proximal end of a first gas guiding member and the distal end of a second gas guiding member. Preferred is an insects transport device comprising two to six longitudinal gas guiding members, more preferred the insects transport device comprises three to four longitudinal gas guiding members. The insects transport device comprising for example three longitudinal gas guiding members encompasses a live insects receiving portion spanning a length of between about 75 cm and 800 cm, such as between about 120 cm and 200 cm. With such a size of the live insects receiving portion, space for positioning up to about 800 reservoirs for releasing live insects above said live insects receiving portion in the feeder arrangement is available, for example in two rows of about 400 reservoirs, each. For example, about a hundred reservoirs or about 128 reservoirs are positioned in the feeder arrangement, in two rows of fifty or 64 reservoirs or in a single row of reservoirs. Preferred is a live insects receiving portion spanning a length of between about 90 cm and 160 cm, which provides sufficient space for positioning up to between about 34 reservoirs and 68 reservoirs for releasing by exerting gravitation, live insects above said live insects receiving portion from the feeder arrangement and unhindered in the laminar gas current flowing over the gas guiding member, for example in two rows of about 34 reservoirs, each, or in a single row of 34 reservoirs or 68 reservoirs. These numbers of reservoirs are configured to contain numbers of live insects for release in the live insects receiving portion of the insects transport device, which are sufficiently high as to provide for a stream of transported live insects during a sufficiently long period of time, e.g. 1 hour to 4 days, preferably 3 hours to 3 days, more preferably between 12 hours and 60 hours, most preferably between 14 hours and 48 hours, such as about 14 hours, in order to support large scale insect farming. For example, 30 to 70 reservoirs are positioned in the feeder arrangement of the insect transport device, for example for a period of releasing live insects into the laminar flow of gas during about 48 hours or about 14 hours, when operating the insect transport device. Typically, for example a reservoir containing insect eggs contains between about 10.000 and 500.000 eggs, i.e. live insects, preferably between about 30.000 and 100.000 eggs. Methods improving the efficiency of egg collection from insects such as black soldier fly in a reservoir suitably for application in the insect transportation device are particularly valuable for large scale production because the enormous quantity, delicacy, small size and stickiness of eggs. Therefore, it is beneficial to collect insect eggs in a specific location since this simplifies collection operations and allows for efficient subsequent handlings, i.e. hatching while positioned above the live insects receiving section of the insects transport device of the invention. In the event that the location is a device designed to collect eggs, it will henceforth be referred to as an "ovisite" throughout this application. A preferred reservoir for positioning in the feeder arrangement of the insect transport device is an ovisite of between about 15 cm and 60 cm (width) times between about 10 cm and 40 cm (height) times between about 0.6 cm and 2.4 cm (depth), such as an ovisite of about 30 cm (width) times about 20 cm (height) times about 1.2 cm (depth). A preferred ovisite for use in the insects transport device when in operation, is an ovisite with for example honeycomb architecture comprising for example hexagonal openings, such as a cardboard honeycomb. Such cardboard honeycomb comprises sufficient and enough space for bearing a number of live insects, i.e. insect eggs, which number is sufficiently high to be able to release a suitable quantity of live insects into the laminar flow of gas in the insects transport device.

With a number of reservoirs of between 25 and 100, such as between 34 and 68, or such as about 32 or 64 reservoirs, the reservoirs being honeycombs such as polymer or cardboard honeycombs comprising insect eggs, such as those from black soldier fly, the insect transport device is operable for 1 to 3 days, preferably for about 2 days, with regard to the number of live insects, here freshly hatched neonate larvae such as those from black soldier fly, exiting the insects transport device and becoming available for subsequent required steps of insect farming, i.e. culturing in a suitable substrate. For example, the reservoirs applied in the insect transport device are reservoirs such as honeycombs, which are typically ovisites of about 2 cm×22 cm×33 cm, that have been located in an adult insect cage comprising about 1.000 to 30.000 gravid female insects, such as about 4.000 gravid insects, such as black soldier flies, for a period of between 12 hours and 72 hours such as for about 24-48 hours, such that those numbers of gravid insects have laid eggs for this indicated period of time. These ovisites filled with insect eggs comprise numbers of live insects enough for releasing sufficient hatched neonate larvae into the live insect receiving section by gravity-driven free fall from the ovisite, unhindered and directly into the laminar flow of gas of the insect transport device while in operation. For example, said 32 to 64 ovisites then encompass by estimation between 320.000 eggs and 3.2 million eggs, typically about 1.5 million eggs such as those from black soldier flies for example having an egg to egg age difference of two days or less.

One of the various benefits provided with the insects transport device is the possibility to collect neonate larvae of insects which larvae have a narrow window of difference in age. "Narrow" in the context of this synchronization of age of a batch of live insects is to be understood as a maximum age difference between live insects in a batch of live insects transported by the insect transport device of the invention of at most 2 hours, and typically less than 1 hour, such as for example between 5 minutes and 45 minutes, or for example 1 second-4 minutes, such as about 10 seconds, 30 seconds, 1 minute, 2 minutes. The age difference amongst neonate larvae within a single dose of larvae provided with the insect transport device is for example only or mainly determined by the number of hatching larvae per time unit, e.g. number of hatched neonate larvae per second (also depending on the number of eggs contained by the reservoir in the insects transport device), and/or by the difference in crawling speed or dropping/falling time of the individual larvae, when the moment of the hatching in the reservoir up to the moment that the larvae are taken up in the laminar flow of air is considered, and/or for example combined with the time required to count and obtain a number of larvae from the device as a single dose of larvae. A single dose of neonate larvae is typically received by a crate for rearing larvae such as neonate larvae of the black soldier fly. A "batch" is here defined as a number of live insects that has been transported with the insects transport device and that are isolated from the laminar flow of gas after exiting of the transported live insects out of the insects transport device, the number of transported live insects in a batch being defined by the time period of collecting transported live insects and/or the number of transported live insects retrieved from a certain volume of fluid exiting the insects transport device. Typically, a batch of transported live insects is collected in a receptacle positioned downstream from the laminar flow of fluid exiting the insects transport device. Typically, a batch of transported live insects, such as freshly hatched neonate larvae, such as black soldier fly larvae, or mites, exited the insects transport device, encompasses between 3.000 live insects and 300.000 live insects, preferably between 5.000 and 100.000 live insects, such as about 40.000 neonate larvae, e.g. of black soldier fly, or mites. It is thus due to the current invention that batches are provided of sufficiently high numbers of transported live insects, such as freshly hatched neonate larvae, such as black soldier fly larvae, or such as mites, wherein the individual live insects in a batch have a synchronized age that is tunable with a predetermined range. For example, a batch of transported live insects is obtainable that encompasses about 50.000 live insects having an age difference of less than one hour, or that encompasses about 150.000 live insects having an age difference of between 5 minutes and 30 minutes.

A further benefit achieved with the insects transport device is the provision of a stream of live insects exiting the device, which insects are countable such that a predetermined number of live insects can be dosed and for example packed in a receptacle or introduced in a crate provided with insects feed substrate, as the case may be. Since free flowing live insects in the laminar gas current are the only particulates exiting the insects transport device, counting particles equals counting live insects. The counted number of particles per time frame corresponds thus with the number of live insects that exited the device. Herewith, a robust measure and means is provided for the provision of constant doses of live insects over time when a single reservoir or batch of reservoirs inside the insect transport device is considered, and when different batches of reservoirs which are sequentially introduced one after another in the insects transport device, is considered. This constant and reliable dosing is for example beneficial to the provision of predetermined doses of mites, when the number of mites is considered. Herewith the current problem of large mite batch to batch variabilities when the number of mites is considered, is largely solved by applying the insects transport device filled with a batch of reservoir(s) comprising mites.

It is one of the many benefits achieved with the insect transport devices of the invention that the transport device is particularly suitable for transportation of live neonate larvae of the black soldier fly, which larvae have a body diameter of between 1 mm and 4 mm and a body length which ranges between 5 mm and 12 mm. It is one of the many benefits achieved with the insect transport devices of the invention that the transport device is particularly suitable for transportation of live neonate larvae of the black soldier fly, which larvae have a sticky body surface resulting in adherence to many surfaces such as metal surfaces and polymer surfaces typically applied inside the insects transport device and for tubings, etc. Since hatching larvae freely fall downwards from the reservoir directly upon hatching, and since the falling larvae are unhindered taken up in the gas current of the laminar gas flow over the gas guiding member(s), any contact of the sticky larvae with a surface of the insects transport device is avoided such that adhering of larvae to such surfaces is adequately and efficiently prevented. Therewith, losses of live larvae are prevented, and the risk for damaging or even killing larvae by contacting any surface, is addressed.

A further benefit provided by the insects transport device is the possibility to automate the preparing of batches of transported live insects having a synchronized age within a predetermined time window of for example between 2 minutes and 4 hours, such that for a time period of for example two days the insects transport device delivers amounts of transported live insects enough for, for example, providing between 2 and 150 batches of live insects per hour, such as 5-100 batches, or 10-70 batches, each batch encompassing for example between 1.000 and 600.000 live insects, such as about 400.000 live insects or about 80.000 live insects, e.g. neonate larvae or mites, the transported live insects in each batch having a maximum age difference of less than 3 hours, such as for example between 3 minutes and 2 hours, or between 6 minutes and 1 hour. These production volumes with regard to the number of batches, the amount of live insect per batch and the synchronized age of live insects in each batch, are suitable for insect farming at a scale required for profitably running a business. That is to say, by applying the insects transport device, the number of output batches comprising the indicated numbers of live insects at an insect age within the relatively small window of ages, i.e. batches of live insects with selected numbers of insects having a synchronized age within a predetermined time window, is sufficient and suitable for running an insect farm in a manner that farming equipment has a run time higher than run times that would be reachable without application of the insect transport device. It is due to the inventors that now an insects transport device has become available that makes it possible to provide a predetermined number of colonies of live insects per time unit, e.g. per day, of a predetermined colony size in numbers of live insects, and of an average age within a predetermined time window, such that insect rearing equipment and insect breeding equipment used for farming of subsequent stages of the insect life cycle are better used with regard to their run time, preferably optimally used for insect farming during a prolonged period of run time. Thus, the insect transport device of the invention provides the opportunity to optimize or improve the efficiency of sequentially using rearing and breeding equipment for farming insects, with less or minimal down time, i.e. idle time, for each specific farming equipment which would be due to for example non-availability of a following colony at the right stage in the insect life cycle at the moment the equipment for farming such colony in such stage becomes idle.

Current practice of small scale insect farming encompasses placement of an ovisite comprising insect eggs with an age difference of for example 2-3 days, for two-three days above a tray comprising feed for the hatched neonate larvae, which fall on top of the feed once hatched. It is clear that this approach comes with the drawback, now solved by application of the insects transport device, as here above outlined, that neonate larvae have an age difference of as large as 2-3 days, compared to the seconds to minutes to hours age difference now obtainable with the insects transport device, while still being able to provide the same numbers of larvae per batch.

In one embodiment, the insects transport device is a device wherein the coupler imbricatedly coupling the at least two gas guiding members is provided with a further gas discharge member comprising a connector configured to connect each further gas discharge member to a source of gas, and wherein the further gas discharge member(s) is/are configured to reinforce from below the first laminar flow of gas over the top surface of the at least one gas guiding member from the distal end to the proximal end of the gas guiding unit during operation of the insects transport device. This way, performance of the insects transport device is further increased, since the further gas discharge members are positioned such that gas exiting the gas discharge members at an adjusted and regulated speed and pressure adds to the laminar flow of gas passing over the imbricatedly coupled gas guiding members. The pressure at which the further gas provided by the further gas discharge members is released into the laminar flow of gas is fine-tuned and adjusted in relation to the length of the flow path of the laminar flow of gas between from the first gas discharge member to the subsequent further gas discharge member. It is appreciated that the longer the path between two subsequent flow discharge members, the higher the pressure at which the further gas is provided through the further gas discharge member(s). An advantage of providing the insect transport device with the at least one further gas discharge member, is that the laminar flow of gas (the laminar current of gas) is more constant with regard to the velocity of the volume elements of gas in the laminar flow, and is more constant with regard to the direction of the laminar flow of gas from the distal end of the gas guiding unit to the proximal end of the gas guiding unit. Providing further gas discharge member(s) at the indicated location in the insects transport device for example contributes to preventing live insects which are taken up by the laminar flow of gas, immediately and unhindered during the free fall of the insects from the reservoir, from bumping to the top surface of the gas guiding units, or even sticking to said top surface, due to gravitation force. Providing further sources of gas along the flow path of the laminar flow of gas at least partly eliminates the effect of gravity on the live insects taken up by the gas in the laminar flow. Thus, losses due to live insects released from the laminar flow of gas along the path from the distal end of the gas guiding member to the proximal end of said gas guiding member is at least reduced, if not prevented. Furthermore, by application of further gas discharge members along the path of the laminar flow of gas, for reinforcing said laminar flow of gas, a lower flow, that is to say a flow at lower pressure and/or at lower gas velocity, is sufficient along the full length of the flow path in the insect transport device, when compared to applying a single gas discharge member at the distal end of the gas guiding member. Applying such a lower flow by the application of multiple gas discharge members avoids the occurrence of turbulence in the air surrounding the laminar flow of gas at least to some extent. Turbulence increases with increasing gas velocity and/or increasing air pressure, thus applying lower velocity and/or lower air pressure is beneficial to the efficiency of transporting live insects such as neonate larvae in the laminar flow of gas, preventing the insects from being transferred to undesired directions due to turbulence. Applying the additional gas discharge members at the locations of imbricated consecutive gas guiding members thus provides a way to boost the laminar flow of gas, such that the air pressure and/or air velocity is reduced, which provides better controllable transport of the neonate larvae in the laminar flow of gas, e.g. air.

In one embodiment, the insects transport device is a device further comprising a casing covering the gas guiding unit and the feeder arrangement. Preferred is the insects transport device comprising a casing covering the gas guiding unit and the feeder arrangement, wherein the side walls and the top wall of the casing are thermally insulated side walls and a thermally insulated top wall. For example, the casing is thermally insulated with plates suitable for thermal insulating, for example made of polyisocyanurate (PIR) provided at both sides of the plate with polyethylene coated aluminum, such as Selthaan Alu plates (Kingspan). Typically, the material applied for thermally insulating the insects transport device has a λ-value of 0.028 W/mK or higher. For example, thermally insulating plates as part of the side walls and the top wall of the casing, are applied, which have a thickness of 25 mm or more. Typically and suitably, thermally insulating plates are applied which have an Rd value, R-value, of 0.85 $m^2$*K/W. Thermally insulating the casing and therewith the insects transport device with such thermally insulating material provides for a device in which condensation of water vapor at inner surfaces is highly limited, or even not occurring at all, when for example the gas applied inside the insects transport device is air at a temperature of 25° C.-35° C., with a relative air humidity of 55%-95%, such as air at 26° C.-30° C., such as 28° C., and such as a relative air humidity of 50%-60%, or 45%-65%, such as about 55%, or such as a temperature of 25° C.-35° C., with a relative air humidity of 75%-95%. The gas applied for the laminar flow of gas over the gas guiding unit(s) typically is air at a temperature of 25° C.-35° C., with a relative air humidity of 45%-65%, such as air at 28° C., and a relative air humidity of about 55%. Such air does not result in water condensed at any surface inside the insects transport device upon application of the thermally insulating casing.

In one embodiment, the insects transport device is a device further comprising a temperature control unit for controlling the temperature at the inner side of the casing and/or further comprising a unit for controlling relative air humidity at the inner side of the casing.

The insects transport device provided with a casing provides for several further benefits with regard to efficiency of providing numbers of live insects within a certain time frame and having a certain minimal difference in age. The casing encloses for example the feeder arrangement and gas guiding member in a manner that effectively a closed inner space is provided having openings for receiving the first and optionally further gas discharge members and an opening at the proximal end of the gas guiding member providing an exit for transported live insects. In such a closed inner space, temperature is controllable, such as automatically controllable at a selected temperature or selected temperature range. This way, reservoirs comprising live insects such as eggs, for example of black soldier fly, or reservoirs comprising mites, are maintainable at a controlled and predetermined temperature for stimulating optimal hatching, or for heat/light stimulated migration of mites through openings in the bottom wall of the mites reservoir. The same holds true for controllability of relative air humidity inside the cased insect transport device. Typically, for optimal release of live insects from the reservoirs into the live insect receiving portion of the insects transport device, the temperature inside the cased insect transport device is for example between 21° C. and 27° C., preferably about 26° C., when for example ovisites comprising eggs of black soldier fly are applied in the feeder arrangement, when the insects transport device is operating. Typically, for optimal release of live insects from the reservoirs into the live insect receiving portion of the insects transport device, the relative air humidity inside the cased insect transport device is for example between 45% and 95%, preferably about 60% to 85%, when for example ovisites comprising eggs of black soldier fly are applied in the feeder arrangement, when the insects transport device is operating, according to the invention.

In one embodiment, the insects transport device is a device wherein the gas is temperature conditioned gas and/or relative air humidity conditioned gas. It is preferred that the gas is a gas selected from gases such as air, ambient air, conditioned air with regard to temperature and/or relative humidity and/or enrichment of one or more gases with regard to the naturally occurring ratio and/or depletion such as partial depletion of one or more gases such as ammonia, methane, nitric oxides, with regard to the naturally occurring ratio and content, and/or addition of other gases than the naturally occurring gases of air, a mixture of oxygen and nitrogen, optionally the gas is humidified and/or temperature controlled air. Since insects commonly thrive well in ambient air, the application of ambient air, or just air, used in the first laminar flow is preferred. Of course, application of a liquid such as water, e.g. tap water or water comprising nutrients, is suitable as well, for the laminar flow of a fluid other than a gas in the insect transport device of the invention, although a gas is preferred. Live insects have a higher survival time in a gas such as ambient air, when compared to when the fluid is for example water. Furthermore, temperature control of a fluid which is a gas such as ambient air is less energy consuming than temperature control of a same volume of a liquid such as water in the laminar flow of fluid. Further benefits of applying a gas such as air for the laminar flow of fluid in the live insect transport device of the invention, over applying a liquid such as water, is that applying a liquid to transport live insects implies the necessity to use filters once the live insects such as neonate larvae, e.g. of black soldier fly, or mites, exited the transport device. The requirement to use filters results in increased steps in processing live insects, coming with an increased demand on time, labor and financial resources, and with an increased risk for system failures such as by clogging of filters, to name a few drawbacks relating to the application of a liquid, not apparent when using a gas such as air in the laminar flow of fluid.

In one embodiment, the insects transport device is a device wherein the gas is air. Furthermore, from a cost perspective, use of air as the gas in the laminar flow of gas is beneficial, especially for the insect farming at industrial scale. Preferably, the gas in the laminar flow when the insect transport device is in operation is temperature controlled air. Relative air humidity controlled air is also preferred. Taking up live insects released from reservoirs above the live insect receiving zone of the insect transport device in the laminar flow of gas wherein the gas is air, preferably temperature controlled air and/or relative air humidity controlled air, provides a measure to further contribute to maintaining the transported live insects in good health, and uninjured, since temperature and relative humidity of the gas surrounding the live insects once being transported in the laminar flow of gas, are optimizable to the parameter values most suitable for preservation of health of the insects.

In one embodiment, the insects transport device is a device wherein the source of gas comprises a compressor providing compressed gas. Preferably, the compressed gas is compressed air, preferably compressed air. In one embodiment, the insects transport device, wherein the source of gas comprises a pump, for driving gas through the gas discharge member. Preferably, the source of gas comprises a pump such as a blower, for driving gas through the gas discharge member of the insect transport device, wherein the gas preferably is air.

A compressor and/or a pump provides the benefit of being able to controllable supplying the insects transport device with gas at a pressure and at a volume of gas per minute that contributes to the wellbeing of the live insects once taken up in the gas of the laminar flow. That is to say, by selecting the optimal pressure and by selecting the optimal flow rate of gas discharged from the first and optionally further gas discharge members, for example a laminar flow of gas is provided such that live insects obtain the same or similar velocity in meter per second as the gas surrounding the insects once taken up in the laminar flow of gas. Then, since gas is not passing along the live insects in the laminar flow of gas, unwanted effects of gas flowing along insects is at least reduced and eliminated at best. For example, drying out of the live insects in the laminar flow of gas is reduced or prevented, when the live insects move through the live insects transport device at the same or similar speed as the surrounding gas. For example, cooling of live insects being transported by gas passing insects is reduced or prevented as well by optimizing the pressure and gas velocity with for example a pump or with a compressor such as an air compressor. Typically, the air flow exiting the insects transport device, and carrying the live insects, has a velocity of 6.0-11.0 m/sec, such as 7.0-9.0 m/sec. Typically, gas blown over the gas guiding unit(s) such that a laminar gas current is provided over the smooth-surfaced gas guiding unit(s), has a pressure of 0.05-0.08 bar when exiting the gas discharge member(s).

In one embodiment, the insects transport device is a device wherein the gas is temperature-controlled gas and/or wherein the gas is a relative humidity-controlled gas. Typically, the compressor or pump provides a gas such as air which is discharged by the first and optionally further gas discharge member(s) at a speed of between 1 m/sec and 100 m/sec, such as between 5 m/sec and 40 m/sec, preferably about 10-30 m/sec such as about 25 m/sec, according to the invention, such that a laminar flow of gas is provided in the insects transport device, having gas flowing at the same or similar velocity. Typically, the compressor or pump provides an amount of gas such as air at a volume of 10 $m^3$/hour to 320 $m^3$/hour, preferably about 20 $m^3$/hour to 60 $m^3$/hour, driven through the first and further gas discharge members such that a laminar flow of gas is provided having the same or similar flow rate of 1 $m^3$/hour to 30 $m^3$/hour, preferably about 5 $m^3$/hour to 15 $m^3$/hour. In one embodiment, the insect transport device comprises a compressor or pump configured to provide an amount of gas such as air at a volume of 2.5 $m^3$/hour to 1000 $m^3$/hour, preferably about 5 $m^3$/hour to 500 $m^3$/hour, more preferably of 10 $m^3$/hour to 320 $m^3$/hour, most preferably of about 20 $m^3$/hour to 60 $m^3$/hour, driven through the first and further gas discharge members such that a laminar flow of gas is provided having the same or similar flow rate of 0.2 $m^3$/hour to 70 $m^3$/hour, preferably about 0.5 $m^3$/hour to 50 $m^3$/hour, more preferably of 1 $m^3$/hour to 30 $m^3$/hour, most preferably of about 5 $m^3$/hour to 15 $m^3$/hour. These flow velocities and these flow rates are preferred since they contribute to optimally keeping the transported live insects in the insects transport device in good condition. In addition, these flow velocities and these flow rates are preferred since they contribute to optimally keeping the transported live insects airborne in the insects transport device while being transported through the device, such that the live insects are not contacting any surface of the device and are not hurt or damaged accordingly.

In one embodiment, the insects transport device is a device wherein the feeder arrangement is configured to receive at least one reservoir for live insects at a predetermined distance above said live insects receiving portion of the top surface of the at least one gas guiding member. Preferably, said predetermined distance between the at least one reservoir and the live insects receiving portion is between 3 cm and 35 cm, such as between 5 cm and 20 cm, preferably about 4 cm or about 6-9 cm.

Optimization of the distance between the reservoir and the insects receiving portion contributes to the efficiency of the process of taking insects up in the laminar flow of gas in the insects transport device. Optimization in this regard is providing the reservoir at a height above the laminar flow of gas such that most if not all of the live insects released from the reservoir are taken up by the laminar flow of gas, with minimal or no losses of live insects due to for example turbulent air streams, etc.

In one embodiment, the insects transport device is a device wherein at least the smooth top surface of the at least one gas guiding member is made of any of stainless steel, aluminum, a polymer such as polypropylene and polyethylene, a polymer blend, or a combination thereof. A smooth top surface in the context of the invention refers to the top surface of the gas guiding members being free of ridges, protrusions, recesses, etc., wherein the top surface is for example preferably polished or the like in order to provide for a surface which minimally hampers the laminar flow of gas through the insects transport device, therewith preventing turbulence for example. The inventors found that a surface that is smooth does not prevent neonate larvae such as those from black soldier fly from sticking to such surface. That is to say, blowing a stream of air along the polished and smooth surface of e.g. a metal such as aluminum or stainless steel, with e.g. neonate larvae on top of said smooth surface, was not efficient and efficacious in transporting said larvae along the surface, according to tests performed by the inventors. Therefore, the inventors found that it is beneficial to keep the live insects airborne in the laminar flow of gas in the insect transport device of the invention. Thus, a polished and smooth top surface of the gas guiding unit aids the unhampered laminar flow of e.g. air, and further contributes to the ease of cleaning the insects transport device.

In one embodiment, the insects transport device is a device wherein the tilt angle $\alpha$ is between 0° and 45°. Preferably, the tilt angle $\alpha$ is between 10° and 30°. Tilting the insects transport device is in support of controlling the numbers of transported live insects exiting the transport device of the invention. For example, operating a high speed camera at the proximal end of the gas guiding unit for, for example, counting the number of exiting transported live insects, is aided by providing a tilted insects transport device at an angle as indicated, such as 15° to 25° or about 20°. Tilting the insects transport device this way provides for the possibility to position a camera above the exiting live insects while also being able to position a lamp required for proper operation of the camera below the location where live insects exit the insects transport device, with a reduced risk or even without the risk for exiting transported live insects contaminating the lamp surface. In a preferred embodiment, the tilt angle $\alpha$ is 0°. Then, for example contamination of the high speed camera at the position where live insects exit the insects transport device, is prevented by for example positioning the camera aside the exiting stream of live insects, instead of underneath the stream of insects.

In one embodiment, the insects transport device is a device further comprising a live insect discharge member comprising a flat surface with a first end and a second end, the discharge member coupled with its first end to the proximal end of the gas guiding unit. Providing the insect transport device with such live insect discharge member has the benefit of providing the possibility to improve on directing the transported live insects while exiting the transport device. For example, such a live insect discharge member is a funnel ending at the proximal end with a smaller cross section than the cross section of the opening of the insect transport device at the location of the proximal end of the gas guiding member.

In one embodiment, the insects transport device is said insects transport device further comprising a live insects counting device for counting live insects in the first laminar flow exiting the insect transport device at the proximal end of the live insect discharge unit. Preferably the counting device is an electronic device such as a camera for counting live insects in the first laminar flow exiting the insect transport device at the proximal end of the live insect discharge unit.

In one embodiment, the insects transport device is the insects transport device wherein the counting device is a high-speed camera. Preferred is a high-speed camera such as a 9 kHz camera although various other high speed cameras having an imaging speed of between 2 kHz and 25 kHz are equally applicable. One of the many advantages of the insect transport device is the provision of a relatively narrow stream of gas comprising the transported fully airborne live insects such as neonate larvae or mites exiting the insects transport device via a funnel-shaped live insects discharge member, such that for example the live insects can be imaged and monitored in a relatively small surface area comprising a relatively high number of live insects per unit volume or unit area. For example, now a camera with a relatively smaller width is still applicable for imaging purposes, compared to a camera with a broader width, required to image live insects passing the camera while exiting the insects transport device in a relatively broad and non-funneled laminar flow of gas. Cost saving is then one of the advantages.

In one embodiment, the insects transport device is a device wherein the reservoir for live insects is an insect egg collection interface or an insect egg holder, i.e. an ovisite. According to the invention, an insects transport device comprises as the reservoir for live insects an ovisite such as a honey comb. In one embodiment, the insects transport device is a device wherein the reservoir for live insects is an insect receptacle or an insect rearing container, i.e. a cage. According to the invention, an insects transport device comprises as the reservoir for live insects a cage provided with a perforated bottom floor such as a container with side walls and a bottom floor comprising or consisting of a mesh or sieve or plate with pores, the mesh, sieve openings or pores having a cross-sectional size and shape suitable for passing of live insects, arthropods in general, such as for example mites.

In one embodiment, the insects transport device is a device wherein the feeder arrangement is configured to receive between 2 and 250 reservoirs, preferably between 10 and 100, more preferably about 32 or about 64 reservoirs for releasing live insects above the live insects receiving portion.

In one embodiment, the insects transport device is arranged to transport any one or more of insects, insect larvae, insect eggs, insect prepupae and insect pupae. Preferably, the insects transport device is arranged to transport any one or more of insects, insect larvae, insect eggs, insect prepupae and insect pupae, wherein the insects, insect larvae, insect eggs, insect prepupae and insect pupae are live insects, live insect larvae, live insect eggs, live insect prepupae and live insect pupae. Preferably the live insects transported by the insects transport device are live insect larvae of black soldier fly, more preferably live neonate larvae of black soldier fly. Preferably the live insects, more in general the arthropods, transported by the insects transport device are live mites.

In one embodiment, the insects transport device is arranged to transport live insects.

In one embodiment, the insects transport device is arranged to transport live neonate insect larvae.

In one embodiment, the insects transport device is arranged to transport live black soldier flies.

In one embodiment, the insects transport device is arranged to transport live mites.

In one embodiment, the insects transport device is a device wherein the feeder arrangement is configured to receive the at least one reservoir in a predetermined orientation relative to the direction of the path for the first laminar flow of gas, such that a major surface of the reservoir(s) is oriented perpendicular to the direction of said first laminar flow of gas. Positioning reservoirs which have a major surface this way contributes to avoiding occurrence of any turbulence at the location of the reservoirs, at the location of the live insect receiving portion, therein between, and alongside the laminar flow of gas. In one embodiment, the insects transport device is a device wherein the feeder arrangement is configured to receive the at least one reservoir in a predetermined orientation relative to the direction of the path for the first laminar flow of gas, such that a major surface of the reservoir(s) is oriented parallel to the direction of said first laminar flow of gas. Positioning reservoirs which have a major surface this way contributes to avoiding occurrence of any turbulence at the location of the reservoirs, at the location of the live insect receiving portion, therein between, and alongside the laminar flow of gas. It will be appreciated that limiting any disturbing influence of turbulent air around live insects on their way from the reservoir to the live insects receiving portion, and while taken up and transported by the laminar flow of gas, contributes to increasing the efficiency of the transport with regard to the numbers of successfully transported live insects by the insect transport device, while in operation.

In one embodiment, the insects transport device is a device wherein the live insects receiving portion further comprises side walls located along longitudinal sides of the at least one longitudinal gas guiding member, the side walls being tilted at an obtuse angle relative to the top surface of the at least one gas guiding member, wherein each side wall having a top side and a bottom side, the bottom side being connected to a longitudinal side of the at least one longitudinal gas guiding member, and a smooth surface arranged between the bottom side and the top side, and wherein the top side of each side wall is provided with at least a second gas discharge member, each second gas discharge member being located at the top side of each side wall and comprising a connector configured to connect the second gas discharge member to a source of gas, for providing a second laminar flow of gas over the surface of the side walls from the top side of the side walls to the path of the first laminar flow of gas during operation of the transport device, and wherein the second laminar flow of gas is oriented perpendicular to the first laminar flow of gas.

Providing the insects transport device with a live insects receiving portion further comprising the indicated side walls contributes to improved capacity of the transport device when the duration of operation at constant supply of a certain number of transported live insects exiting the insects transport device is taken into account, and/or when the numbers of live insects exiting the insects transport device per time unit is taken into account. With such side walls tilted at an obtuse angle relative to the top surface of the at least one gas guiding member, the capacity of the feeder arrangement is enlarged while the laminar flow of gas is kept at the same size and volume and flow rate. The second laminar flow of gas, preferably air, is directed perpendicular to the direction of the first laminar flow of gas, and the flow rate and/or the pressure at which the gas exits the second gas discharge member for building up the second laminar flow of gas, is/are lower than those for the first laminar flow of gas running from the distal end of the gas guiding member to the proximal end thereof. These differences in flow rate and/or gas pressure contribute to the reduction or even to the avoidance of undesired turbulence anywhere in the proximity of live insects, such as inside the cases live insects transport device of the invention.

An embodiment is the insects transport device according to the invention, wherein the live insects receiving portion further comprises convex side walls located along longitudinal sides of the at least one longitudinal gas guiding member, wherein each convex side wall has a top side and a bottom side and a smooth convex surface arranged between the top and bottom side, the bottom side being connected to a longitudinal side of the at least one gas guiding member, and wherein the top side of each convex side wall is provided with a second gas discharge member comprising a connector configured to connect the second gas discharge member to a source of gas for providing a second laminar flow of gas over the surface of the convex side wall from the top side thereof to the at least one gas guiding member during operation of the insect larvae transport device. The inventors observed that by application of such convex surfaces of the side walls, air turbulence is largely avoided in the interior side of the casing and above and along side the gas guiding member(s), and by controlling the air velocity, air turbulence in the casing and surrounding the feeder arrangement and the gas guiding unit(s) is even absent. Thus, for some embodiments, application of convex curved side walls comprised by the live insects receiving portion are preferred.

An embodiment is the insects transport device according to the invention, wherein the live insects receiving portion further comprises flat side walls located along longitudinal sides of the at least one longitudinal gas guiding member, wherein each flat side wall has a top side and a bottom side and a smooth flat surface arranged between the top and bottom side, the bottom side being connected to a longitudinal side of the at least one gas guiding member, and wherein the top side of each flat side wall is provided with a second gas discharge member comprising a connector configured to connect the second gas discharge member to a source of gas for providing a second laminar flow of gas over the surface of the flat side wall from the top side thereof to the at least one gas guiding member during operation of the insect larvae transport device. The inventors observed that by application of such flat surfaces of the side walls, the air velocity of the air flowing top-down over the flat surface of the side walls is more constant and/or better controllable, compared to more decreasing air velocity of air flowing top-down over the surface of convex side walls. Thus, in some embodiments, application of flat curved side walls comprised by the live insects receiving portion are preferred.

An embodiment is the insects transport device according to the invention, further comprising a cover member extending along and above the at least one gas guiding member at a clearance distance with respect thereto. The inventors determined that presence of such a cover member inside the casing of the insects transport device aids in minimizing the risk for the occurrence of air turbulence in between the bottom side of the reservoir(s) and the top side of the gas guiding member(s), and in the proximity of the laminar flow of gas. Herewith, during operation of the insects transport device, transport of live insects is not influenced or hampered by turbulent air.

An embodiment is the insects transport device according to the invention, wherein the cover member comprises a plurality of cover side walls, wherein each cover side wall extends in upward and longitudinal/lengthwise direction along one of the convex side walls.

An embodiment is the insects transport device according to the invention, wherein the cover member further comprises a sloped roof.

The inventors determined that presence of such a cover member inside the casing of the insects transport device aids in minimizing the risk for the occurrence of air turbulence in between the bottom side of the reservoir(s) and the top side of the gas guiding member(s), and in the proximity of the laminar flow of gas. Herewith, during operation of the insects transport device, transport of live insects is not influenced or hampered by turbulent air.

An embodiment is the insects transport device according to the invention, wherein the casing covering the gas guiding unit and the feeder arrangement comprises a top wall and side walls defining a closed inner volume V in which the at least one reservoir is arranged, and wherein the insects transport device comprises an air feed channel comprising tube and connector connected to the top wall through opening, further comprising gas temperature controller and absolute air humidity control unit, configured to provide air of a controllable and desired temperature and/or controllable and desired relative humidity to the inner volume V of the casing. This way, it is possible to provide a temperature controlled and relative air humidity controlled air along side and over reservoirs positioned in the feeder arrangement, wherein the air temperature and the relative air humidity are optimized for stimulating or delaying hatching of eggs or movement of live insects towards the direction of the laminar air flow, as the case may be. Moreover, separating the source of gas that is provided through the first and further gas discharge member(s) for provision of the laminar flow of air, from the source of gas that is applicable for a flow of air towards and over and along the reservoirs, allows for optimization of the temperature and the relative humidity of the air for both sources of gas. The inventors found that for stimulating hatching of insect eggs, a higher relative humidity of the air is beneficial, compared to the relative humidity of the air that is optimal for the air applied for the provision of the laminar flow of air. Hatching of eggs benefits from a relative humidity of the air of 75%-95% at 25°–35° C. However, applying such humid air for the laminar flow of air would introduce a risk for condensation of water vapor at surfaces inside the casing of the insects transport device, when temperature may drop, or in connectors, tubings, etc., e.g. downstream of the proximal end of the gas guiding unit(s). Therefore, the inventors established that the risk for condensation of water vapor comprised by the laminar flow of gas is limited when the first gas discharge member provides air at a temperature of 25°–35° C. and a relative humidity of the air of 45%-65%, for establishing the laminar flow of air.

An embodiment is the insects transport device according to the invention, wherein the casing further comprises a secondary top wall arranged below the top wall at a wall distance Dw therefrom defining a cavity space between the top wall and the secondary top wall, wherein the secondary top wall further comprises one or more slits fluidly connecting the cavity space and the inner volume V of the casing. Providing conditioned air through such slits, over and along side the reservoirs positioned thereunder, contributes to the avoidance of air turbulence inside the casing and in the proximity of the path of the freely falling live insects from the reservoir in the direction of the laminar air flow underneath the reservoirs.

An embodiment is the insects transport device according to the invention, wherein the inner side of top wall or, if present, the inner side of secondary top wall is provided with a light source and/or a heater positioned above the feeder arrangement, such that reservoirs positioned in the feeder arrangement are irradiable with light by the light source from above the reservoirs and/or heatable with the heater from above the reservoirs during operation of the insects transport device. The insects transport device is suitable for receiving reservoirs which are cages comprising live insects, more in general, live arthropods, such as live mites. Such cages are provided with a bottom floor comprising openings for passage of mites downward, said openings provided by for example a mesh, sieve, net, protrusions, through holes, slits, etc. Owing to negative phototaxis and/or negative thermotaxis, mites in the cage migrate downward to the bottom floor of the cage upon irradiation with light by the light source and/or upon heating by application of the heater, when the insects transport device is in operation. Then, the mites escape the cage through the openings in the bottom floor of the cage and in a gravity-driven free fall the mites are taken up by the laminar flow of air under the live insects receiving portion of the gas guiding member.

An embodiment is the insects transport device according to the invention, wherein the live insect discharge member comprises a throat portion arranged between the first end and the second end of the live insect discharge member, wherein a discharge channel extends between the first end and the second end and comprises a constricted channel portion at the throat portion, and wherein the throat portion is provided with a slit shaped through hole laterally extending through the throat portion.

An embodiment is the insects transport device according to the invention, wherein the constricted channel portion comprises a rectangular cross section.

An embodiment is the insects transport device according to the invention, wherein the slit shaped through hole has a length of at least 90% percent of a width of the constricted channel portion in a direction of the slit shaped through hole.

An embodiment is the insects transport device according to the invention, wherein the slit shaped through hole comprises a chamfered or rounded downstream inner edge.

Provision of the live insect discharge member comprised by the insects transport device with such a throat portion allows for directing and condensing and narrowing the stream of live insects exiting the insects transport device in the exiting laminar flow of air. The slit allows for application of the venture principle while at the same time the opening provided by the slit provides the possibility to monitor the number of exiting live insects per unit of volume or per unit of time, by application of a camera such as a high-speed camera. The camera images the passing live insects at the position of the slit shaped through hole. A light source aiding the imaging is optionally positioned at the opposite side of the slit shaped through hole.

An embodiment is the insects transport device according to the invention, wherein the second end of the live insect discharge member is provided with an air amplifier unit which is configured to inject further air $A_f$ into the second end.

An embodiment is the insects transport device according to the invention, wherein the second end of the live insect discharge member is provided with a tube connected at the proximal end of the tube to the second end of the live insect discharge member and connected at the distal end of the tube to an air amplifier unit which is configured to inject further air $A_f$ into the distal end of the tube.

Provision of the second end of the live insect discharge member, either or not via a connecting tube, with an air amplifier unit provides the opportunity for transporting the live insects over an enlarged distance, while during said transport the air velocity and air pressure is maintainable at a constant and controllable speed and pressure, and can be kept constant during the transport.

An embodiment is the insects transport device according to the invention, wherein the insects transport device comprises a cyclone separation system. An embodiment is the insects transport device according to the invention, wherein the second end of the live insect discharge member is in fluid connection with a cyclone separation system comprising a main cyclone chamber having a top chamber part and a conical shaped bottom chamber part, wherein the top chamber part is connected to one or more intake channels each of which is arranged for fluid connection to the second end of the live insect discharge member of an insects transport device, and wherein the bottom chamber part is connected to a discharge nozzle comprising a discharge end having a main discharge conduit for discharging live insects from the cyclone separation system, and wherein the discharge end comprises an air injection member for connection to a secondary air source and wherein the air injection member is configured to inject air back into the discharge nozzle.

An embodiment is the insects transport device according to the invention, wherein the cyclone separation system comprises a (further) counting device arranged next to the discharge nozzle for counting the number of live insects being discharged therefrom.

An embodiment is the insects transport device according to the invention, wherein the cyclone separation system comprises a top portion of the cyclone separation system comprising openable slats with pivots and slat operation driver unit for moving the slats from an open state to a closed state and vice versa. Provision of a cyclone separation system connected to the second end of the live insect discharge member further aids in accurate dosing, batch wise dosing, and in controlling and establishing the number of dosable live insects at the desired level suitable and required for efficient insect farming, packaging, etc.

The inventors established that incorporating in the insects transport device a cyclone separation system by fluidly connecting said cyclone separation system to the live insect discharge member of the insects transport device, further improves the capability to count and dose live insects exiting the reservoirs and transported by the laminar flow of gas. For example, the insects transport device comprising the cyclone separation system allows for stop-flow dosing of live insects, beneficial for example for batch wise provision of crates comprising insect fed substrate with a predetermined and controllable number of live insects such as neonate larvae of black soldier fly. For example, the insects transport device comprising the cyclone separation system allows for stop-flow dosing of live insects such as mites, beneficial for example for batch wise provision of a predetermined and controllable number of live insects per unit dose. Furthermore, providing the cyclone separation system comprised by the insects transport device with controllable openable slats in the top portion, provides the possibility to adjust the air pressure inside the cyclone separation system independent from the constant and continuously flowing air current exiting the live insects discharge member and entering the cyclone separation system.

An aspect of the invention relates to a method for transporting live neonate insect larvae comprising the steps of:

- providing an ovisite comprising insect eggs;
- providing a live insects transport device of any one of the here above aforementioned aspects and embodiments;
- providing a laminar flow of air in the insects transport device;
- placing said ovisite in a feeder arrangement of said insects transport device; and
- transport live neonate insect larvae upon hatching of said larvae in the ovisite by taking up the neonate insect larvae in the first laminar flow of air.

An aspect of the invention relates to the use of the insects transport device of the invention for dosing live neonate insect larvae, wherein live neonate insect larvae transported by said insects transport device are collected at the proximal end of the gas guiding unit comprised by the insects transport device or at the second end of the insect discharge member comprised by the insects transport device, in a first receptacle for a period of time until a predetermined number of live neonate insect larvae passed said proximal end of the gas guiding unit or said second end of the insect discharge member, such that a dose of live neonate insect larvae is provided.

In one embodiment, use of the insects transport device, is the use of the device wherein the predetermined number of live neonate insect larvae is established by a counting device for counting live insects in the first laminar flow exiting the live insect transport device.

In one embodiment, the method or the use, are applied with black soldier flies.

In one embodiment, the method or the use are applied with air in the first laminar flow which is temperature controlled air at a temperature of between 22° C. and 30° C. Preferred is a temperature of about 25° C. to 28° C.

In one embodiment, the method or the use, are applied with the air in the first laminar flow being relative-humidity controlled air with a relative humidity of between 40% and 90%, such as about 60% to 75%.

In one embodiment, the method or the use are applied with the air in the first laminar flow having a speed of between 10 m/sec and 70 m/sec.

In one embodiment, the method or the use are applied with the air in the first laminar flow having a pressure at the location of the gas discharge member of between 10 bar and 0.8 bar.

In yet a further aspect, the present invention relates to a combination of a cyclone separation system and one or more insects larvae transport devices connected to the cyclone separation system, wherein the cyclone separation system comprises a main cyclone chamber having a top chamber part and a conical shaped bottom chamber part, wherein the top chamber part is connected to one or more intake channels each of which is arranged for connection to an insects transport device of the one or more insects larvae transport devices, and

- wherein the bottom chamber part is connected to a discharge nozzle comprising a discharge end having a main discharge conduit for discharging live insects from the cyclone separation system, and
- wherein the discharge end comprises an air injection member for connection to a secondary air source and wherein the air injection member is configured to inject air back into the discharge nozzle.

An aspect of the invention relates to a method for transporting live insects such as live neonate insect larvae or live mites comprising the steps of: providing an ovisite comprising insect eggs or providing a cage with a bottom floor with openings and comprising mites; providing an insects transport device of the invention; providing a laminar flow of air in the insects transport device; placing said ovisite or said cage in the feeder arrangement of said insects transport device; providing a temperature-controlled and relative air humidity controlled air current over and along the ovisites perpendicular to the laminar flow of air according to the invention, or providing light and/or heat from a direction above the mite cage opposite to the bottom floor side of the cage according to the invention, and transport live neonate insect larvae upon hatching of said larvae in the ovisite, or transport live mites upon escape of the cage through the bottom floor openings driven by the light and/or heat, by taking up the neonate insect larvae or the mites in the first laminar flow of air.

An aspect of the invention relates to use of the insects transport device of any one of the here above aforementioned embodiments for dosing live insects such as neonate insect larvae or live mites, wherein live neonate insect larvae or live mites transported by said insects transport device are collected at the proximal end of the gas guiding unit comprised by the insects transport device or at the second end of the insect discharge member comprised by the insects transport device, in a first receptacle for a period of time until a predetermined number of live neonate insect larvae or live mites passed said proximal end of the gas guiding unit or said second end of the insect discharge member, such that a dose of live neonate insect larvae or a dose of live mites is provided.

An embodiment is the use according to the invention, wherein the predetermined number of live neonate insect larvae or live mites is established by a counting device for counting live insects in the first laminar flow exiting the insects transport device.

An embodiment is the method according to the invention or the use according to the invention, wherein the insect larvae are black soldier fly larvae, for example between 2 seconds and 20 minutes post-hatching, preferably 10 seconds-15 minutes post-hatching, more preferably 30 seconds-7 minutes post-hatching.

An embodiment is the method according to the invention or the use according to the invention, wherein the air in the first laminar flow is temperature controlled air at a temperature of between 22° C. and 30° C., such as 26° C.-30° C.

An embodiment is the method according to the invention or the use according to the invention, wherein the air in the first laminar flow is relative-humidity controlled air with a relative humidity of between 45%-65% such as about 55%.

An embodiment is the method according to the invention or the use according to the invention, wherein the air in the first laminar flow has a speed of at least 1 m/sec, preferably between 10 m/sec and 70 m/sec.

An embodiment is the method according to the invention or the use according to the invention, wherein the air in the first laminar flow has a pressure at the location of the gas discharge member of between 10 bar and 0.8 bar.

An embodiment is the method according to the invention or the use according to the invention, wherein the air provided by the air feed channel is temperature controlled air at a temperature of between 25° C. and 35° C., such as 26° C.-30° C.

An embodiment is the method according to the invention or the use according to the invention, wherein the air provided by the air feed channel is relative-humidity controlled air with a relative humidity of between 75% and 95%, preferably 45%-65% such as about 85%.

An aspect of the invention relates to a single dose of insects obtained with or obtainable with the method of the invention.

An embodiment is the single dose of insects obtained with or obtainable with the method of the invention, wherein the insects are living black soldier fly neonate larvae, preferably with any larvae-to-larvae age difference post-hatching of less than 2 hours, when the individual insects in the single dose are considered, such as between 6 seconds and 12 minutes.

Definitions

The term "live" has its regular scientific meaning and here refers to an organism that is in a healthy condition and that has a normal average life expectation.

The term "transport" has its regular scientific meaning and here refers to taking an item, here in the context of the invention an insect such as live neonate insect larvae, from a first location to a second location with the help of a transportation means, here a fluid such as a gas.

The term "air" has its regular scientific meaning and here refers to the air surrounding the earth at ground level.

The term "ambient" has its regular scientific meaning and here refers to that what is surrounding something. Ambient air thus refers to the air surrounding the live insects transport device, according to the invention.

The term "insect" has its regular scientific meaning and here refers to all stages of an insect, e.g. pupae, adult insect, neonate larvae, larvae, prepupae. Moreover, for the sake of conciseness, the term insect also relates to arthropods in general, including flies such as black soldier fly, and including mites, unless stated otherwise or when it is clear from the context that the regular scientific meaning is referred to. The term insects in the context of the invention may refer to arthropods, mites, flies, and to Lacewings (e.g. *Chrysoperla carnea*), Coccinelid beetles (e.g. Cryptolaemus *montrouzieri*), any species of predatory bugs (e.g. *Macrolophus pygmaeus*), other insects, such as pollinators (e.g. the onion fly, *Delia antiqua*) and any species of predatory beetles (e.g. the greenhouse rove beetle, *Dalotia coriaria*), as well as terrestric fly species.

The term "high-speed" has its regular scientific meaning and here refers to a speed of acquiring images of at least 30 per second to 20.000 per second such as about 15.000 images per second. For example high-speed imaging is imaging with exposures of less than 1/1.000 second or frame rates in excess of 250 frames per second in the context of the invention.

The term "longitudinal" has its regular scientific meaning and here refers to the direction running from the distal end of the gas guiding units and the distal gas guiding members in the direction of the proximal end of the gas guiding units and the proximal gas guiding members, of the live insect transport device of the invention.

The term "imbricatedly" or "imbricated" has its regular scientific meaning and here refers to the arrangement of essentially planar bodies such that they stack in a consistent fashion.

The term "casing" has its regular scientific meaning and here refers to an enclosure enclosing here (most of) the parts and components of the insects transport device of the invention.

The term "reservoir" has its regular scientific meaning and here refers to a receptacle, e.g. a container, a tray, a funnel, a sieve, a cup, etc., such as an ovisite or a tray comprising a bottom floor comprising a mesh or sieve or through holes, with at least an open side for allowing live insects exiting the reservoir and subsequently moving in the direction of the live insect receiving portion between the distal end and proximal end of the at least one gas guiding member of the insect transport device of the invention.

BRIEF DESCRIPTION OF THE DRAWINGS

FIG. 20A shows a schematic view of an insects transport device 100 further provided with a cyclone separation system 148 connected to the live insect discharge member 11, according to an embodiment of the present invention. An air amplifier 142' is connected with the live insect discharge member 11 proximate to the proximal end 121" of the gas guiding unit 112;

FIG. 20B and the exploded view of part of FIG. 20B, FIG. 20C, show a schematic view of an insects transport device 100 further provided with a cyclone separation system 148 connected to the live insect discharge member 11, according to a further embodiment of the present invention. Now, an air amplifier 142' is connected with a tube 11b, the tube 11b connected to an insect discharge member 11', 11, 11a, therewith physically separating the air amplifier 142' from the insect discharge member 11', 11, 11a with the tube 11b;

DETAILED DESCRIPTION OF EMBODIMENTS

Figure 1A:
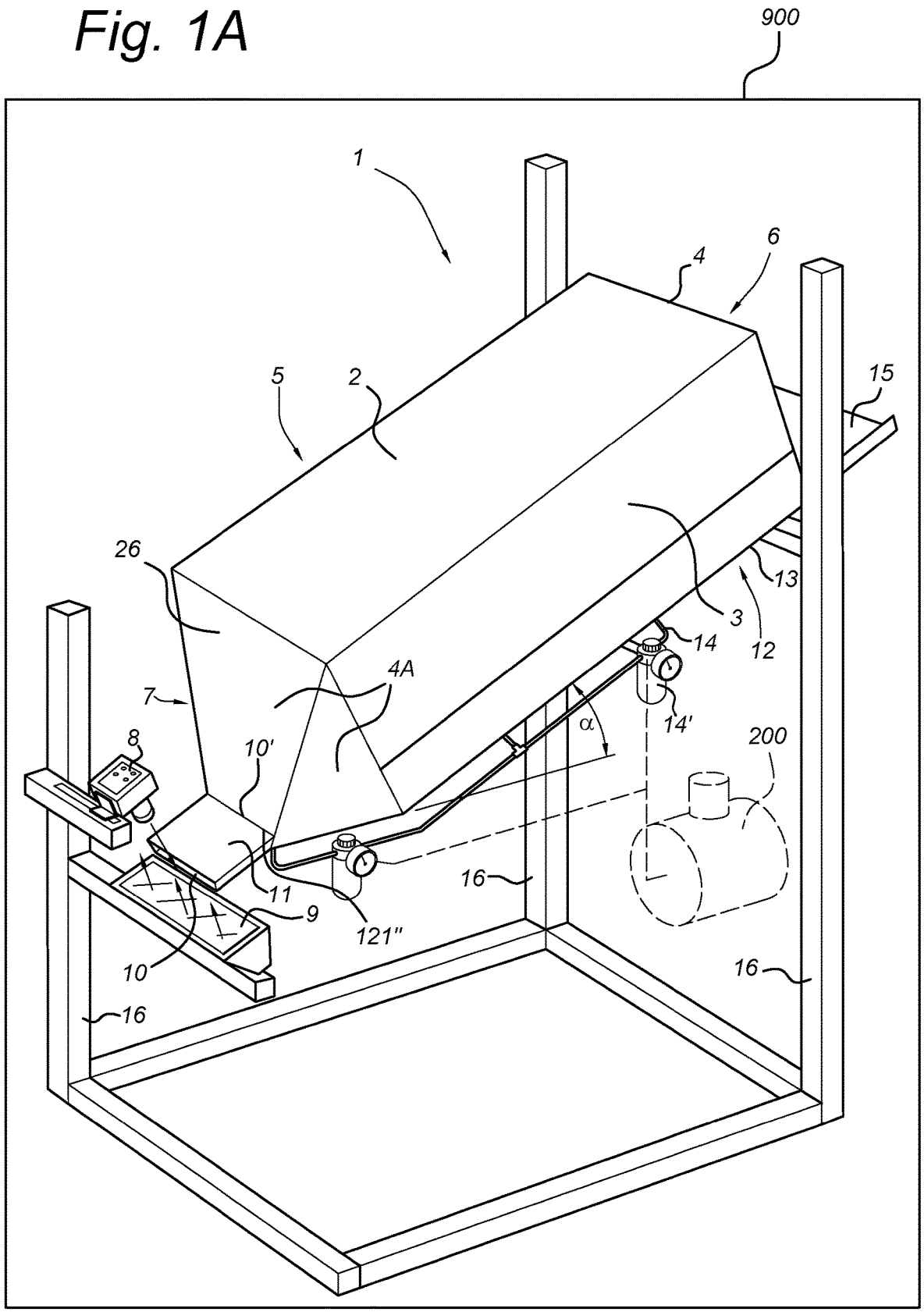
FIG. 1 displays an overview of an embodiment of the invention, showing an insects transport device 1. The insects transport device is tilted relative to the horizontal over an angle α (alpha). Further, an insect discharge member 11 is indicated, provided with a camera 8 and a lamp 9.

Referring to FIG. 1, an overview of an embodiment of the invention is provided, showing a live insects transport device 1. Optionally, the insects transport device is positioned inside an air-conditioned volume 900 such as a climate room 900

4", for providing access to the interior of the insects transport device, for example for delivery of a reservoir or for removal of an empty reservoir after operation of the insects transport device. The top wall and side wall of the casing 5 are for example thermally insulated walls, provided with a layer of thermally insulating material, such that the volume defined by the casing and the gas guiding unit(s) inside the insects transport device is thermally insulated.

Now referring to FIG. 3, a drawing is displayed providing a detailed side view of an insects transport device 1 where the proximal end 26 of the gas guiding unit 12' ends and where the insect discharge member (See also 11 in FIG. 2) is located and coupled to said proximal end with the distal end portion 10' of the live insects discharge member. The live insects discharge member has a funnel-like shape, configured to provide a narrowed stream of flowing live insects in the flow of gas exiting the insects transport device. Narrowing the stream of live insects provides the benefit of a smaller cross section of the flow of gas comprising the live insects, in support of counting, sorting and/or dosing the insects. The gas guiding member comprises upright side walls 13'. The live insect receiving zone is provided by the smooth top surface of the gas guiding member 12'.

Now referring to FIG. 4, a drawing is displayed providing an inside view of an insects transport device. Shown are longitudinal gas transport members 12', 12" which are connected imbricatedly at positions 21, 22 and 21', 22'. Where two consecutive gas transport members are coupled imbricatedly, a gas discharge member (not shown; See 20, 20' in FIGS. 2 and 114', 114", 114'" in FIG. 5) is positioned at the location where said gas transport members overlap, said gas discharge member provided with openings 23, 23' for discharging gas. In this embodiment, the live insects receiving portion is provided by the smooth top surface of four imbricatedly coupled gas guiding units, two of which are indicated with 12' and 12". The transport device has straight upright walls 13'. The laminar flow of gas is in the direction of the arrows, flowing to the proximal end 21" of the proximal gas guiding member 12'. The feeder arrangement (see 127 in FIG. 6) here received a frame 30, 30', encompassing a reservoir 128 for releasing live insects above the live insects receiving portion provided by the smooth top surface of the gas guiding unit.

Now referring to FIG. 5, a drawing is displayed providing an overview of another embodiment, showing an insects transport device 100 comprising a live insects receiving portion that is built up by a gas guiding unit 112 comprising side walls 113 tilted at an obtuse angle relative to the top surface of the gas guiding members. The insects transport device of the embodiment comprises a casing 105, said casing comprising thermally insulated side walls 103, 104 and a top side 102, the top side made at least in part from a transparent material 125 such as a plate made of glass, a transparent polymer or polymer blend, etc. The insects transport device 100 is provided with a live insects discharge member 111, coupled to the transport device at its distal end 110' at an opening 107 located at the proximal end 126 of the transport device, the live insects discharge member further comprising a proximal end where the laminar flow of gas comprising live insects exits the discharge member. The insects transport device is provided on a frame 106, 116. Gas discharge members 114', 114" and 114'" are coupled to a gas source via tubing 114, the gas source comprising a compressor unit 124 comprising a pressure control unit 140. Gas discharge members 114', 114" and 114'" are configured to provide a flow of gas for reinforcing the laminar flow of gas discharged into the insects transport member at the distal end of the gas guiding unit.

Now referring to FIG. 6, a drawing is displayed providing a view on part of a live insects receiving portion of an insects transport device 100, the live insects receiving portion being built up by a gas guiding unit 112' comprising side walls 113' and 113" tilted at an obtuse angle (13 (beta)) relative to the top surface of the gas guiding members. Further displayed are the proximal end 121" of the live insects guiding unit 112' and the further gas discharge members 131 and 131' located at the top side of the side walls, and the feeder arrangement 127 located above the live insects receiving portion of the top surface of the gas guiding unit. A first laminar flow of gas, such as a laminar flow of air, is provided in the direction of the arrows c towards the direction of the location of the proximal end 121" of the live insects guiding unit 112'. A further laminar flow of gas, yet at a lower pressure and/or at a lower velocity in $m^3$/sec, than the pressure and/or velocity of the gas in the first laminar flow, is provided in the direction of the arrows a and b, provided by the gas discharge members 131' and 131, respectively, wherein gas is discharged through openings 129' and 129, respectively. The feeder arrangement 127 received frames, encompassing a reservoir 128, 128' for releasing live insects above the live insects receiving portion provided by the smooth top surface of the gas guiding unit.

Now referring to FIG. 7, a drawing is displayed providing a view of an insects transport device 100 along the longitudinal gas guiding units in the direction towards the first gas discharge member located at opening 117 in the side wall 4, 106 of the transport device 100. Consecutive gas guiding units are connected imbricatedly and at positions where the gas guiding units overlap imbricatedly further gas discharge members are located for reinforcing the first laminar flow of gas. The live insects receiving portion is shown and is built up by a gas guiding unit 112 comprising side walls 113' and 113", e.g. flat side walls 113', 113", tilted at an obtuse angle relative to the top surface of the gas guiding members. Further displayed are the distal end of the live insects guiding unit and the further gas discharge members 131' and 131 located at the top side of the side walls 113" and 131', respectively. The gas discharge members located at positions where consecutive gas guiding members imbricatedly overlap, i.e. positions 121', 122' (i.e. overlap between the proximal end 121' of a first gas guiding member and the distal end 122' of a consecutive gas guiding member) and 121, 122 (i.e. overlap between the proximal end 121 of the second gas guiding member and the distal end 122 of a consecutive third gas guiding member), are provided with openings 123', 123 for providing the first laminar flow of gas in the direction of the arrows c. Further gas discharge members 131' and 131 are provided with openings 129' and 129, for releasing gas such that a laminar flow of gas over the surface of tilted side walls 113" and 113' is provided in the direction of the arrows, perpendicular to the direction of the first laminar flow of gas. Gas discharge members are coupled to a source of gas such as compressed air or a driver for driving air through the gas discharge members such as a pump or a fan, via tubing or pipes 114, the source of gas optionally comprising a control unit 124 for example for controlling the gas pressure at entrance of the live insect transport device and/or for controlling the velocity of the gas provided for the building up of the first and further laminar flows of gas.

FIG. 8 shows an alternative embodiment of the embodiment shown in FIG. 7 of an insect transport device 100, wherein the live insects receiving portion further comprises convex side walls 113', 113", i.e. two opposing convex side walls 113', 113", located along longitudinal sides of the at least one longitudinal gas guiding member 12', 12", 12''', e.g. three longitudinal gas guiding members 12', 12", 12''', wherein each convex side wall 113', 113" has a top side and a bottom side, and a smooth convex surface 115 arranged and extending there between, and wherein the bottom side is connected to a longitudinal side of the at least one longitudinal gas guiding member 12', 12", 12'''. As further depicted, the top side of each convex side wall 113', 113" is provided with a second gas discharge member 131, 131' comprising a connector configured to connect the second gas discharge member 131, 131' to a source of gas for providing a second laminar flow of gas over the surface 115 of the convex side wall 113', 113" from the top side thereof to the at least one gas guiding member 12', 12", 12''' during operation of the insect transport device.

Figure 7:
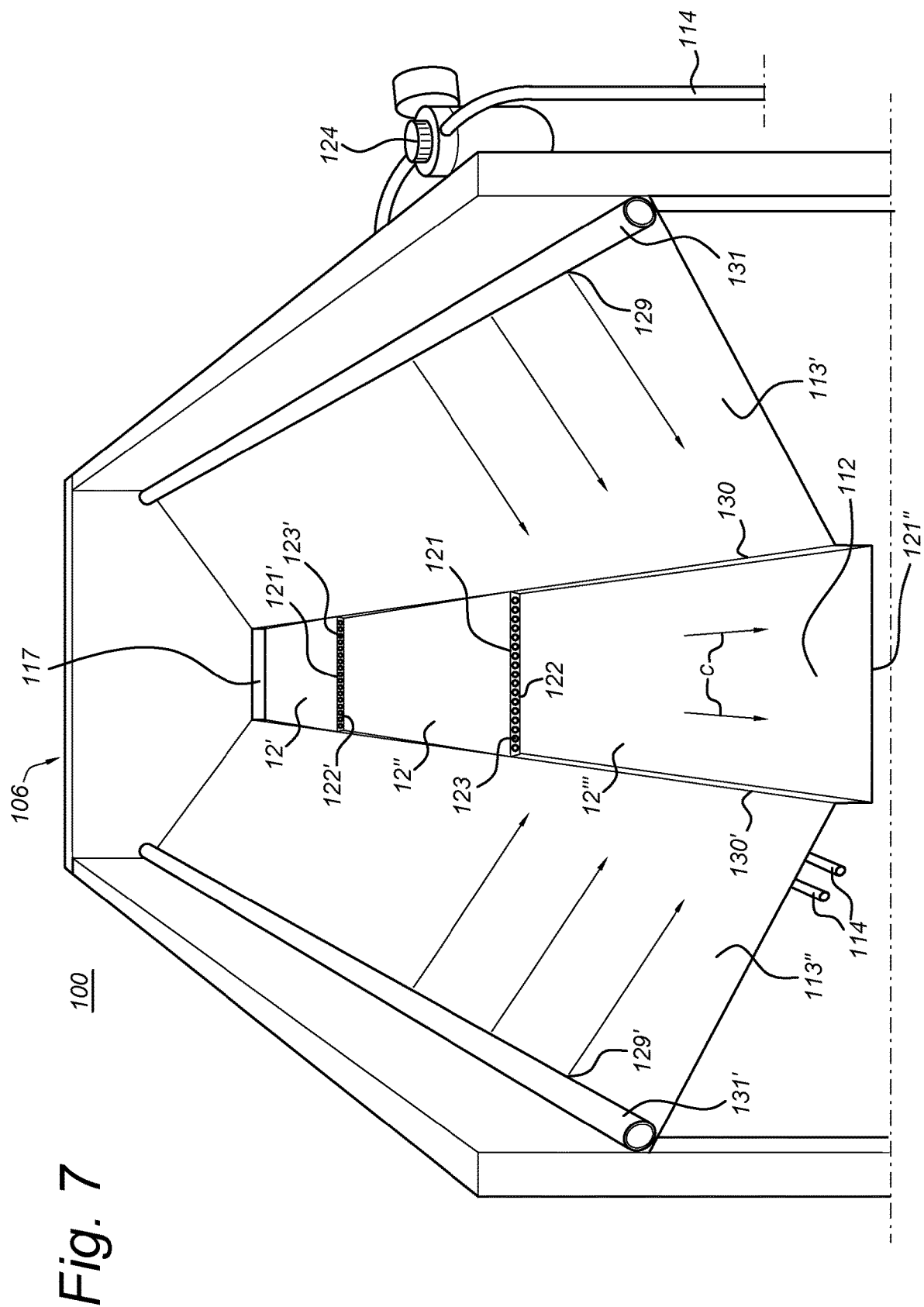
FIG. 7 displays a view of an insects transport device 100 of the invention along the longitudinal gas guiding units in the direction towards the first gas discharge member located at opening 117. Consecutive gas guiding units are connected imbricatedly and at positions where the gas guiding units overlap imbricatedly further gas discharge members are located for reinforcing the first laminar flow of gas. The live insects receiving portion is shown and is built up by a gas guiding unit 112' comprising side walls 113' and 113" tilted at an obtuse angle relative to the top surface of the gas guiding members. Further displayed are the distal end of the live insects guiding unit and the further gas discharge members 131' and 131 located at the top side of the side walls 113" and 131', respectively.
Figure 8:
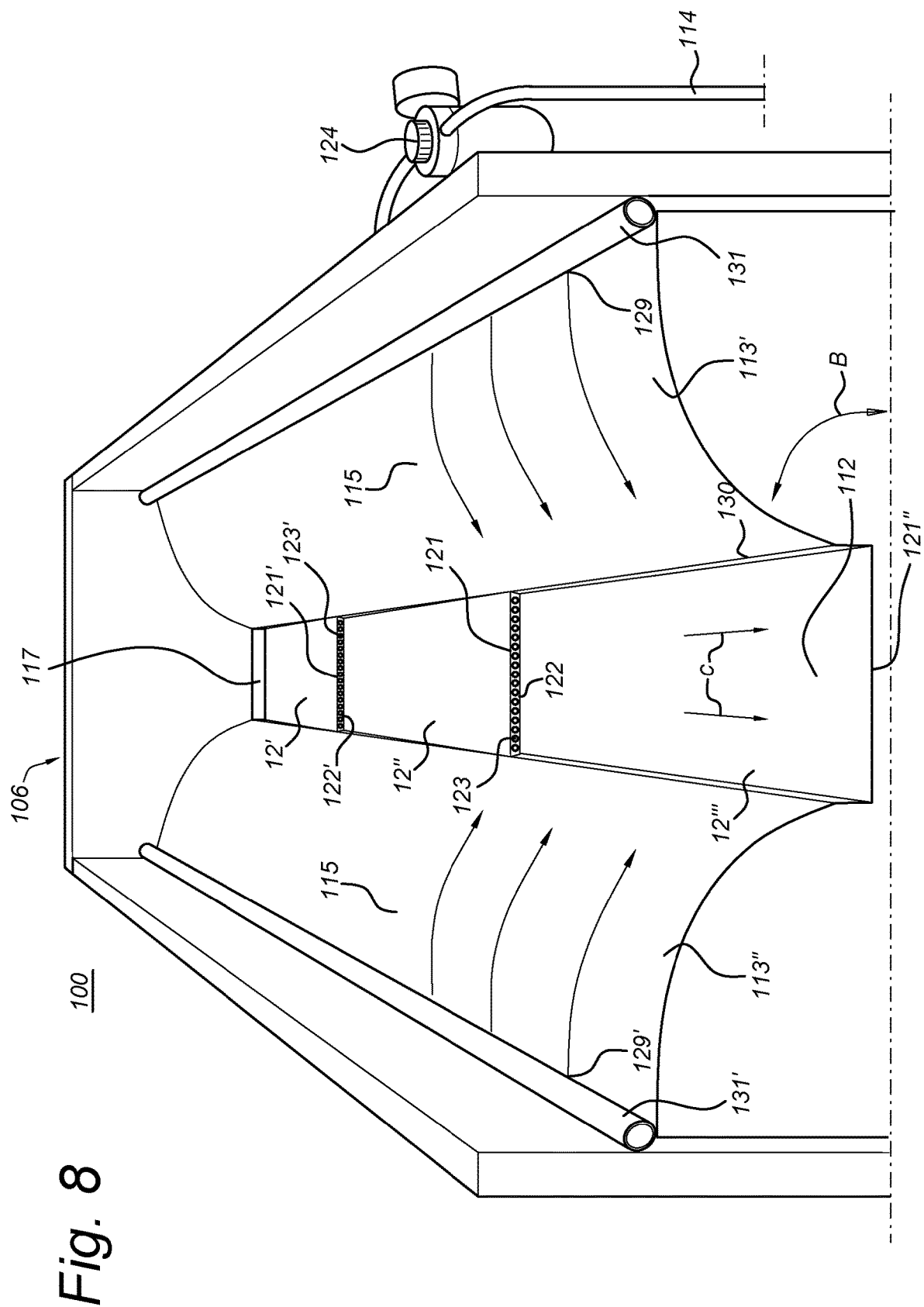
FIG. 8 depicts an insects transport device 100 comprising a gas guiding unit 112 and arched convex side walls 113', 113" arranged there along according to an embodiment of the present invention.
Figure 9:
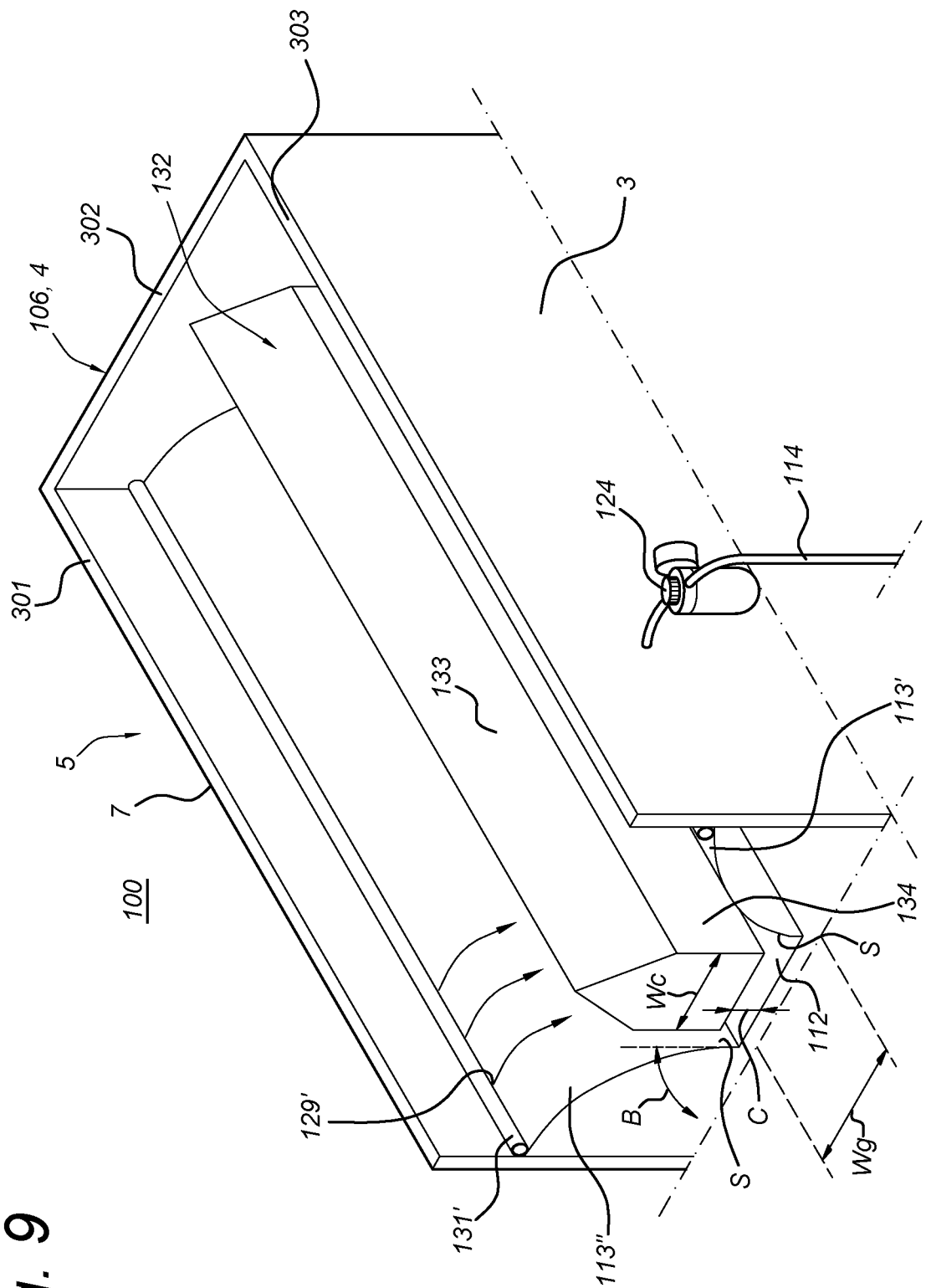
FIG. 9 depicts an insects transport device 100 comprising a cover member 132 arranged over and along a gas guiding unit 112 according to an embodiment of the present invention. The cover member 132 extends along and above the at least one gas guiding member 12', 12", 12''' at a clearance distance C with respect thereto.

In contrast to the embodiment shown in FIG. 7, in the embodiment of FIG. 8 each side wall 113', 113" is a convex side wall 113, 113" having a top side provided with a second gas discharge member 131, 131' comprising openings 129, 129' for discharging a gas, e.g. air, such that the second laminar flow of gas follows the convex surface 115 toward the at least one longitudinal gas guiding member 12', 12", 12'''.

The convex side walls 113', 113" exhibit the advantageous effect in that when gas such as air flows over the convex side walls 113', 113" toward the top surface of the at least one gas guiding member 12', 12", 12''', the speed of gas is maintained to a higher degree compared to gas flowing over flat side walls 113', 113" as shown in the embodiment of FIG. 7.

For example, when a gas such as air is discharged from the second gas discharge members 131, 131' at a speed of 4 m/sec over flat side walls 113', 113" as depicted in FIG. 7, then the air may approach the top surface of the at least one gas guiding member 12', 12", 12''' at a speed of about 2 m/s. On the other hand, for convex side walls 113', 113" as shown in FIG. 8, in order to reach 2 m/s air speed at the top surface of the at least one gas guiding member 12', 12", 12''', then air may be discharged from the second gas discharge members 131, 131' at a lower speed of e.g. 3 m/s.

In a further example, in case air is discharged from the second gas discharge members 131, 131' at a speed of about 1.2 m/sec, then the air may approach the top surface of the gas guiding members at a speed of about 0.4 m/sec, which is sufficient to maintain suspension of live insects in the first laminar flow of gas, e.g. air, over the top surface of the at least one gas guiding member 12', 12", 12''.

Therefore, gas flowing over the convex side walls 113', 113" maintains its speed to a much higher degree and a such less gas needs to be discharged by the second gas discharge members 131, 131' for facilitating laminar flow over the top surface of the at least one gas guiding member 12', 12", 12'" for transport of the live insects.

As the convex side walls 113', 113" allow for lower speeds of air being discharged from the second gas discharge members 131, 131' with minimal loss of momentum, the discharged air has less impact on e.g. environmental conditions (e.g. temperature, humidity) surrounding the reservoirs comprising the live insects. For example, when a thermally insulated casing 5 is provided covering the gas guiding unit 112 and the feeder arrangement as mentioned above, then the convex side walls 113', 113" allow air to be discharged toward the top surface of the at least one gas guiding member 12', 12", 12'" with reduced impact on environmental conditions on the inner side of the casing 5.

It is further noted that when a gas such as air flows over the convex side walls 113', 113", then the gas tends to closely follow and “stick” to the convex side walls 113', 113" in substantially laminar fashion so that turbulence is kept to a minimum. As a result, laminar flow over the convex side walls 113', 113" reduces the amount of conditioned air being disturbed or pulled away from the at least one reservoir 128, 128' (see FIG. 6) and as such the laminar flow over the convex side walls 113', 113" reduces the amount of conditioned air being disturbed or pulled away from insect eggs contained in the at least one reservoir 128, 128'.

In an embodiment, the convex side walls 113', 113" engage the top surface of the at least one gas guiding member 12', 12", 12'" at an angle (13) between 45 and 60°, such that (laminar) air flowing over the convex side walls 113', 113" causes minimum disturbance of conditioned air around insect eggs contained in the at least one reservoir 128, 128'.

For example, relative humidity of air at 1 bar around the insect eggs or around live insects such as mites may be 80-85% at a temperature of 28° C. to 35° C.+/−0.5° C. The second gas discharge members 131, 131' may then discharge a gas, e.g. air, at 1 bar at a temperature of 20° C. to 30° C. and with relative humidity of 40%-55%, e.g. 45%. As the discharged air flows in substantially laminar fashion over the convex side walls 113', 113" in a temperature controlled manner, condensation is prevented. Condensation of water vapor inside the casing 5 at any surface of the interior of the insects transport device is further prevented due to the provision of thermally insulated side walls and top wall of the casing. The inventors established that during operation of the insects transport device provided with air feed channel 5A, part of humid ‘climate’ air fed to the device by feed channel 5A, stays in the cabinet and part of the humid climate air is taken up by the laminar air flow. The volume of the humid climate air is about 20%-40% of the volume of the air building up the laminar air flow and therewith the climate air having a higher humidity than the ‘transport’ air in the laminar air flow, is sufficiently diluted in the less humid transport air, such that condensation of water vapor is prevented, for example inside the insects transport device and also when the transport air comprising a fraction of the climate air cools down to e.g. ambient temperature of 18° C.-23° C. upon exiting the insects transport device, and entering tubing, etc.

FIG. 18 shows an alternative embodiment of the embodiment shown in FIG. 7 and in FIG. 8 of an insect transport device 100, wherein the further gas discharge members 131 and 131' located at the top side of the side walls in the embodiment of FIG. 7 are now replaced by gas discharge members 600*a* and 600*b*, comprising elongated slits 607*a* and 607*b* respectively, for discharging gas, e.g. temperature and absolute humidity controlled air, in directions 129' over the flat surface of flat side walls 113', 113" (optionally, the side walls 113', 113" are convex side walls similar to the side walls 113', 113" of FIG. 8). Gas discharge members 600*a* and 600*b* are connected to tubing or pipes 601*a* and 601*b*, respectively, jointly connected to driver 603 such as a fan 603, which driver 603 drives ambient air through tubing or pipes 601*a* and 601*b* towards slits 607*a* and 607*b*. The air driven by fan 603 is temperature controlled air and absolute humidity or relative humidity controlled air. Temperature and humidity is controlled with sensor 602. The air temperature and air humidity is kept within temperature boundaries and within humidity boundaries suitable for keeping insect alive which are transported through the insect transport device 100 and cyclone separation system 148. Preferably, with regard to this embodiment, the gas guiding unit 112 has a smaller width in the direction of side walls 113', 113" compared to said with for the gas guiding unit in the embodiments outlined in FIG. 7 and FIG. 8, preferably about 25% to smaller than 100% of said width, such as about half the width (8 cm-24 cm). The gas guiding unit 112 with a relatively smaller width provides the benefit of the requirement for less air for keeping insects airborne when travelling through the insect transport device without touching any inner surfaces of e.g. walls, tubes, etc. Similarly, the provision of the flat surface of the flat side walls 113', 113" also provides the benefit of the requirement for less air for keeping insects airborne when travelling through the insect transport device without touching any inner surfaces of e.g. walls, tubes, etc. Application of flat side walls 113', 113" with a flat surface provide the benefit that the decrease of the air velocity in the air flow from the top side of the flat side walls towards the gas guiding unit 112 is less, compared to the decrease of the air velocity in the air flow from the top side of the side walls towards the gas guiding unit 112 when the side walls 113', 113" are convex side walls with a convex surface. Applying flat side walls requires a lower initial air velocity at the top side of the side walls in order to maintain a sufficiently high air velocity at the side in proximity with the gas guiding unit 112. In addition, controlling and keeping constant the air velocity of air flowing over the surface of flat side walls 113', 113" is less demanding and more easily established compared to controlling air velocity of air flowing over a convex side wall surface.

FIG. 9 depicts an insect transport device 100 comprising an elongated cover member 132 arranged over and along a gas guiding unit 112. Further, thermally insulating material 301-303 in the side walls of casing 5 are provided for aiding in avoiding condensation of water inside the insects transport device during operation, when temperature drops in the air surrounding the insects transport device may occur.

In the embodiment shown, the insects transport device 100 may be considered to be the same as the one shown in FIG. 8 but wherein a cover member 132 is provided that extends above and along the gas guiding unit 112 at a clearance distance "C", thus wherein the cover member 132 extends along and above the at least one gas guiding members 12', 12", 12'" at a clearance distance "C" with respect thereto. The clearance distance "C" is sufficiently large to allow the first laminar flow of air with live insects, e.g. larvae or live mites, to flow freely over the top surface of each of the at least one gas guiding member 12', 12", 12'" extending underneath the cover member 132.

The cover member 132 prevents that the first laminar flow over the gas guiding unit 112, i.e. the at least one gas guiding member 12', 12", 12'", drags too much conditioned air toward the exit of the insects transport device 100 at a proximal end thereof. In case too much air is being dragged along with the first laminar flow, then this would produce too much turbulence at the exit because of the limited flow capacity there through causing air being lifted upward at the proximal end of the live insect larvae transport device 100.

Therefore, the cover member 132 maintains homogenous distribution of conditioned air around the insect eggs or live mites in the at least one reservoir 128, 128', 128*a*, 128*a'* by minimizing the amount of conditioned air being dragged away and/or downward therefrom along with the first laminar flow over the gas guiding unit 112.

In an embodiment, the cover member 132 has a height such that it extends and remains underneath the at least one reservoir 128, 128', 128*a*, 128*a'* so that conditioned air around the insect eggs or around the mites is prevented from being dragged with the first laminar flow over the gas guiding unit 112.

In another embodiment, the cover member 132 may further comprise a sloped roof 133 to prevent that live insects collect on the cover member 132 when dropping from the at least one reservoir 128, 128', 128*a*, 128*a'* onto the cover member 132, thereby ensuring that the live insects reach the first laminar flow of gas over the gas guiding unit 112.

In a further embodiment, the cover member 132 comprises a plurality of cover side walls 134, e.g. oppositely arranged cover side walls 134, wherein each cover side wall 134 extends in upward and longitudinal/lengthwise direction along one of the flat or convex side walls 113', 113" to further reduce any suction or dragging of conditioned air by the first laminar air flowing over the gas guiding unit 112. Note that lowest edges of each cover side wall 134 are arranged above the gas guiding member 112 at the aforementioned clearance distance C. In a further embodiment, the cover member 132 comprises a bottom side (not visible in FIG. 9) which may be an open or a closed bottom side. In case the bottom side is closed, then the bottom side extends along and above the gas guiding unit 112 at the aforementioned clearance distance C.

In an exemplary embodiment, the cover member 132 has a width $w_c$ which may be substantially the same as a width $W_g$ of the gas guiding unit 112. Since the cover member 132 is arranged above the gas guiding unit 112 at the clearance distance C, a slit "S" is provided between the cover member 132 and each of the flat or convex side walls 113', 113". These slits S still allow discharged air from the second gas discharge members 131, 131' to flow in laminar fashion over the flat or convex side walls 113', 113" and pass through these slits S toward each of the at least one gas guiding members 12', 12", 12".

In an exemplary embodiment, the cover member 132 may have a height between 10 cm to 20 cm, e.g. 20 cm, and a width $W_c$ of 3 cm to 7 cm, e.g. 5 cm.

FIG. 19 displays an embodiment of an insects transport device 100 with a similar set-up as the insects transport device 100 depicted in FIG. 7 and FIG. 9, wherein in FIG. 19 the further gas discharge members 131 and 131' located at the top side of the side walls in the embodiment of FIG. 7 are now replaced by gas discharge members 600*a* and 600*b*, comprising elongated slits 607*a* and 607*b* respectively, for discharging gas, e.g. temperature and absolute humidity controlled air, in directions 129' over the flat surface of flat side walls 113', 113", similar to the embodiment of FIG. 18 (optionally, the side walls 113', 113" are convex side walls similar to the side walls 113', 113" of FIG. 8). Again, by driving air over the flat surface, which air has preferably controlled and set temperature and humidity, and in addition by controlling the air velocity by fan 603, with the insects transport device 100 displayed in FIGS. 18 and 19 it is now possible to better keep insects such as neonate black soldier fly larvae alive during their time of flight starting at the ovisite from which they hatch and ending in a crate 156 comprising larvae feed at a suitable humidity and temperature favorable for development of the living insects.

As mentioned earlier, the at least one reservoir 128, 128', 128*a*, 128*a'* comprising live insects, e.g. insect eggs or mites, are to be maintained at a controlled and predetermined temperature and relative air humidity to stimulate and facilitate optimal hatching or optimal disposal of mites through the through holes in the bottom floor of the mite cage 128*a*, 128*a'*, such that optimal release of live insects from the at least one reservoir 128, 128', 128a, 128a' into the live insect receiving portion is achieved.

Figure 10:
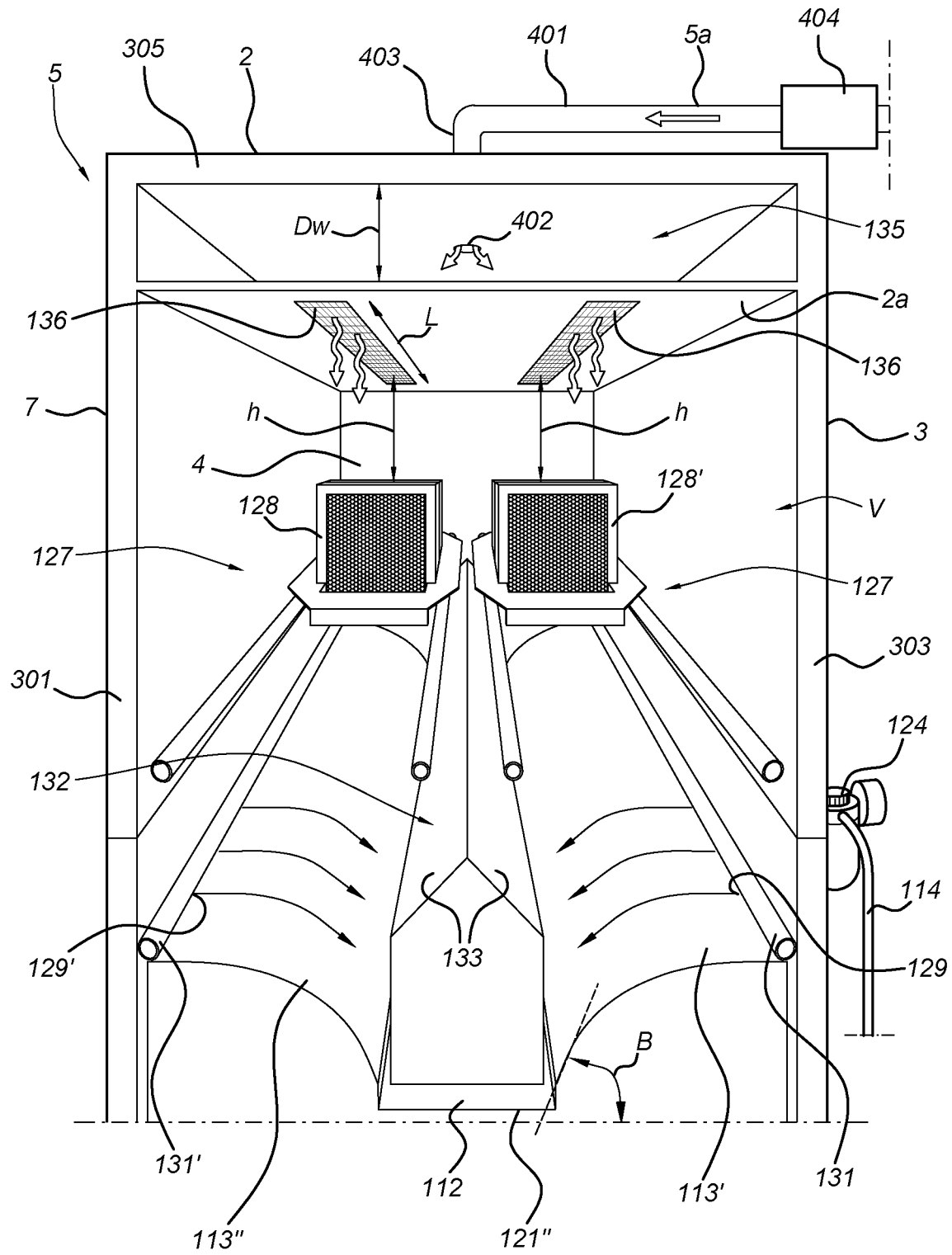
FIG. 10 shows a thermally insulated casing 5 of an insects transport device 100 according to an embodiment of the present invention, the insects transport device comprising a reservoir 128, the reservoir being an ovisite.

To provide optimal temperature and relative humidity condition, FIG. 10 shows a casing 5 of an insects transport device 100 according to an embodiment. In the depicted embodiment, the insects transport device 100 comprises a thermally insulated casing 5 covering the gas guiding unit 112 in the inners side of the casing 5, the flat or convex side walls 113', 113", and the feeder arrangement 127 in which the at least one reservoirs 128, 128', 128a, 128a' are received. The casing 5 comprises a thermally insulated top wall 2 and thermally insulated side walls 3, 3a, 4, 4A, 7 defining the inner side, and in particular a closed inner space or volume "V" in which the temperature is controllable as well as the relative humidity to provide an environment for the at least one reservoir 128, 128', 128a, 128a' to stimulate and facilitate optimal hatching or to stimulate and facilitate optimal migration of mites through openings in the bottom floor of cages 128a, 128a'. In order to provide air of a particular temperature and/or relative humidity, the insects transport device 100 further comprises an air feed channel 5a, comprising tube 401 and connector 403 connected to the top wall 2 via opening 402 of the casing 5 for providing air of a desired temperature and/or relative humidity, under control of temperature control unit and relative air humidity control unit 404, to the inner side of the casing 5 and in particular to the inner volume V.

In an embodiment, the casing 5 may be provided with a secondary top wall 2a arranged below the top wall 2 at wall distance $D_w$ therefrom such that a cavity space 135 is defined between the top wall 2 and secondary top wall 2a. The secondary top wall 2a further comprises one or more slits 136 such that air from the air feed conduit 5a entering the cavity/buffer space 135 is able to flow toward the inner volume V. That is, the one or more slits 136 fluidly connect the cavity/buffer space 135 and the inner volume V of the casing 5. The one or more slits 136 provided in the secondary top wall 2a allow air, e.g. temperature and/or humidity controlled air, to be provided to the inner volume V in distributed fashion so as to minimize turbulence in the inner volume. Therefore, the cavity space 135 in conjunction with the one or more slits 136 allow air from the air feed conduit 5a to enter the inner volume V with maximum homogeneity. The casing 5 is provided with thermally insulating top wall and side walls.

In an embodiment, the one or more slits 136 are arranged in longitudinal fashion, i.e. in a lengthwise direction "L" as depicted, thereby providing conditioned air in homogenous fashion along the gas guiding unit 112. In an exemplary embodiment, each of the one or more slits 136 extends along 70% to 90%, e.g. 80%, of a length of the first laminar flow of gas, e.g. air, over the top surface of the at least one gas guiding member 12', 12", 12"'. In an exemplary embodiment, each of the one more slits 136 has a length between 50 cm to 100 cm, e.g. 60 cm, 65 cm, 70 cm. In a further exemplary embodiment, each of the one or more slits 136 has a width of about 3 cm to 6 cm, e.g. 4 cm or 5 cm, to further facilitate homogenous distribution of conditioned air entering the inner volume V of the thermally insulated casing 5.

In an advantageous embodiment, the one or more slits 136 extend above the at least one reservoir 128, 128', 128a, 128a' containing the live insects, e.g. insect eggs or live mites, for which conditioned air is to be provided for optimized hatching, or optimized migration downward in the mite cage 128a, 128a'.

In another embodiment, each of the one or more slits 136 comprises a plurality of perforations covering 40% to 60%, e.g. 50%, of a surface area of the slit 136. In further embodiments each of the perforations is a substantially circular perforation having a diameter of about 4, 5, or 6 mm for example.

In an embodiment, the secondary top wall 2a with the one or more slits 136 is arranged above the at least one reservoir 128, 128' at a height of 5 cm to 15 cm, e.g. 10 cm to provide the conditioned air to the at least one reservoir 128. 128'.

Figure 1B:
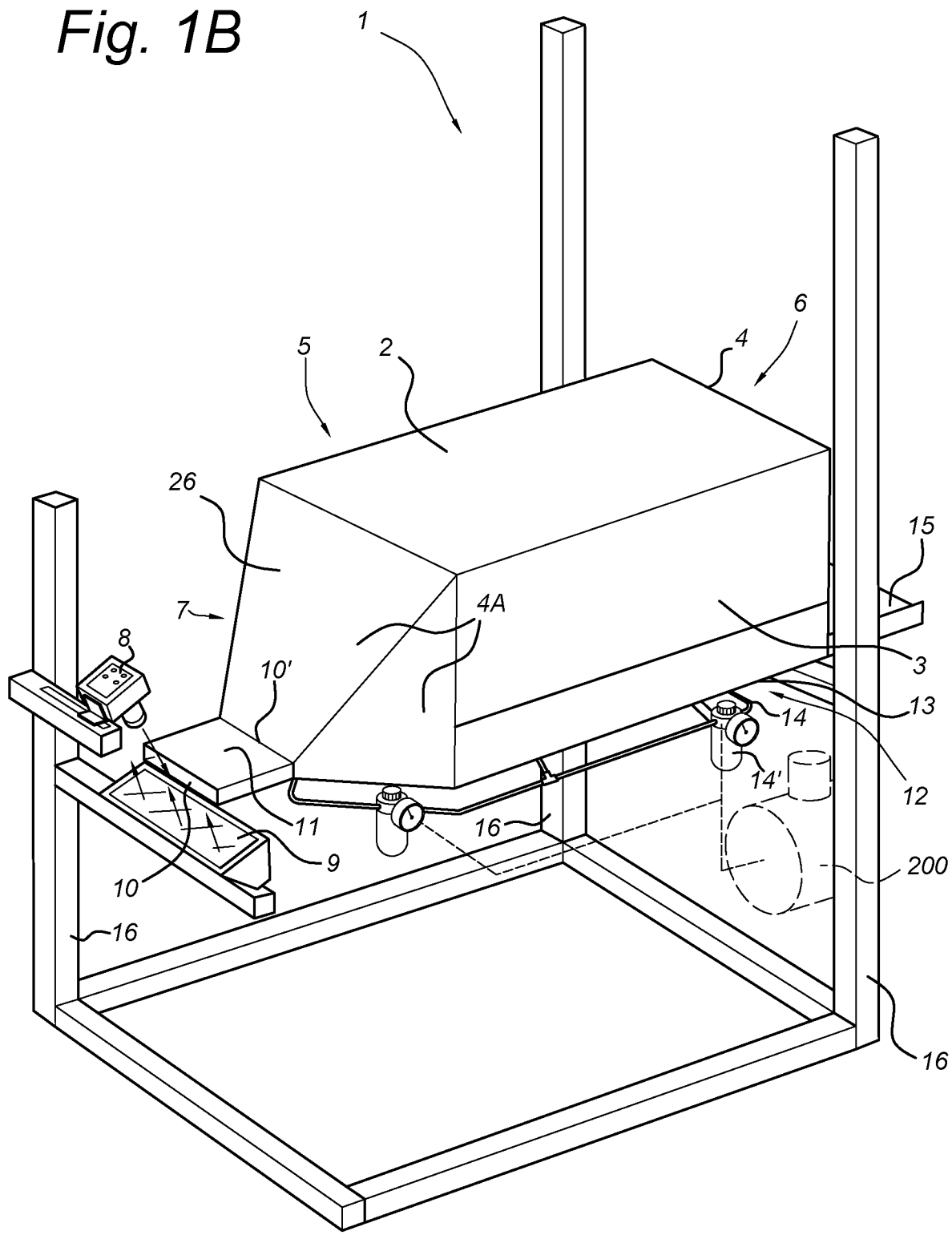
Figure 2:
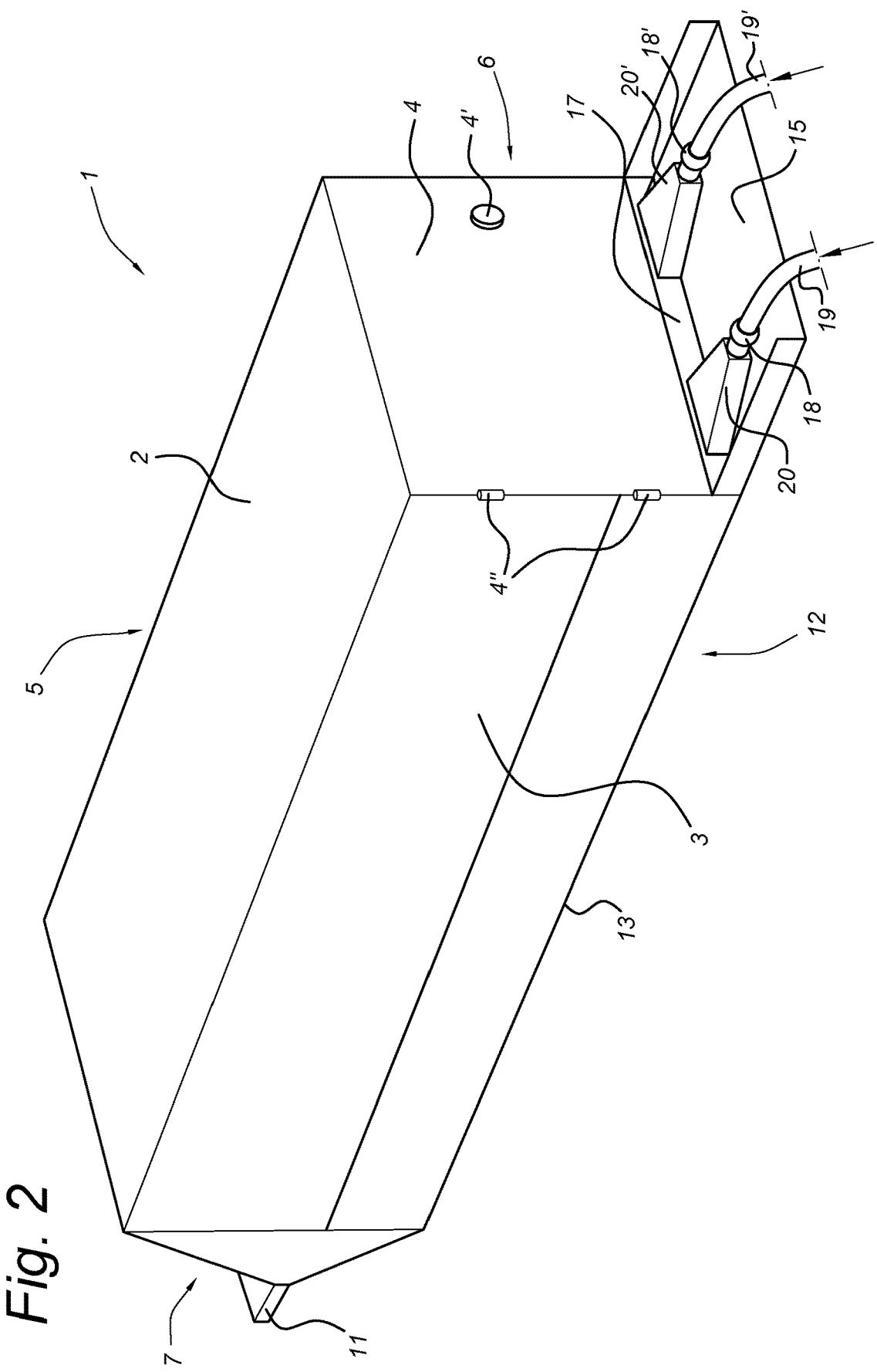
FIG. 2 displays an overview of an insects transport device 1 of the invention comprising a thermally insulated casing 5 and a gas guiding unit 12 that provides a smooth longitudinal path for a laminar flow of gas, and further displays the distal end 15 of the gas guiding unit which receives the gas discharge members 20, 20' through an opening 17 in the casing 5.
Figure 3:
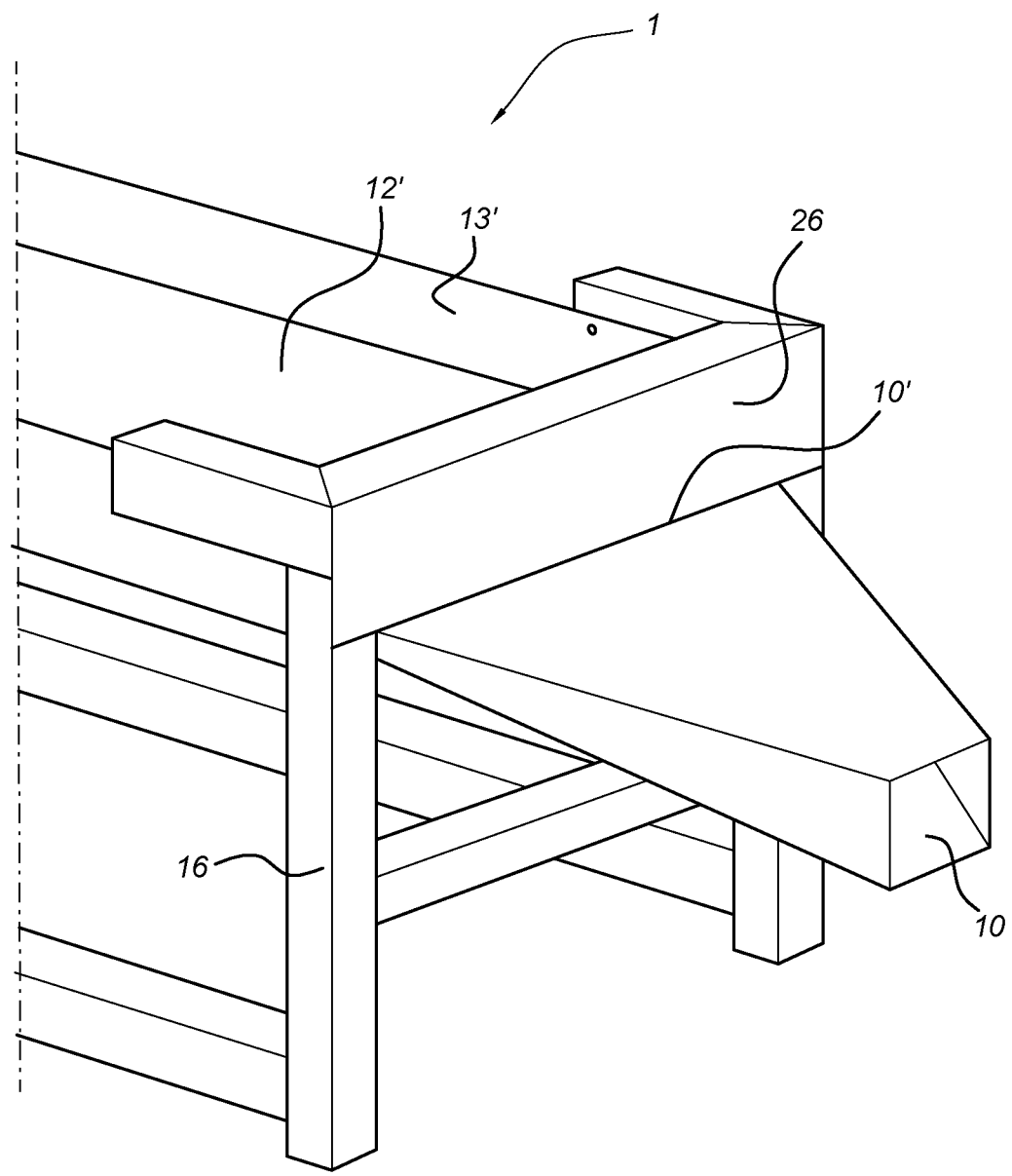
FIG. 3 displays a detailed side view of an insects transport device 1 of the invention where the proximal end of the gas guiding unit 12' ends and where the insect discharge member (See also 11 in FIG. 2) is located and coupled to said proximal end.
Figure 4:
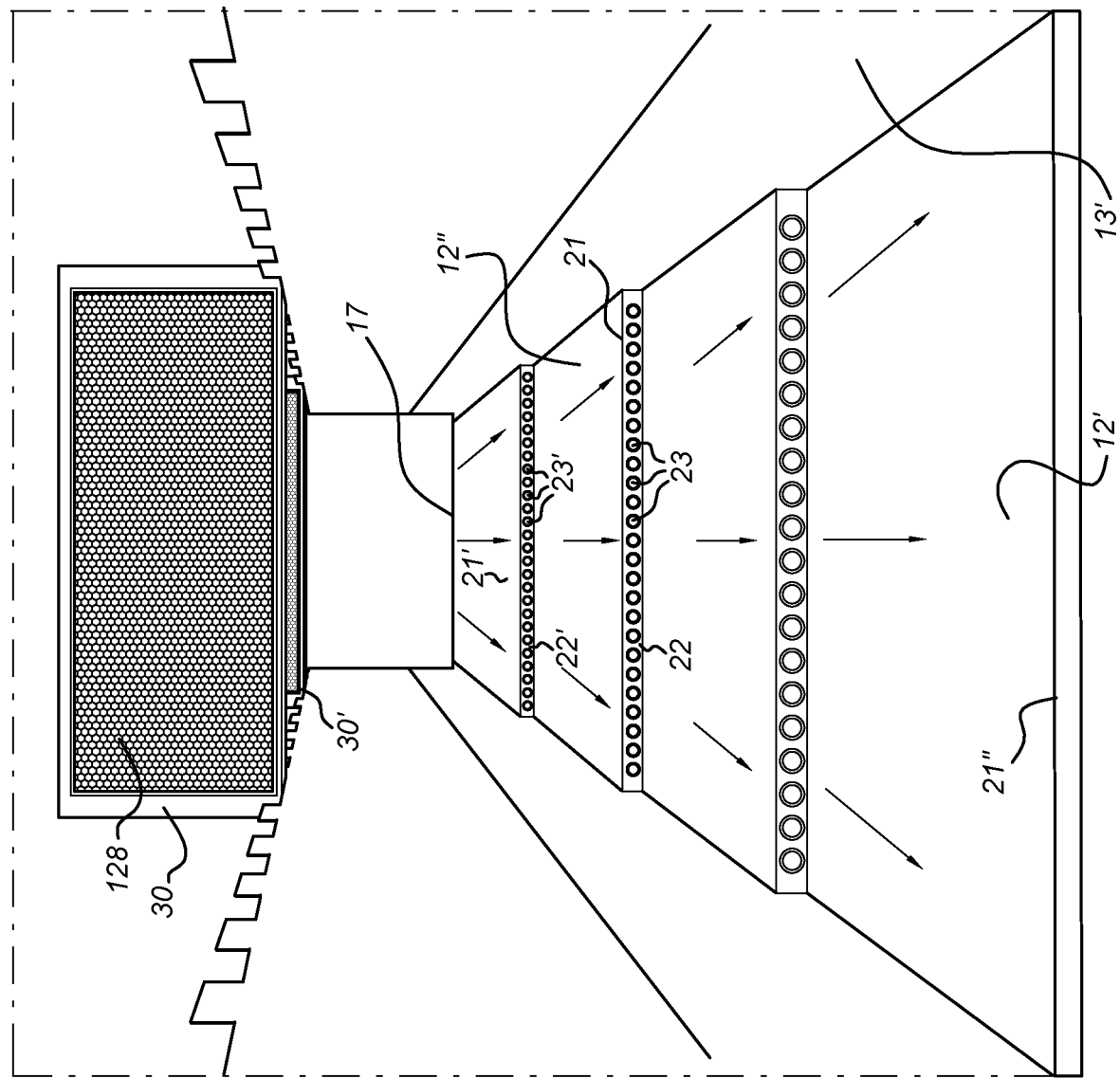
FIG. 4 displays an inside view of an insects transport device of the invention. Shown are longitudinal gas transport members 12', 12" which are connected imbricatedly at positions 21, 22 and 21', 22'. Where two consecutive gas transport members are coupled imbricatedly, a gas discharge member (See 20, 20' in FIGS. 2 and 114', 114", 114''' in FIG. 5) is positioned at the location where said gas transport members overlap, said gas discharge member provided with openings 23, 23' for discharging gas.

As mentioned earlier, the insects transport device 100 may comprise a live insects counting device 8, e.g. a camera, for counting live insects in the first laminar flow exiting the insects transport device 100 at the proximal end of the live insect discharge member 11 as shown in FIGS. 1A, 1B, and 2. In one embodiment, the live insects discharge member 11 may be a funnel shaped discharge member 11, e.g. having a rectangular cross section, configured to provide a narrow stream of gas for accurate counting of the live insects exiting the insects transport device 100.

Figure 11:
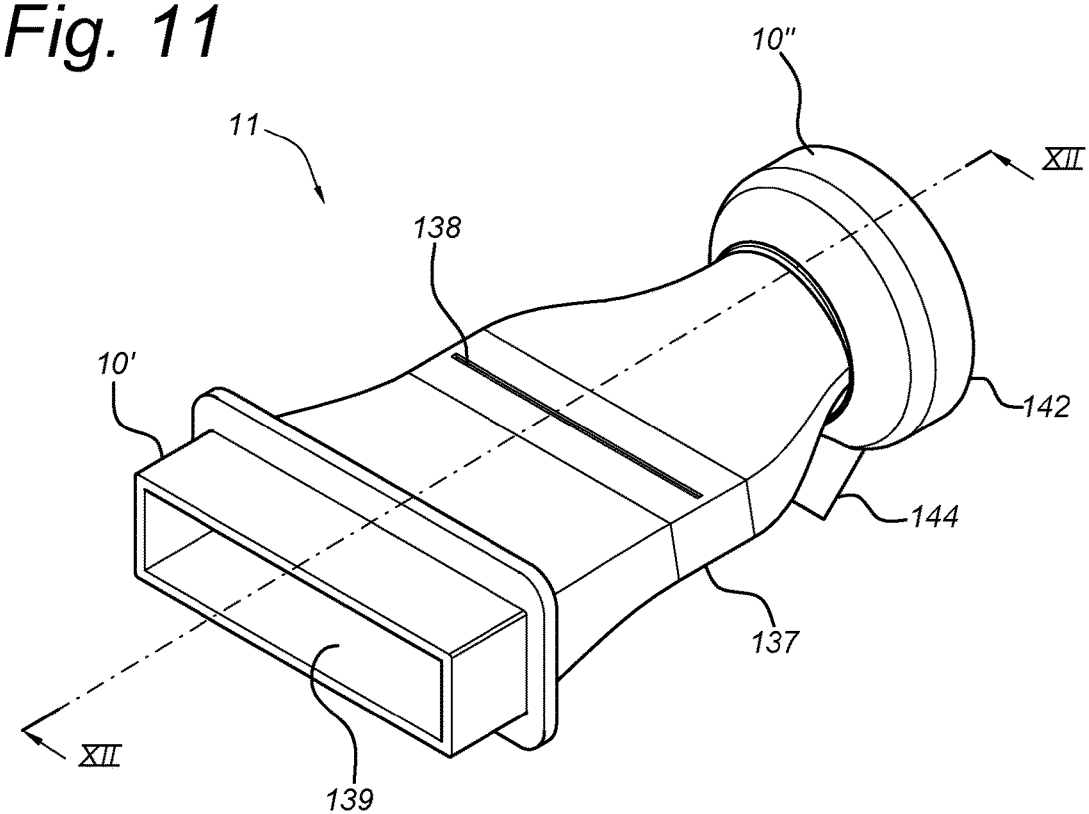
FIG. 11 shows a three dimensional view of a live insect discharge member 11 according to an embodiment of the present invention.
Figure 12:
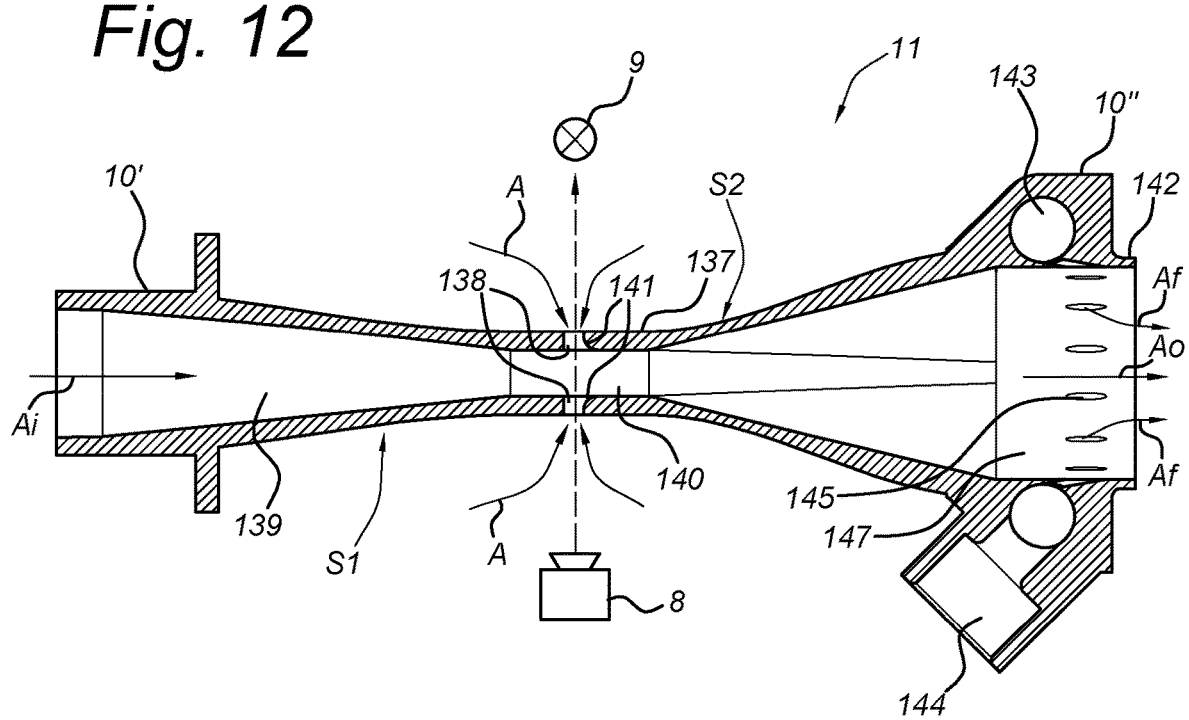
FIG. 12 shows a cross sectional view of a live insect discharge member 11 according to an embodiment of the present invention.

To further improve upon the accuracy and reliability of counting live insects exiting the insects transport device 100, further embodiments of the live insects discharge member 11 as discussed earlier are conceivable. For example, FIG. 11 shows a three dimensional view of a live insect discharge member 11 and FIG. 12 shows a cross sectional view of the live insect discharge member 11.

In the depicted embodiments, the live insect discharge member 11 may comprise a throat portion 137 arranged between the distal end 10', i.e. the first end, and a proximal end 10", i.e. the second end, of the live insect discharge member 11. That it, a discharge channel 139 of the live insect discharge member 11 extends between the distal end 10' and proximal end 10" thereof and comprises a constricted or choked channel portion 140 at the throat portion 137. Here, the distal/first end 10' is configured for connection to the insects transport device 100 such that live insects exiting the insects transport device 100 can travel through the discharge channel 139 by entering at the distal/first end 10' and exiting from the proximal/second end 10".

As shown, the throat portion 137 is provided with a through hole 138, e.g. shaped as a (elongated) slit 138, laterally/sideways extending through the throat portion 137. The through hole/slit 138 allows the counting device 3, e.g. a camera, to be arranged next to the slit shaped through hole 138 and have a field of view into the discharge channel 139, in particular the constricted channel portion 140, for counting the number of live insects passing through the live insect discharge member 11 as they exit the insects transport device 100.

The advantage of having the slit shaped through hole 138 at the constricted channel portion 140 is that a pressure drop in the constricted channel portion 140 will develop according to the Venturi effect or Venturi principle. That is, the constricted channel portion 140 induces a Venturi effect allowing outside air "A" to be drawn/sucked into the constricted channel portion 140 via the slit shaped through hole 138 when an air stream carrying live insects flows through the discharge channel 139. As a result, suction at the slit shaped through hole 138 allows live insects to be counted by the counting device 3 whilst preventing that live insects escape the live insect discharge member 11 via the slit shaped through hole 138.

For improved operation of the counting device 8, e.g. a camera, a light source such as a lamp 9 may be provided as mentioned earlier with reference to FIG. 1A, 1B. To improve operation of the counting device 8, FIG. 12 shows an embodiment of a light source 9 such as an elongated lamp arranged next to and extending along the slit shaped through hole 138 on an opposite side of the live insect discharge member 11 with respect to the counting device 8. In particular, the counting device 8 is arranged on a first side $S_1$ whereas the light source 9 is arranged on an opposing second side $S_2$ of the live insect discharge member 11. Light from the light source 9 is able to pass through the slit shaped through hole 138 and reach the counting device 8. The constricted channel portion 140 then prevents live insects escaping through the slit shaped through hole 138 by virtue of the suction effect explained above when an air stream carrying live insects passes through the discharge channel 139.

Note that suction at the slit shaped through hole 138 allows the counting device 3 to be arranged on both sides $S_1$, $S_2$, e.g. above or below, the live insect discharge channel 11 and the light source 9 may then be arranged below or above the live insect discharge channel 11 respectively. In any case, the constricted channel portion 140 prevents live insects escaping via the slit shaped through hole 138 on both sides $S_1$, $S_2$ of the live insect discharge member 11. Since live insects cannot escape through the slit shaped through hole 138, contamination of the counting device 8 and/or light source 9 is eliminated, allowing the counting device 8 and light source 9 to be placed on either side $S_1$, $S_2$ of the live insect discharge member 11 whilst still allowing accurate counting of the number of live insects exiting the insects transport device 100.

Figure 18:
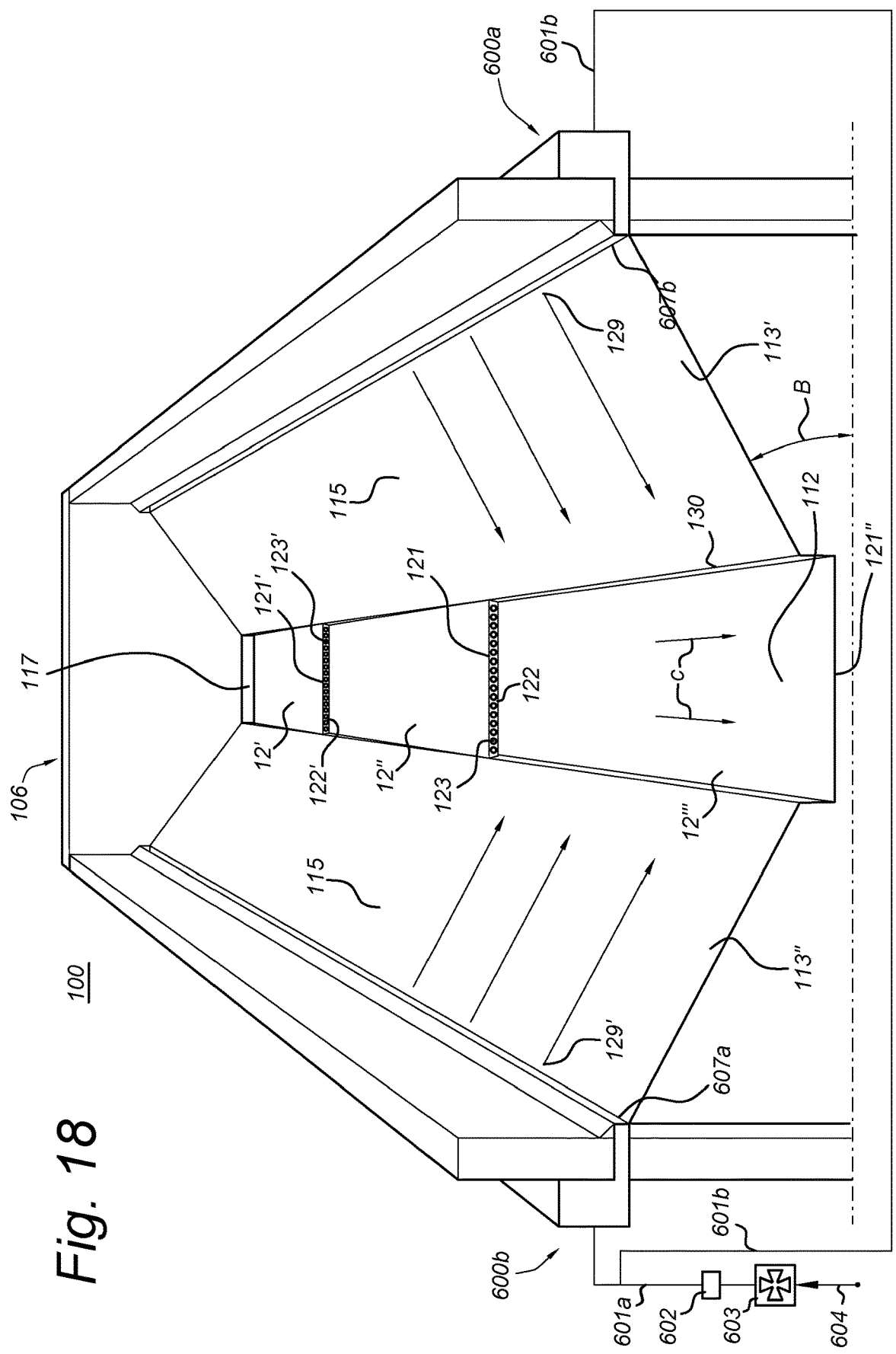
FIG. 18 depicts an insects transport device 100 comprising a gas guiding unit 112 and flat side walls 113', 113" arranged there along according to an embodiment of the present invention.
Figure 19:
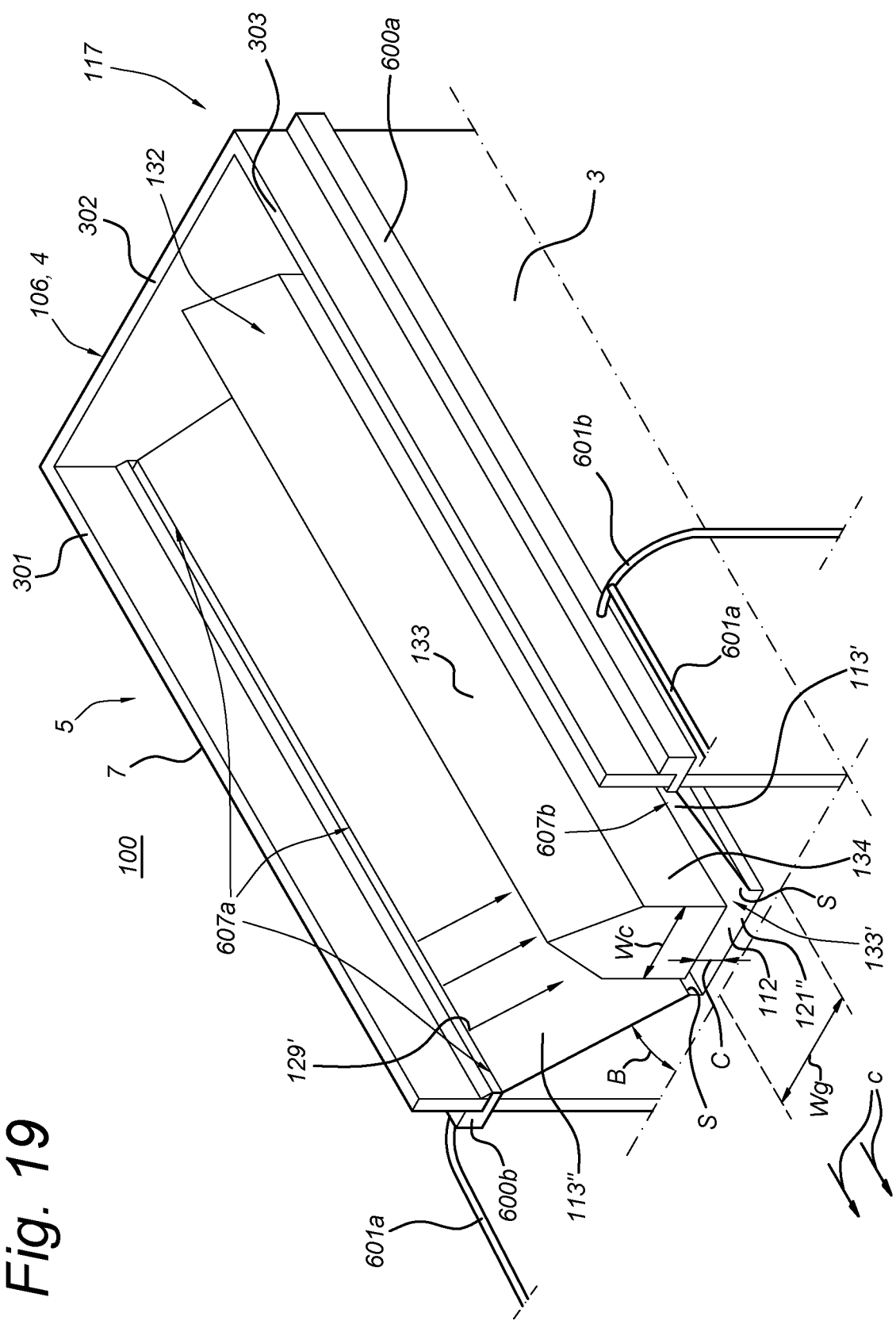
FIG. 19 depicts an insects transport device 100 comprising a cover member 132 arranged over and along a gas guiding unit 112, further comprising a gas guiding unit 112 and flat side walls 113', 113" arranged there along and air slits 607a and 607b arranged along the top side of the flat side walls, according to an embodiment of the present invention.
Figure 21:
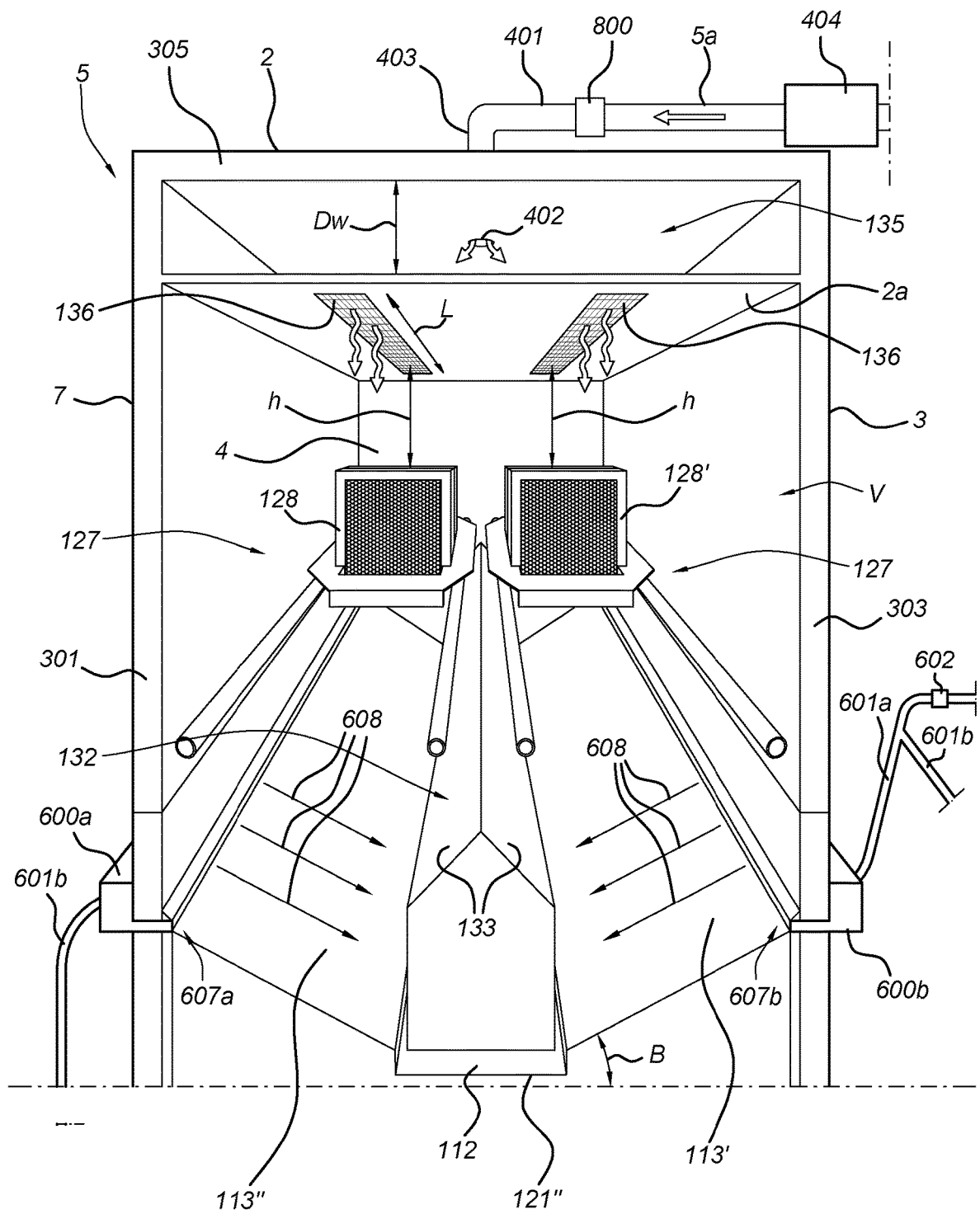
FIG. 21 shows a thermally insulated casing 5 of an insects transport device 100 according to an embodiment of the present invention, the insects transport device 100 comprising a reservoir 128, 128', the reservoir being an ovisite.

FIG. 21 displays a casing 5 of an insects transport device 100 according to an embodiment similar to the embodiment outlined in FIG. 10, with the difference that similar to the embodiments in FIGS. 18-20, wherein the further gas discharge members 131 and 131' located at the top side of the side walls in the embodiment of FIG. 7 and FIG. 11 are now replaced by gas discharge members 600a and 600b, comprising elongated slits 607a and 607b respectively, for discharging gas, e.g. temperature and absolute humidity controlled air, in directions 608 over the convex surface of convex side walls 113', 113" or over the flat surface of flat side walls 113', 113". Gas discharge members 600a and 600b are connected to tubing or pipes 601a and 601b, respectively, jointly connected to driver 603 (See FIG. 18 and FIG. 20) such as a fan 603, which driver 603 drives ambient air through tubing or pipes 601a and 601b towards slits 607a and 607b. The air driven by fan 603 is temperature controlled air and absolute humidity or relative humidity controlled air. Temperature and humidity is controlled with sensor 602. The air temperature and air humidity is kept within temperature boundaries and within humidity boundaries suitable for keeping insect alive which are transported through the insect transport device 100 and cyclone separation system 148.

As shown in FIGS. 11 and 12, in an embodiment the constricted channel portion 140 comprises a rectangular cross section, which allows a relatively narrow and elongated air stream of live insect to pass through the constricted channel portion 140 so that the counting device 8 is able to count the number of live insects much more accurately with a minimal number of uncounted live insects, which could have been be blocked by another live insect in the field of view of the counting device 8.

To obtain a most optimal field of view into the constricted channel portion 140, an embodiment is provided wherein the slit shaped through hole 138 has a length of at least 90% percent of a width of the constricted channel portion 140 in the lateral direction of the slit shaped through hole 138. This embodiment minimizes the number of live insects that could potentially bypass the field of view of the counting device 8.

In an embodiment, the slit shaped through hole 138 comprises a chamfered or rounded downstream inner edge 141, i.e. extending in the lengthwise direction of the slit shaped through hole 138 on a downstream side thereof, thereby reducing turbulence and maintaining laminar flow within the constricted channel portion 140 when air A is being drawn into the constricted channel portion 140 in the direction of air flowing from the first end 10' to the second end 10".

The live insect discharge member 11 with the slit shaped through hole 138 enabling a field of view into the constricted channel portion 140 allows for an extremely useful counting device 8 which is able to accurately count the number of live insects exiting the insects transport device 100. In particular, because accurate counting of live insects is now possible by means of the live insect discharge member 11, information on hatch and development characteristics of live insects in the insects transport device 100 can be deduced. For example, by counting the number live insects passing the live insect discharge member 11 it is possible to deduce what the effects are of temperature and/or relative humidity on live insects (e.g. insect eggs, mature mites) and their hatch time (e.g. when eggs of for example black soldier flies are present in ovisites 128, 128') or their migration time (e.g. when mites are present in the reservoir(s) 128a, 128a') in the at least one reservoir 128, 128a. Therefore, the live insect discharge member 11 and counting device 8 allow for gaining further information on live insect hatching characteristics or live insect migration characteristics.

Although the constricted channel portion 140 prevents live insect escaping though the slit shaped through bore 138, an outgoing air stream $A_o$ with live insects exiting the live insect discharge member 11 at its proximal/second end 10" is generally slower than an incoming air stream $A_i$ entering the distal/first end 10'. To compensate for this loss of speed, an embodiment is provided wherein the proximal/second end 10" of the live insect discharge member 11 is provided with an air amplifier unit 142 which is configured to inject further air $A_f$ into the second end 10" of the live insect discharge member 11. This ensures that an outgoing air stream $A_o$ with live insects has sufficient speed and momentum to flow to other parts of the insects transport device, such as a cyclone separation system 148, connected to the second end 10" of the live insect discharge member 11.

In an exemplary embodiment, the air amplifier unit 142 comprises a circumferential chamber 143 fluidly coupled to an air feed connection 144 for connection to an air feed allowing further air $A_f$ to be injected into the proximal second end 10" of the live insect discharge member 11, and wherein one or more air amplifier outlets 145 are circumferentially arranged in an inner wall 147 of the second end 10" of the live insect discharge member 11 and wherein the one or more air amplifier outlets 145 are fluidly connected to the circumferential chamber 143. In this embodiment, the one or more air amplifier outlets 145 allow for an even injection of the further air $A_f$ into the second end 10" such that turbulence is minimised. In an exemplary embodiment, a single air amplifier outlet 145 may be provided in the form of a circumferential slit in the inner wall 147 fluidly coupled to the circumferential chamber 143, allowing for even injecting of further $A_f$.

As mentioned above, the air amplifier unit 142 allows for an outgoing air stream $A_o$ with live insects which has sufficient speed and momentum to flow to other parts of a system, such as a cyclone separator 148, connected to the second end 10" of the live insect discharge member 11.

Figure 13:
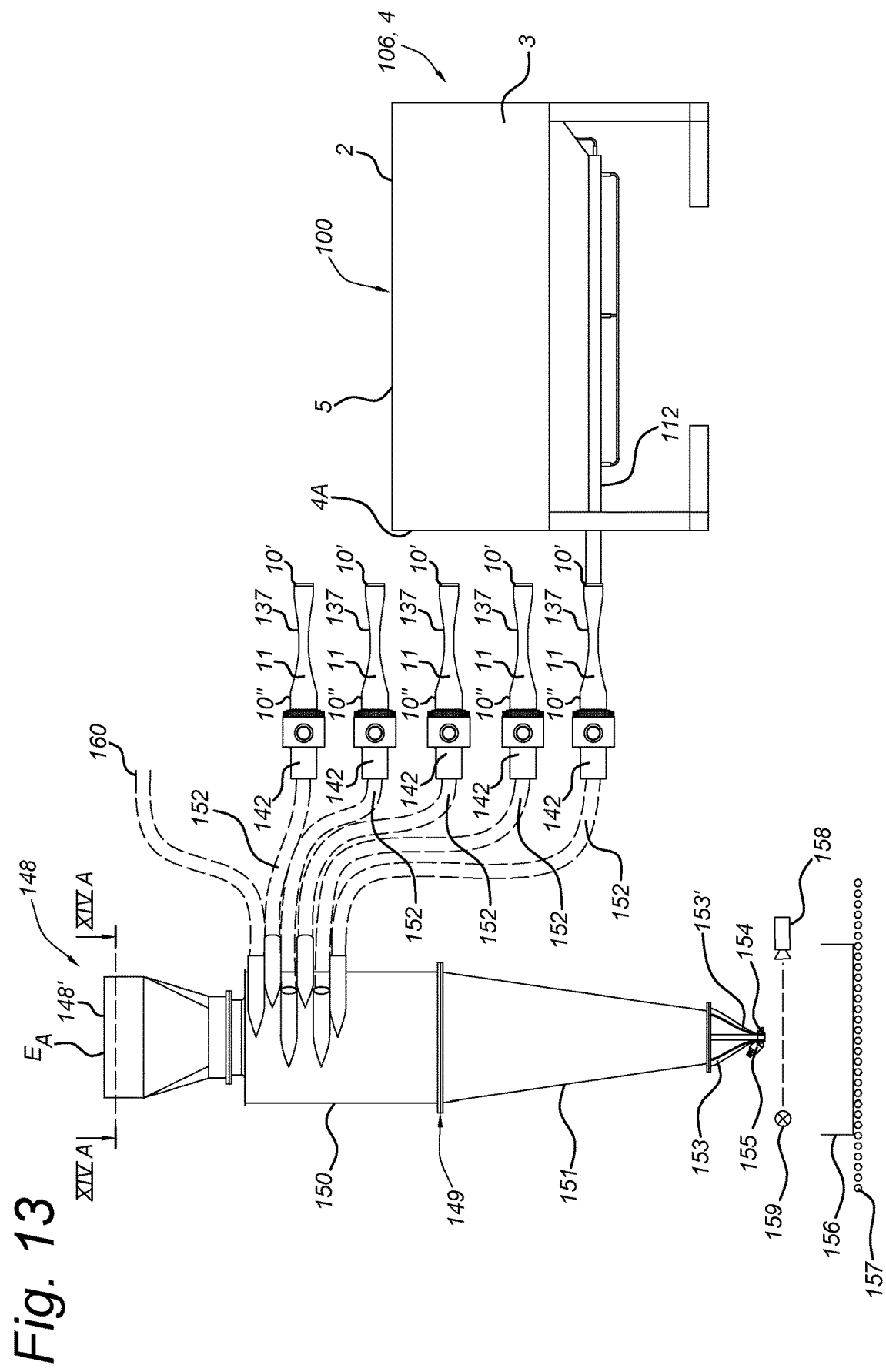
FIG. 13 shows a schematic view of an insects transport device 100 further provided with a cyclone separation system 148 connected to the live insect discharge member 11, according to an embodiment of the present invention.

FIG. 13 shows a cross sectional view of such a cyclone separation system 148 connected to one or more insects transport devices 100 according to an embodiment. In the embodiment shown, the transport device 100 comprises the live insect discharge member 11 described earlier, e.g. comprising the throat portion 137 with the slit shaped through hole 138 and the constricted channel portion 140 to prevent live insects escaping there through by virtue of the Venturi effect. A counting device 8 may be provided next to the slit shaped through hole 138, possibly with a light source 9 such as a lamp on an opposite side of the throat portion 137. The slit shaped through hole 138 allows the counting device 8 to have a field of view into the constricted channel portion 140 for counting live insects passing through the live insect discharge member 11. The light source 9 is able to provide additional illumination through the slit shaped through hole 138.

As depicted, a cyclone separation system 148 is connected to one or more insects transport devices 100 to separate live insects from an outgoing air stream $A_o$ of each live insect discharge member 11. The cyclone separation system 148 comprises a main cyclone chamber 149 having a top chamber part 150 and a conical shaped bottom chamber part 151, wherein the top chamber part 150 is connected to one or more intake channels 152 each of which is arranged for connection to a primary air source providing an air stream comprising live insects. Here, the air stream provided by the primary air source is an outgoing air stream $A_o$ of a live insect discharge member 11 as described above. Therefore, each of the one or more intake channels 152 is arranged for connection to an insects transport device 100 of the one or more insects larvae transport devices 100.

Note that only one insects larvae transport device 100 is depicted for clarity purposes and the skilled person will understand the each of the depicted first ends 10' of the live insect discharge members 11 is connected to an insects transport device 100.

The bottom chamber part 151 of the cyclone separation system 148 is connected to a discharge nozzle 153 comprising a discharge end 153' having a main discharge conduit (not shown) for discharging the live insects from the cyclone separation system 148. The discharge end 153' comprises an air injection member 154 for connection to a secondary air source 155 and wherein the air injection member 154 is configured to inject air back into the discharge nozzle 153. Injecting air back into the discharge nozzle 153 stops the discharge of live insects.

In an advantageous embodiment, the air injection member 154 is configured for intermittent air injection back into the discharge nozzle 153.

Each of the one or more insects transport devices 100 provides an outgoing air stream $A_o$ with live insects passing through a live insect discharge member 11 toward the cyclone separation system 148, which subsequently discharges separated live insects in batch wise fashion by intermitted operation of the air injection member 154. When desired, the cyclone separation system 148, discharges separated live insects in continuous fashion by continuous operation of the air injection member 154.

As the skilled person will understand, in operation the one or more intake channels 152 carrying the outgoing air streams $A_o$ induce a main vortex in the top chamber part 150 allowing centrifugal separation of the live insects from the combined outgoing air streams $A_o$ in the top chamber part 150. The separated live insects follow a conical inner wall of the bottom chamber part 151 toward the discharge nozzle 153. Due to the conical shaped bottom chamber part 151, an ascending inner vortex of "clean" air is generated that exits the top chamber part 150 through an air exit EA arrange thereon.

Discharged live insects may be collected in a container 156 arranged underneath the discharge nozzle 153 and wherein the container 156 is movable by means of a conveyor system 157. For example, such container is a crate provided with feed substrate for live insects such as insect larvae, such as for example neonate larvae of black soldier fly. For example, in case the container 156 contains a desired number of live insects, then the air injection member 154 may be activated to inject air back into the discharge nozzle 153 as a result of which discharge of live insects is temporarily stopped. As the discharge of live insects has stopped, the container 156 may be replaced with another container, and once the other container has been correctly positioned, the air injection member 154 may be deactivated to resume discharge of separated live insects from the cyclone separation system 148. This way, accurate, controllable and constant dosing of for example live adult insects such as live mites is made possible.

In an embodiment, the cyclone separation system 148 may comprise a further counting device 158, e.g. a further camera, arranged next to the discharge nozzle 153 for counting the number of live insects being discharged therefrom. Activation and deactivation of the air injection member 154 may be controlled based on the counted number of live insects being discharged. Optionally, a further light source 159 may be provided to improve illumination conditions for the further counting device 158.

As further shown, the second end 10" of each live insect discharge member 11 may be provided with an air amplifier unit 142 to boost the outgoing air stream $A_o$ such that it attains sufficient speed and momentum.

Advantageously, a plurality of insects transport devices 100 are connected to a corresponding number of intake channels 152 so that the cyclone separation system 148 may operate continuously without interruption to the flow of live insects entering the cyclone separation system 148. In this way the cyclone separation system 148 can be scaled up to achieve batch wise discharge of any desired number of live insects. Note that the top chamber part 150 may be connected to an auxiliary intake channel 160 configured to provide a "pilot" air stream into the top chamber part 150 to further optimize centrifugal separation of the live insects entering the main cyclone body 149.

These embodiments of insects transport devices of the invention are all suitable for transportation of live neonate larvae of the black soldier fly, which larvae have a body diameter of between 1 mm and 4 mm and a body length which ranges between 5 mm and 12 mm. In addition, these embodiments of insects transport devices of the invention are all suitable for transportation of live insects such as mites.

While the invention has been described in terms of several embodiments, it is contemplated that alternatives, modifications, permutations and equivalents thereof will become apparent to one having ordinary skill in the art upon reading the specification and upon study of the drawings. The invention is not limited in any way to the illustrated embodiments. Changes can be made without departing from the scope which is defined by the appended claims.

FIG. 20A shows a cross sectional view of such a cyclone separation system 148 connected to one or more insects transport devices 100 according to an embodiment similar to the embodiment outlined in FIG. 13. In the embodiment of FIG. 20A, the insect transport device 100 comprises the gas discharge members 600*a* and 600*b*, comprising elongated slits 607*a* and 607*b* respectively, for discharging gas, e.g. temperature and absolute humidity controlled air, in directions 129' over the flat surface of flat side walls 113', 113", (although said surface can also be a convex surface of convex side walls 113', 113"), similar to the embodiment of FIGS. 18 and 19. Again, by driving air over the flat surface, which air has preferably controlled and set temperature and humidity, and in addition by controlling the air velocity by fan 603, with the insects transport device 100 displayed in FIGS. 18 and 19 it is now possible to better keep insects such as neonate black soldier fly larvae alive during their time of flight starting at the ovisite from which they hatch and ending in a crate 156 comprising larvae feed at a suitable humidity and temperature favorable for development of the living insects. The air amplifier unit 142' of each of the insects transport device 100 now comprised by the cyclone separation system 148 is in this embodiment connected through connectors 706 to a tube or a pipe 705, which tubes or pipes 705 are connected to a driver such as a fan through connector 704 provided with an air temperature control unit 703 and absolute air humidity control unit 703, for controlling the temperature and air humidity of the (ambient) air 701 driven by fan 702 through pipes 705 towards air amplifiers 142'. This way, temperature and air humidity of the air applied for amplifying the air stream blown from the direction of the insects transport device 100 towards the cyclone top chamber part 150 and comprising living insects such as neonate larvae, is kept within temperature boundaries and absolute air humidity boundaries favourable for keeping transported insects alive, and at the same time keeping these insects from touching walls or inner sides of tubes, etc., and preventing insects from sticking to sides of inner pipes, tubes, cyclone chambers, etc. Preferably, the cyclone separation system 148 and the cyclone separation system 148 comprising one or more insects transport devices 100 and the insects transport devices 100 are kept in an air-conditioned room 900. Preferably in the air-conditioned room 900, air temperature and air absolute humidity are such that when this air is provided by fan 702 and/or fan 603 inside the cyclone separation system 148 at an air velocity suitable for transporting living larvae and for keeping the larvae alive and air born, the air temperature and the air humidity contribute to the health of the insects and aids in keeping the insects alive during transport, counting and dosing.

An embodiment is the cyclone separation system 148 according to the invention and/or the insects transport device 100 of the invention, wherein the system and/or the device, preferably both, is/are encompassed by an air-conditioned volume 900 such as a climate room 900, and wherein preferably both temperature and air humidity are controlled in said air-conditioned volume 900, wherein preferably temperature controlled air is kept at a temperature of between 25° C. and 36° C., such as 26° C.-35° C. or 27° C.-34° C. and/or wherein optionally specific-humidity controlled air with a specific humidity at 1 atm. is kept at between 0.014 kg/kg and 0.026 kg/kg, preferably 0.015 kg/kg-0.025 kg/kg, more preferably 0.016 kg/kg-0.024 kg/kg inside the air-conditioned volume 900.

FIG. 20B shows a schematic view of a cyclone separation system 148 further provided with a plurality of insects transport devices 100 fluidly connected to the live insect discharge member 11, 11', 11*a* via tubing 11*b* and air amplifier unit 142', according to an embodiment of the present invention. This way, the air amplifier unit 142' is brought in close proximity with the connector 707 for connecting insects transport device 100 to the cyclone chamber 150 (See also FIG. 23), and this way, the live insect discharge member 11, 11', 11*a* and the air amplifier 142' are separated from each other by tubing 11*b*. With the air amplifier 142' positioned downstream relative to the position of the air amplifier in the embodiment of FIG. 20A (i.e. the amplifier is positioned in close proximity with the live insect discharge member 11, 11', 11*a*, closer to the proximal end 121" of the gas guiding unit 112 of the insects transport devices 100), the air velocity and/or the air pressure is improvingly controllable and is improvingly kept at constant values.

FIG. 20C shows an excerpt (blown-up view) of part of the embodiment displayed in FIG. 20B. Shown are the relative positions of the air amplifiers 142' and the live insect discharge members 11, 11', 11*a*, connected with tubing 11*b*. The air amplifiers 142' are each connected with tubes 705, connected with a fan 702 and/or fan 603 through connectors 706.

Figure 14A:
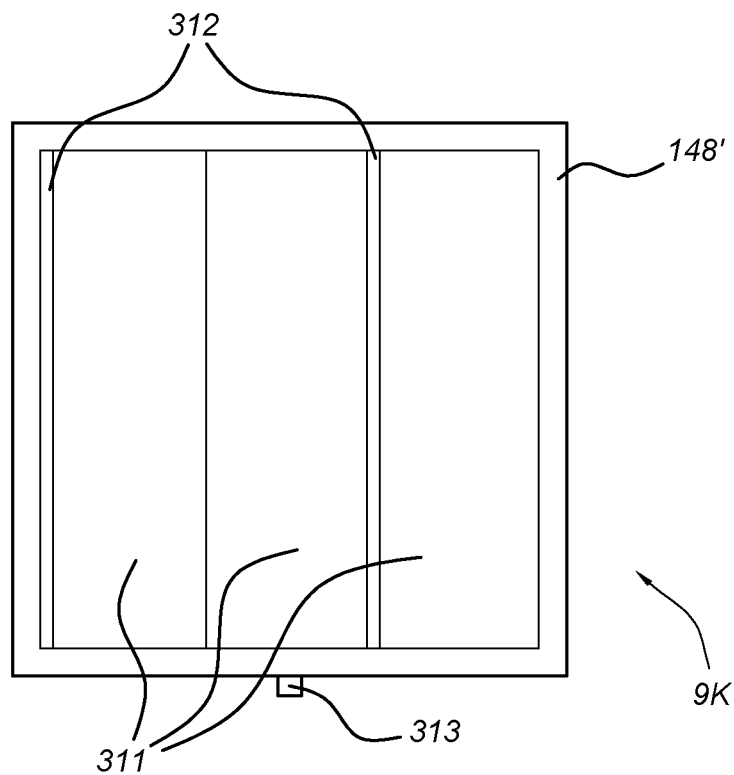
FIG. 14A shows a top view of the cyclone separation system 148, comprised by the insects transport device of the invention, showing laminar slats that are openable under control of a control unit.
Figure 14B:
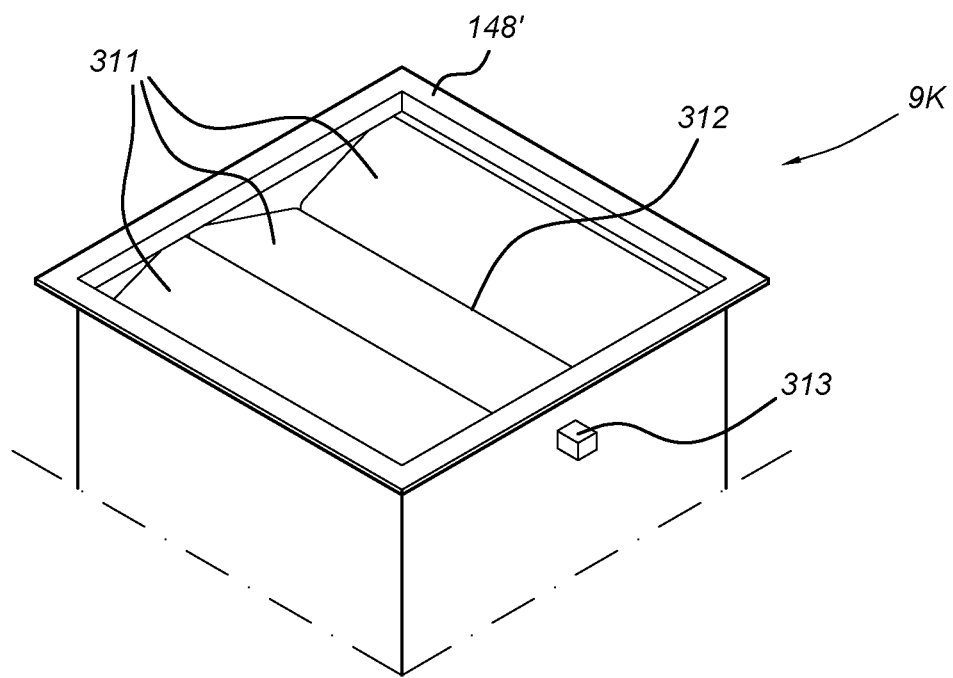
FIG. 14B shows a perspective top/side view of the cyclone separation system 148, comprised by the insects transport device of the invention, showing laminar slats in the top portion 148' of the system 148.
Figure 14C:
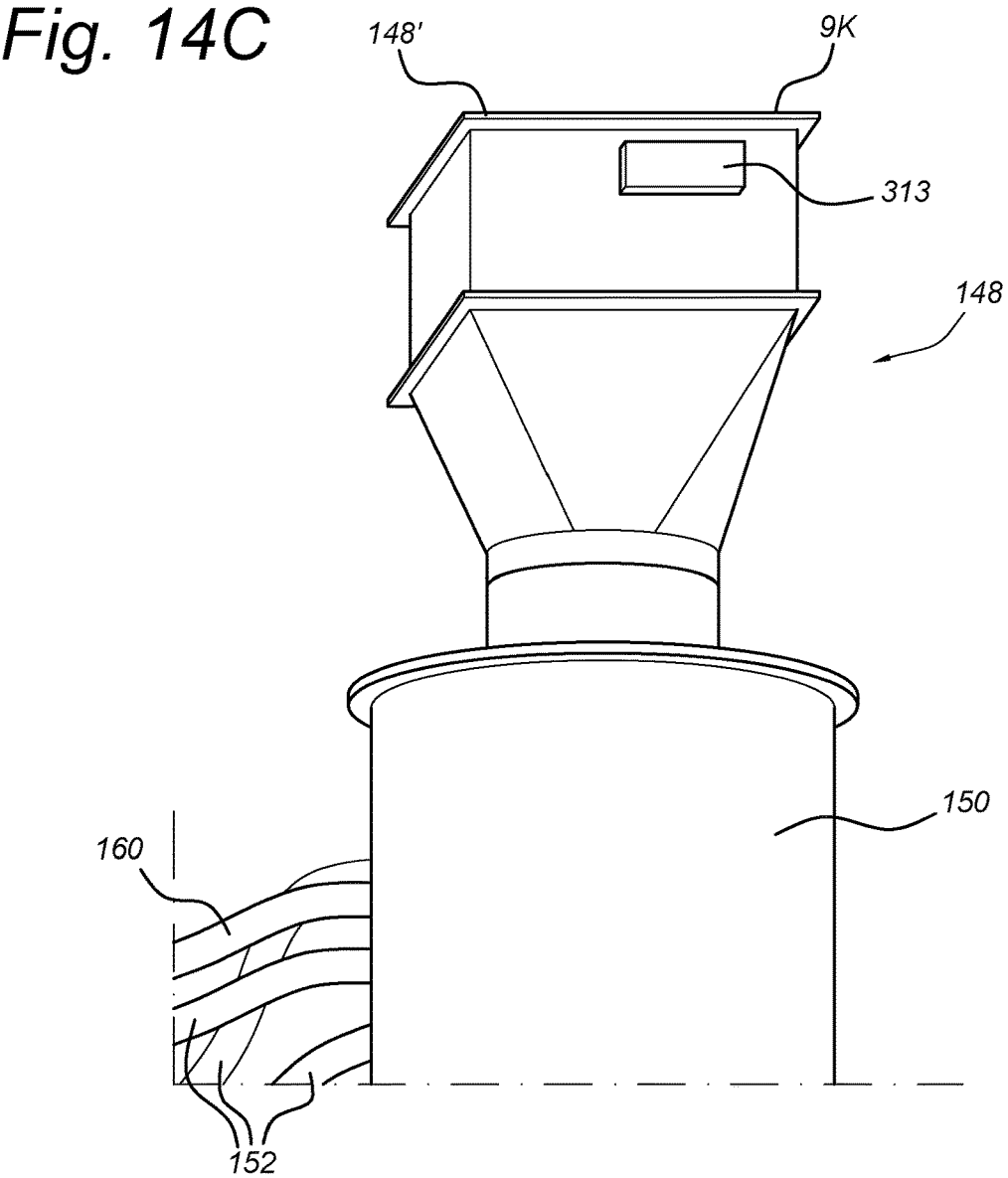
FIG. 14C shows a side view of part of the cyclone separation system 148.

Turning to FIG. 14A, the top view of the cyclone separation system 148 now provided with an air exit 9K, is shown, the cyclone separation system comprised by the insects transport device of the invention, wherein the top view of the air exit 9K shows laminar slats 311 that are openable under control of a control unit 313. The slats are pivotally connected to upper portion 148' of the cyclone separation system, through pivots 312. Operating the slats 311 provides the possibility to adjust and for example temporarily increase the air pressure inside the cyclone separation system independently of the contribution to the air pressure by the transport air entering the cyclone separation system from the live insects discharge member, by partly or wholly shutting the laminar slats. FIG. 14B shows a perspective top/side view of the cyclone separation system 148 with the air exit 9K, comprised by the insects transport device of the invention, showing laminar slats in the top portion 148' of the system 148 and FIG. 14C shows a side view of part of the cyclone separation system 148 with the optional air exit 9K. By providing the cyclone separation system with these laminar slats, the operation of the insects transport device in so far the laminar flow of air is considered, is independent of the operation of the insects transport device in so far the batch wise dosing of live insects by use of the cyclone separation system is considered. Thus, air pressure and air flow velocity with regard to the laminar air flow inside the casing 5, 105, is controllable and adjustable without influencing the live insects dosing operation of the cyclone separation system part of the insects transport device.

Figure 5:
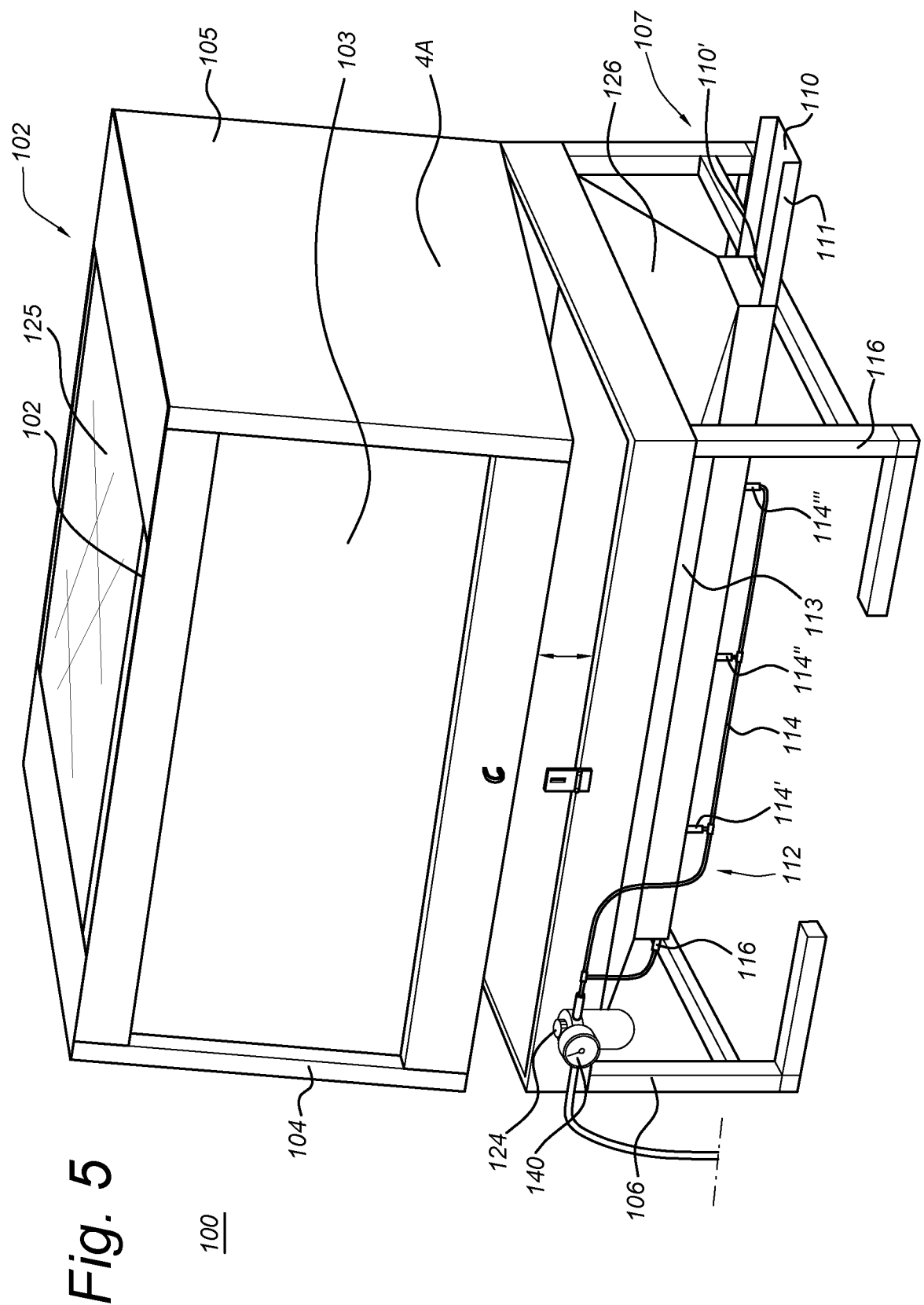
FIG. 5 displays an overview of another embodiment of the invention, showing an insects transport device 100 comprising a live insects receiving portion that is built up by a gas guiding unit 112 comprising side walls 113 tilted at an obtuse angle relative to the top surface of the gas guiding members. The insects transport device of the embodiment comprises a thermally insulated casing 105, said casing having a top side 102 optionally made at least in part from a transparent material 125 such as a plate made of glass.
Figure 6:
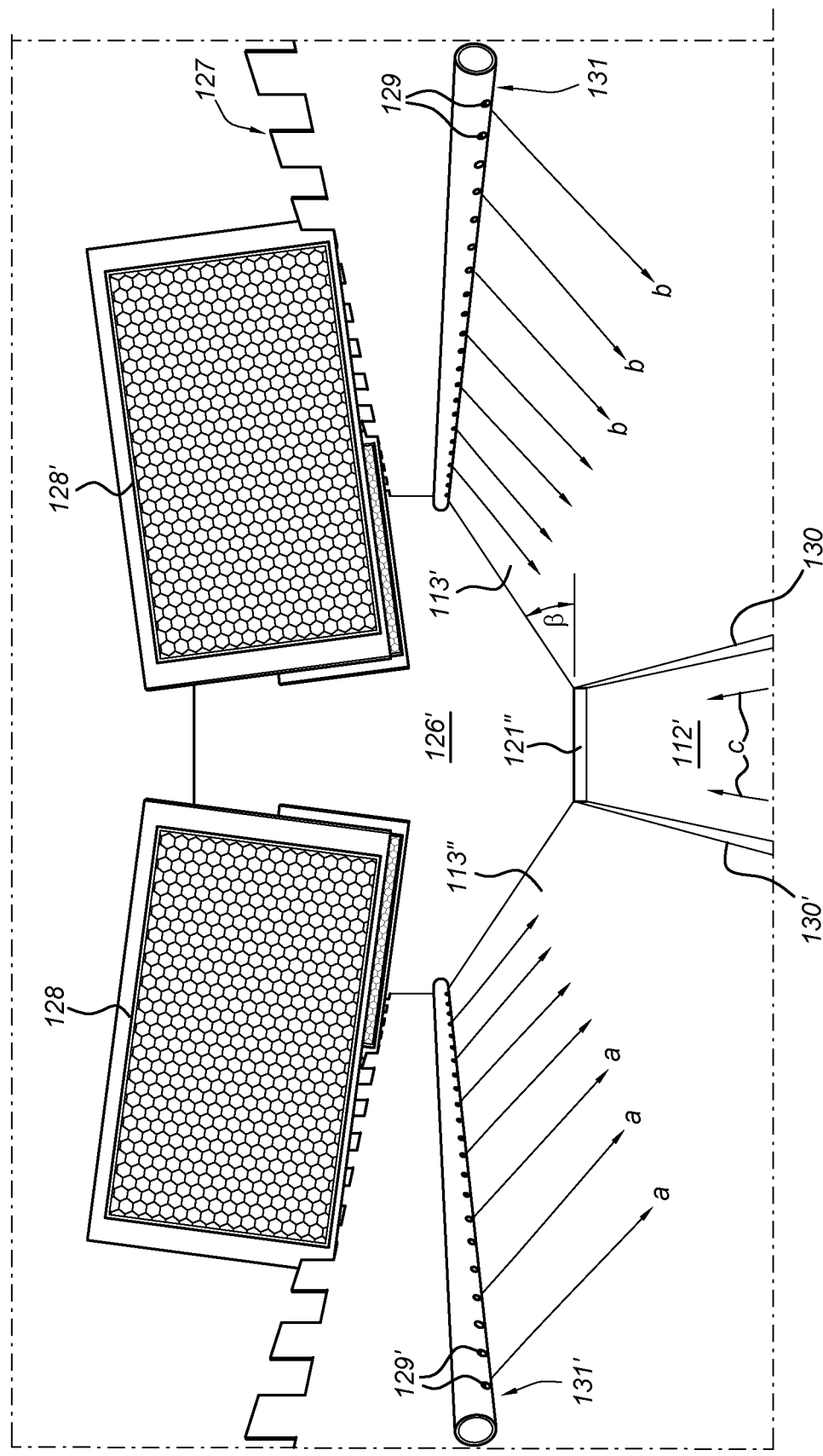
FIG. 6 displays a part of a live insects receiving portion of an insects transport device 100 of the invention, the live insects receiving portion being built up by a gas guiding unit 112' comprising side walls 113' and 113" tilted at an obtuse angle relative to the top surface of the gas guiding members. Further displayed are the proximal end 121" of the live insects guiding unit 112' and the further gas discharge members 131 and 131' located at the top side of the side walls, and the feeder arrangement 127 located above the live insects receiving portion of the top surface of the gas guiding unit.
Figure 15A:
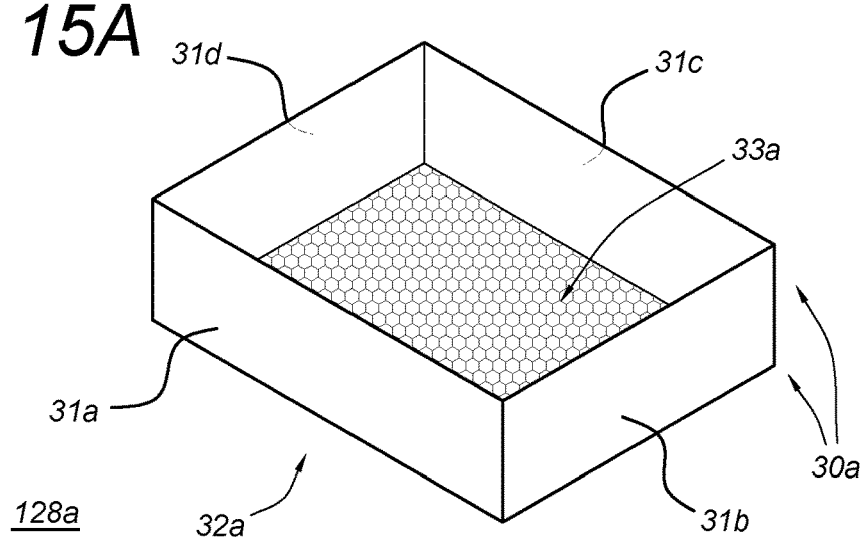
FIG. 15A shows a reservoir 128a, consisting of a cage for live insects such as mite, the cage comprising side walls and a bottom floor comprising openings for passage of live insects.
Figure 15B:
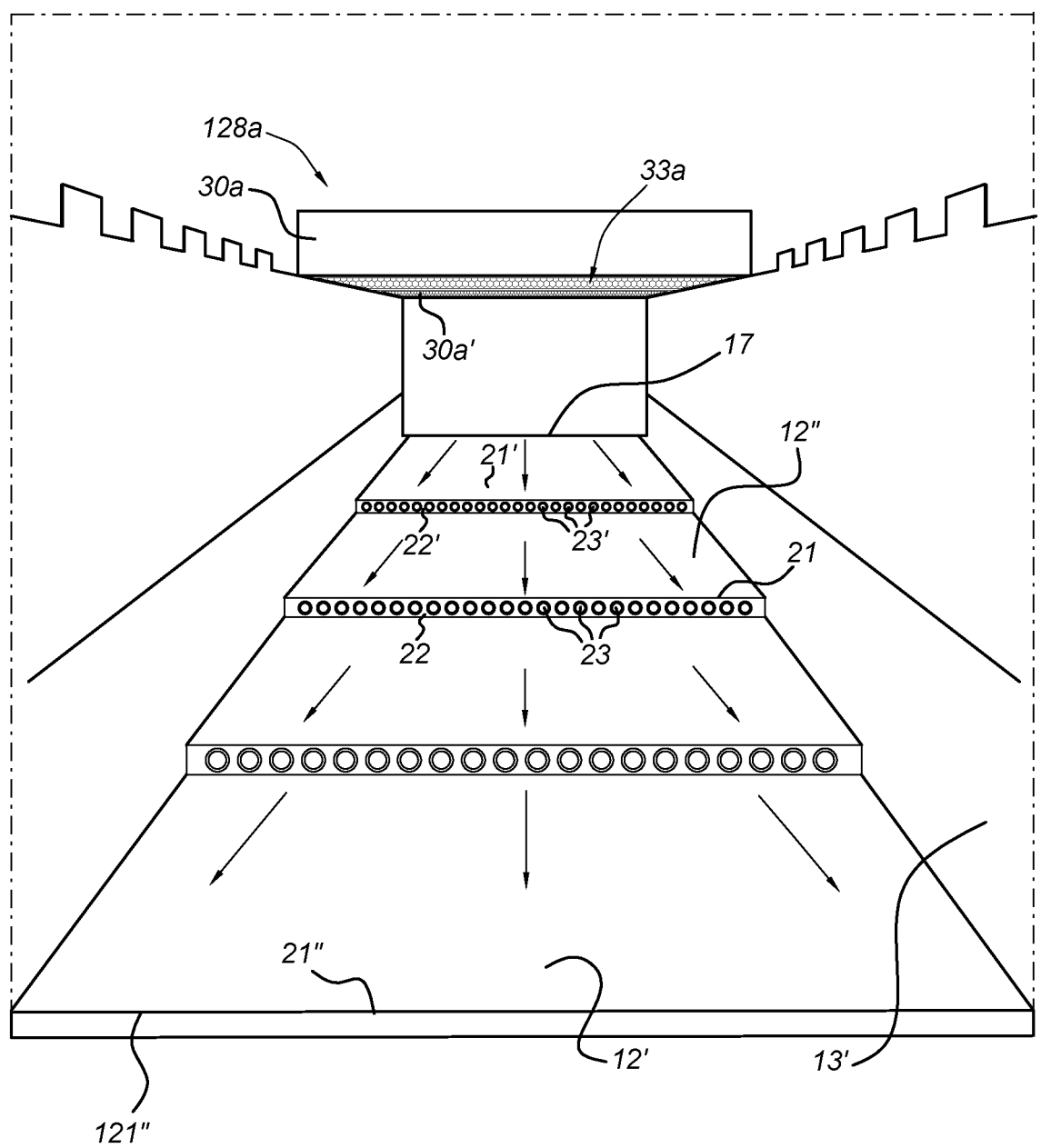
FIG. 15B displays an inside view of an insects transport device of the invention. Shown are longitudinal gas transport members 12', 12" which are connected imbricatedly at posit
Figure 15C:
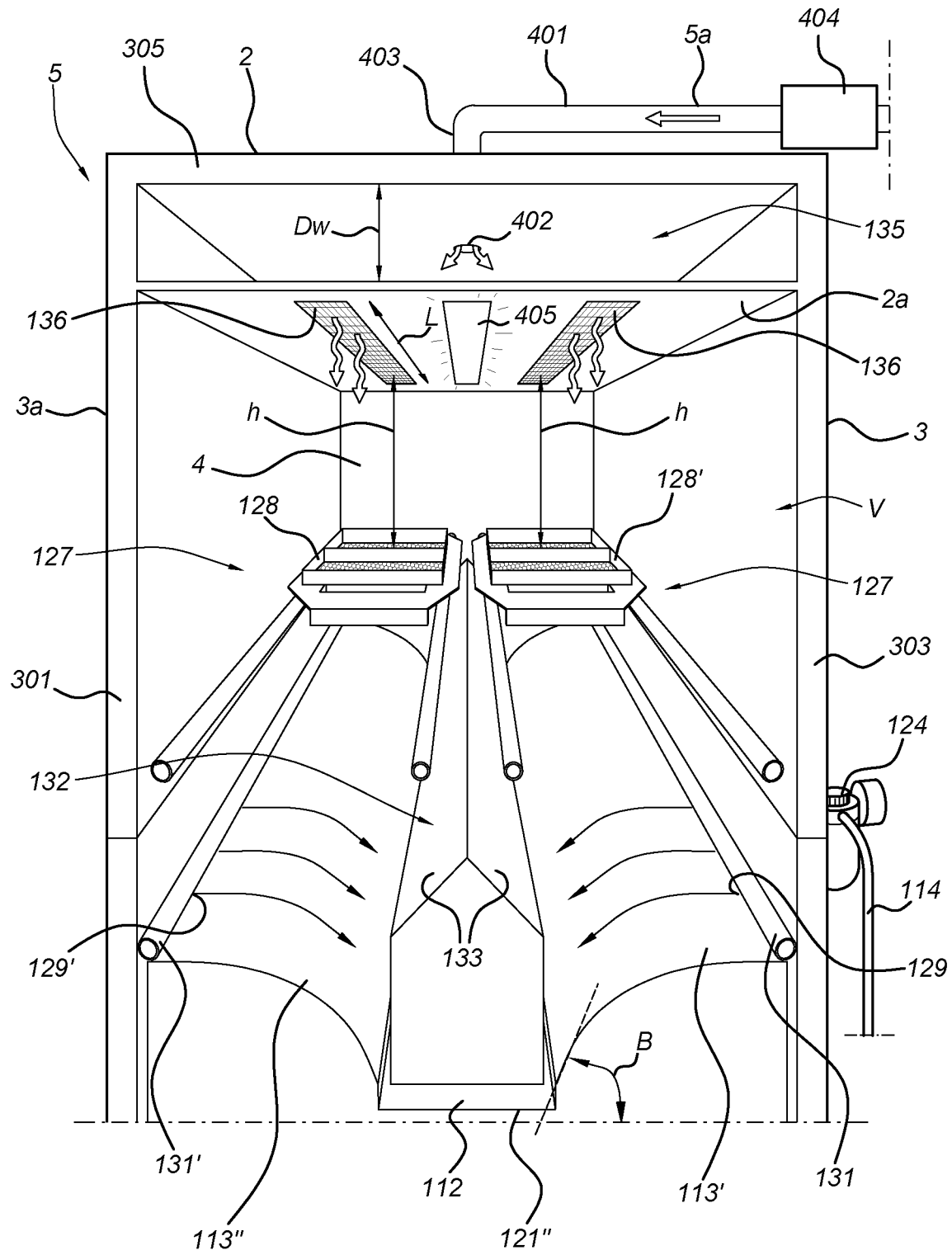
Figure 15D:
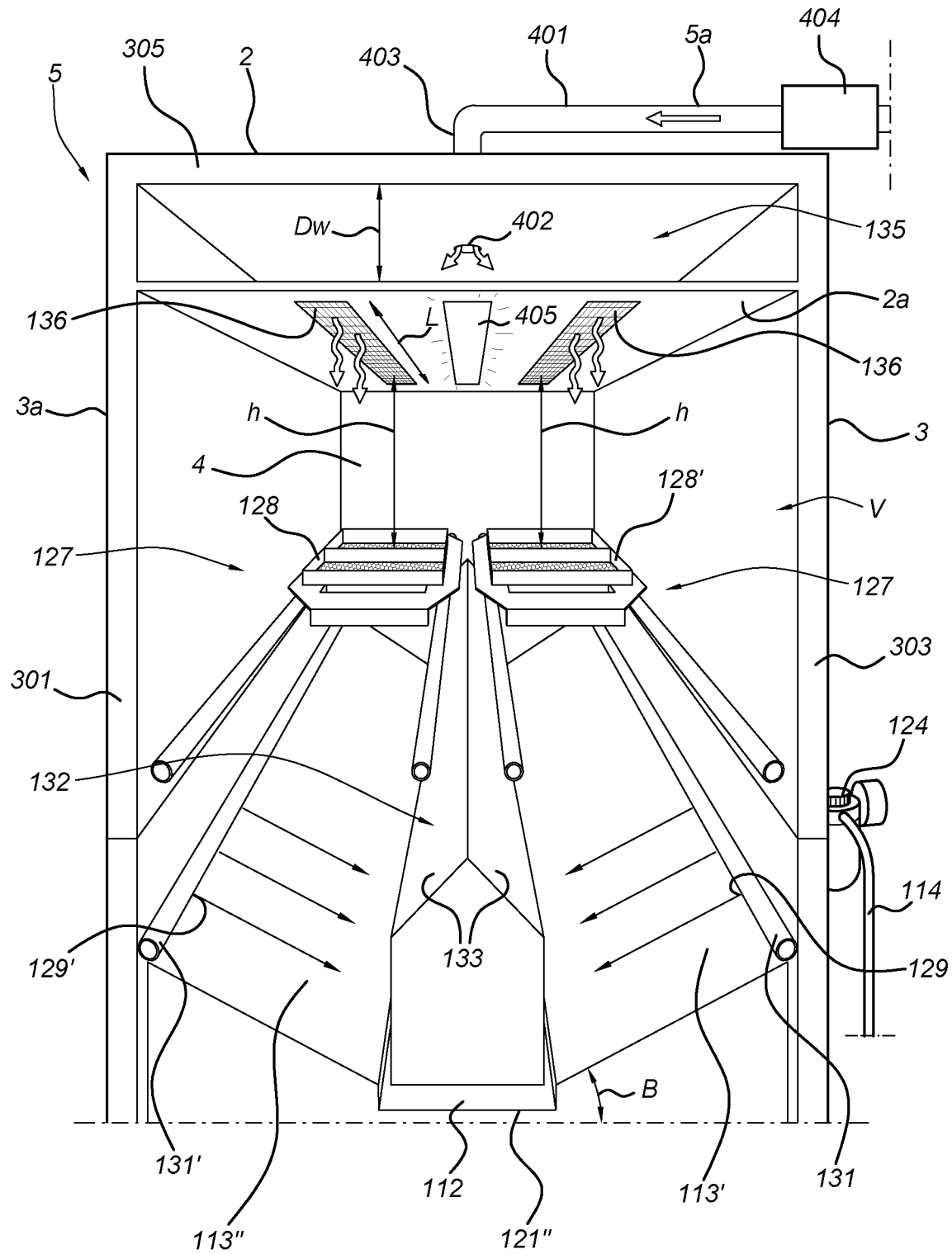

The live insects device of the invention provides for efficient and accurate and constant dosing of live insects such as insect eggs, embryo, neonate larvae, larvae, prepupae, pupae, imago, adult insect, for example fly neonate larvae such as black soldier fly larvae 1 second-1 day of age, preferably 10 seconds-2 hours of age, or for example imago such as mites. For applying the insects transport device 1, 100 for counting, dosing such as batch wise dosing, of e.g. imago such as mites, a reservoir 128*a* adapted to the delivery of such mites to the laminar air flow, is provided. FIG. 15A shows a reservoir 128*a*, consisting of a cage 128*a* for live insects such as mite, the cage 128*a* comprising side walls 31*a*-31*d* and a bottom floor 32*a* comprising openings 33*a* for passage of live insects. The openings in the bottom floor 32*a* of the cage 128*a* are typically provides as through holes 33*a*, slits 33*a*, a mesh 33*a*, a sieve 33*a*, etc., wherein the openings have dimensions suitable for passage of live insects at the desired stage and age of their development, such as adult mites. FIG. 15B displays an inside view of an insects transport device 1, 100 of the invention. Shown are longitudinal gas transport members 12', 12" which are connected imbricatedly at positions 21, 22 and 21', 22'. Where two consecutive gas transport members are coupled imbricatedly, a gas discharge member (See 20, 20' in FIGS. 2 and 114', 114", 114''' in FIG. 5) is positioned at the location where said gas transport members overlap, said gas discharge member provided with openings 23, 23' for discharging gas. The insects transport device 1, 100 comprises a reservoir 128a, i.e. a cage 128a for keeping mites, the cage 128a comprising side walls 31a-31d and a bottom floor 32a comprising openings 33a for passage of live insects. The cage 128a is supported by support member 30a, i.e. a frame 30a for receiving the cage 128a. A further frame, 30a' for receiving a further cage (reservoir) 128a' is also displayed. FIG. 15C and FIG. 15D show a thermally insulated casing 5 with side walls 3, 3a and with top wall 2, of a(n) (live) insects transport device 100 according to two embodiments of the present invention, the insects transport device comprising a reservoir 128a, the reservoir being a cage 128a for live insects, such as imago, such as mites, the cage 128a, 128a' comprising side walls 31a-d and a bottom floor 32a comprising openings 33a for passage of live insects, the casing 5 comprising a secondary top wall 2a defining a volume 135. FIG. 15C displays an embodiment of the insects transport device 100 of the invention, wherein the live insects receiving portion further comprises convex side walls 113', 113" located along longitudinal sides of the at least one longitudinal gas guiding member 12', 12", 12''' (see also FIG. 8), wherein each convex side wall 113', 113" has a top side and a bottom side and a smooth convex surface 115 arranged between the top and bottom side, the bottom side being connected to a longitudinal side of the at least one gas guiding member 12', 12", 12'''. FIG. 15D displays an embodiment of the insects transport device 100 of the invention, wherein the live insects receiving portion comprises flat and straight side walls 113', 113" located along longitudinal sides of the at least one longitudinal gas guiding member 12', 12", 12''' (see also FIG. 7), wherein flat side wall 113', 113" has a top side and a bottom side and a smooth surface 115 arranged between the top and bottom side, the bottom side being connected to a longitudinal side of the at least one gas guiding member 12', 12", 12'''. In FIG. 15D, the live insects receiving portion is shown and is built up by a gas guiding unit 112 comprising side walls 113' and 113", e.g. flat side walls 113', 113", tilted at an obtuse angle relative to the top surface of the gas guiding members.

Figure 16A:
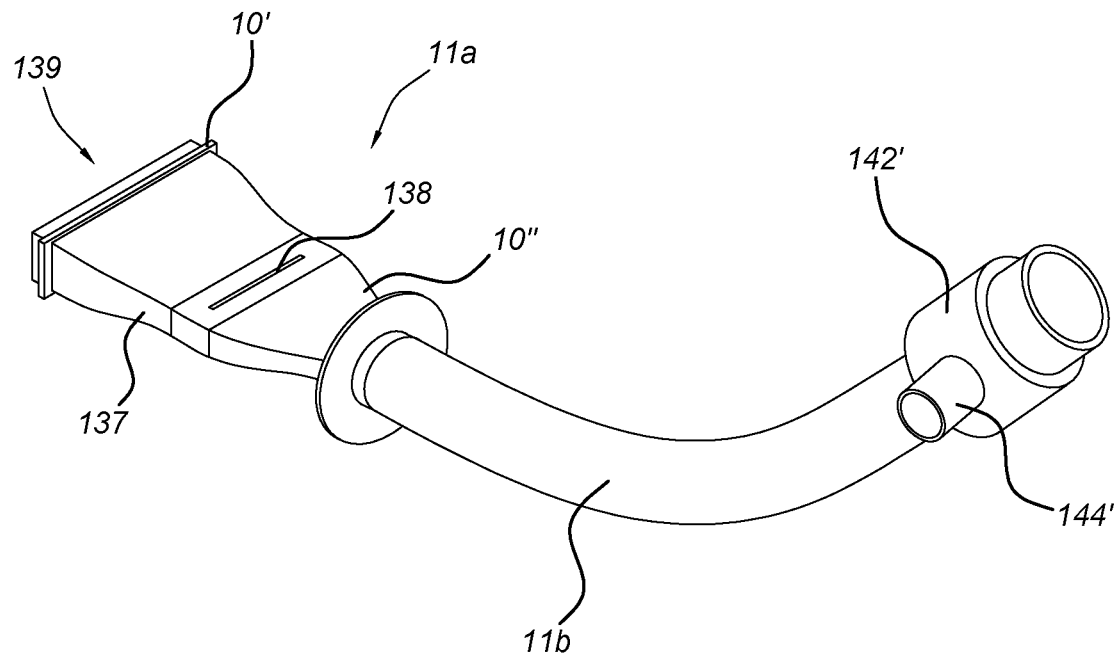
FIG. 16D shows a schematic view of an insects transport device 100 further provided with a cyclone separation system 148 fluidly connected to the live insect discharge member 11a via tubing 11b and air amplifier unit 142', according to an embodiment of the present invention.
Figure 16B:
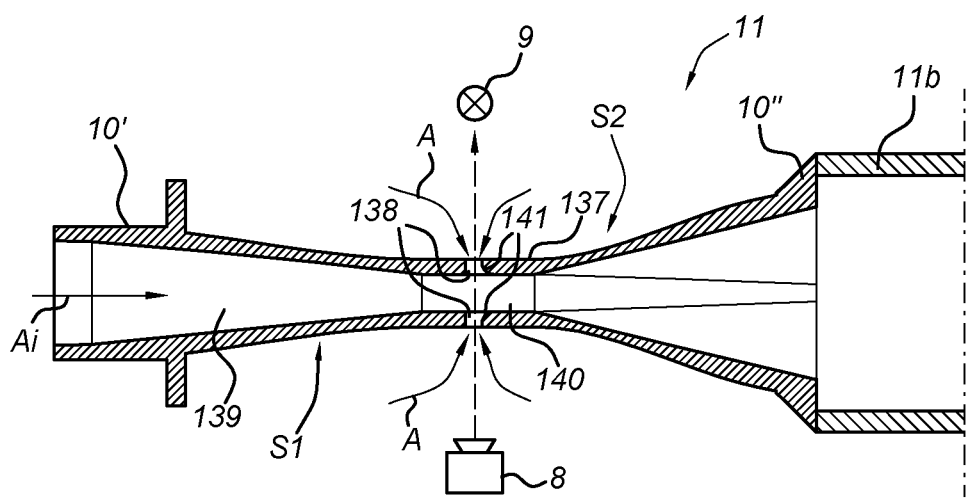
Figure 16C:
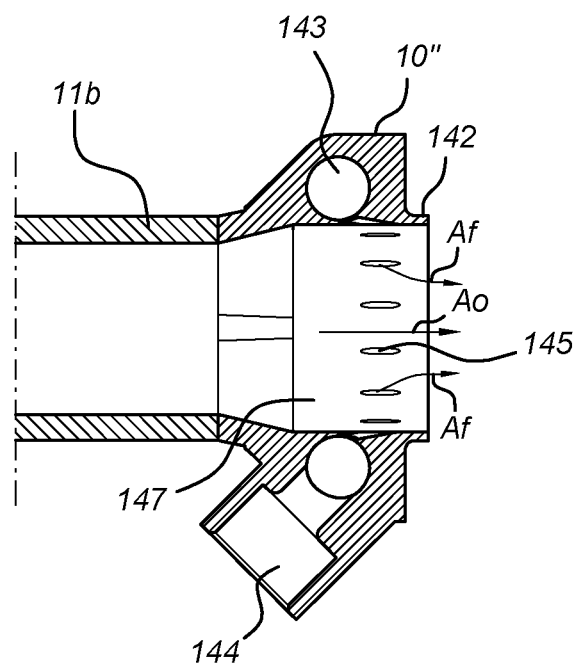

FIG. 16A displays an insect discharge member 11a coupled to a tube 11b, the tube 11b connected to an air amplifier unit 142'. FIG. 16B displays a cross-sectional side view of the insect discharge member 11a connected to tube 11b displayed in FIG. 16A. FIG. 16C shows a cross-sectional side view of air amplifier unit 142' displayed in FIG. 16A, fluidly connected to tube 11b, which is connected at its proximal end to the insect discharge member 11a as displayed in FIG. 16B. FIG. 16D shows a schematic view of an insects transport device 100 further provided with a cyclone separation system 148 fluidly connected to the live insect discharge member 11a via tubing 11b and air amplifier unit 142', according to an embodiment of the present invention.

Figure 22:
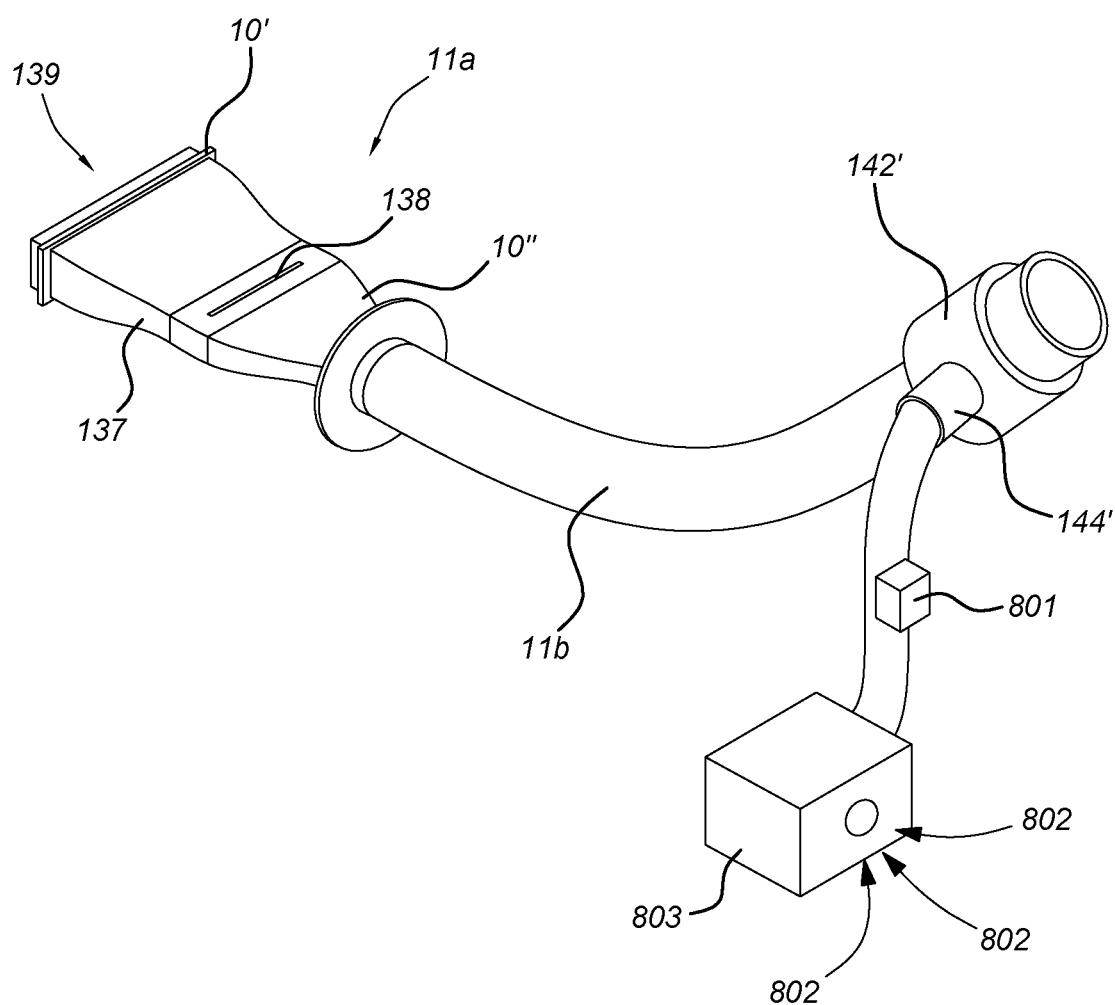
FIG. 22 displays an insect discharge member 11a coupled to a tube 11b, the tube 11b connected to an air amplifier unit 142' comprising a driver (a fan) 803, an air inlet for air 802, a sensor 801 for sensing air humidity and temperature.

FIG. 22 shows an insect discharge member 11a coupled to a tube 11b, the tube 11b connected to an air amplifier unit 142', similar to the insects discharge member 11a as outlined in FIG. 16A, though with the additional driver 803 such as a fan 803, for driving gas such as ambient air 802 towards connector 144' which connects the fan with air amplifier 142'. Sensor 801 senses and/or controls the temperature and air humidity of the air 802 driven by driver 803 towards the air amplifier 142' and into the cyclone separation system 148.

Figure 23:
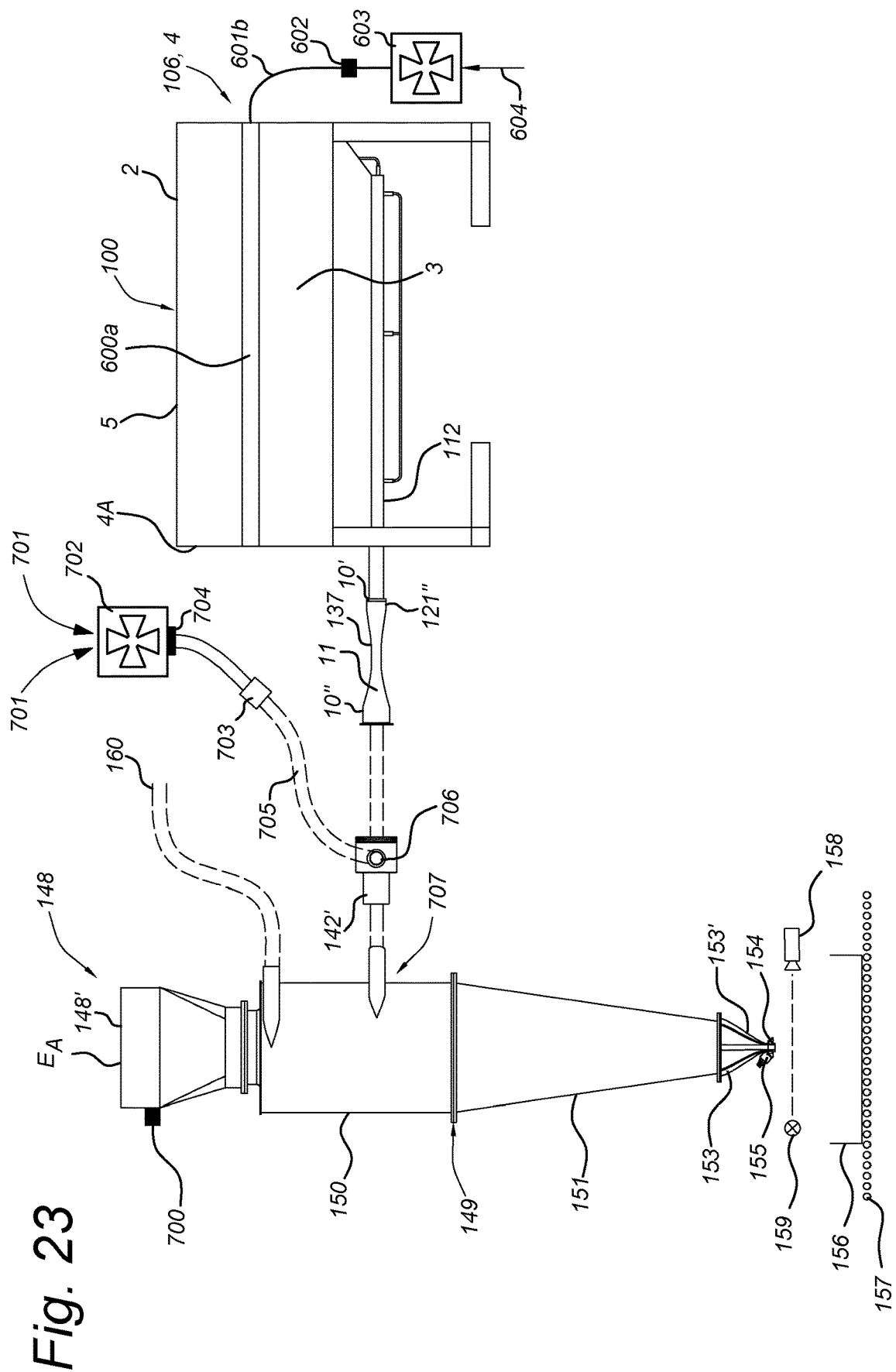
FIG. 23 shows a schematic view of an insects transport device 100 further provided with a cyclone separation system 148 connected to the live insect discharge member 11, according to an embodiment of the present invention, wherein the opening 707 in top chamber part 150 of the cyclone separation system 148 is substantially at the same height, relative to the horizontal, as the proximal end 121" of gas guiding unit 112. The cyclone separation system 148 is further optionally provided with sensor 700 for sensing air humidity and temperature of air inside the cyclone separation system 148, according to an embodiment of the present invention; and wherein the air amplifier 142' and the insect discharge member 11, 11', 11a of FIG. 20 and FIG. 22 are incorporated in the connection between the insects transport device 100 and the cyclone separation system 148, therewith forming a fluid connection.

Similar to the cyclone separation system 148 of the embodiment displayed in FIG. 16D, FIG. 23 shows a schematic view of a cyclone separation system 148 further provided with an insects transport device 100 fluidly connected to the live insect discharge member 11a via tubing 11b and air amplifier unit 142', according to an embodiment of the present invention. The embodiment of FIG. 23 differs from the embodiment in FIG. 16D in that the cyclone portion encompassing top cyclone chamber 150 comprising connector 707 for connecting insects transport device 100 to the cyclone chamber 150 which is at the same height, relative to the horizontal, as the proximal end 121" of the gas guiding unit 112. Herewith, living insects such as mites and black soldier fly larvae are transported through essentially horizontally oriented tubing or pipes, preferably rigid pipes from the insects transport device 100 portion to and into upper cyclone chamber 150 of the cyclone separation system 148. This way, the risk and chance for insects hitting internal side walls of tubing, pipes, etc. is further lowered. Moreover, with straight tubing and pipes, risk for air turbulence inside the tubing and pipes is reduced or even absent such that air borne transported living insects are prevented from being blocked, blown to inner walls, accumulation in certain spots of the system, etc.

Figure 17A:
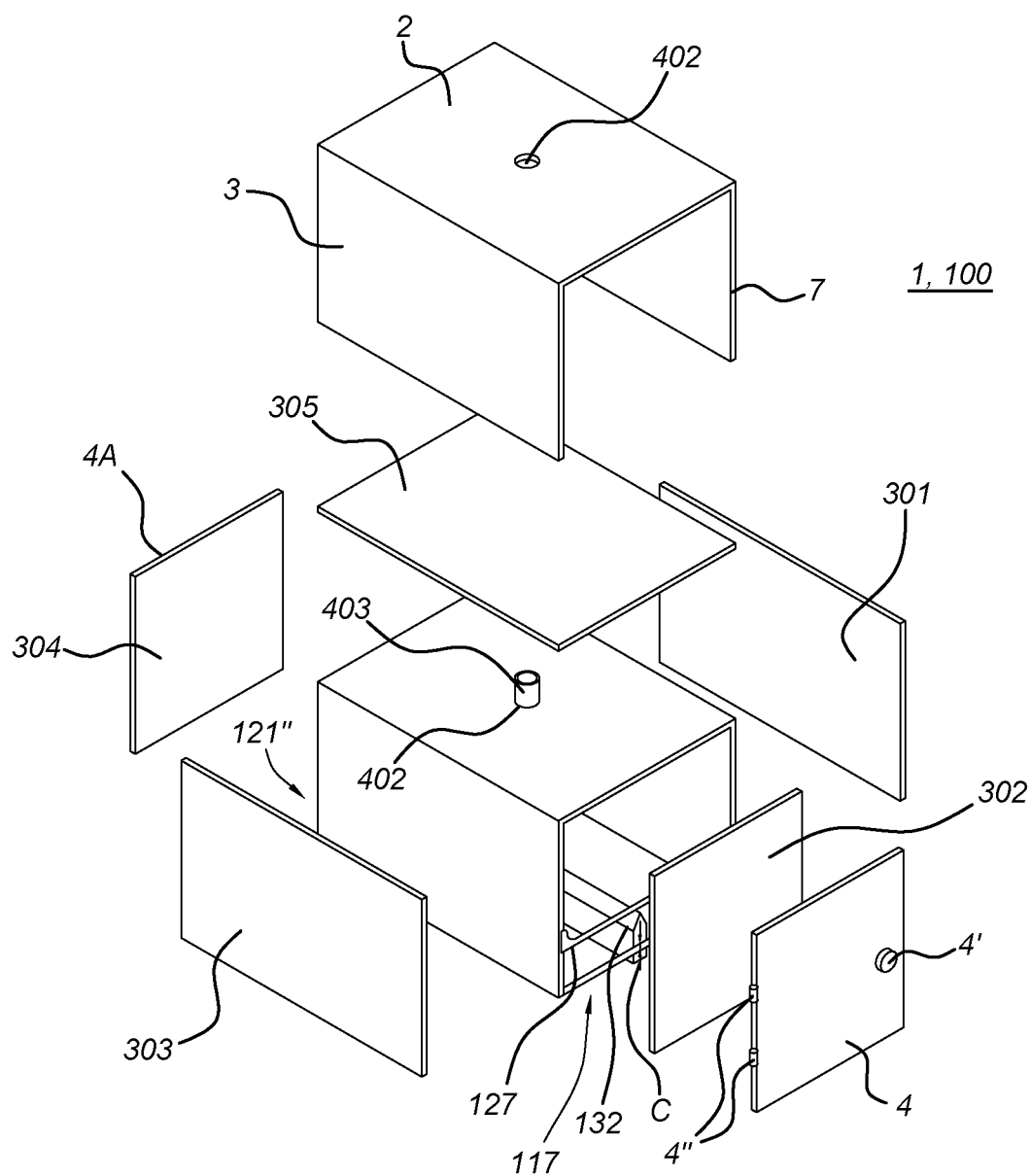
FIG. 17A displays an exploded view of an insects transport device 1, 100, showing the side walls and top wall of the casing 5, 105, said side walls and top wall provided with a layer of thermally insulating material 301-305, wherein the side wall 4 is an openable door 4.
Figure 17B:
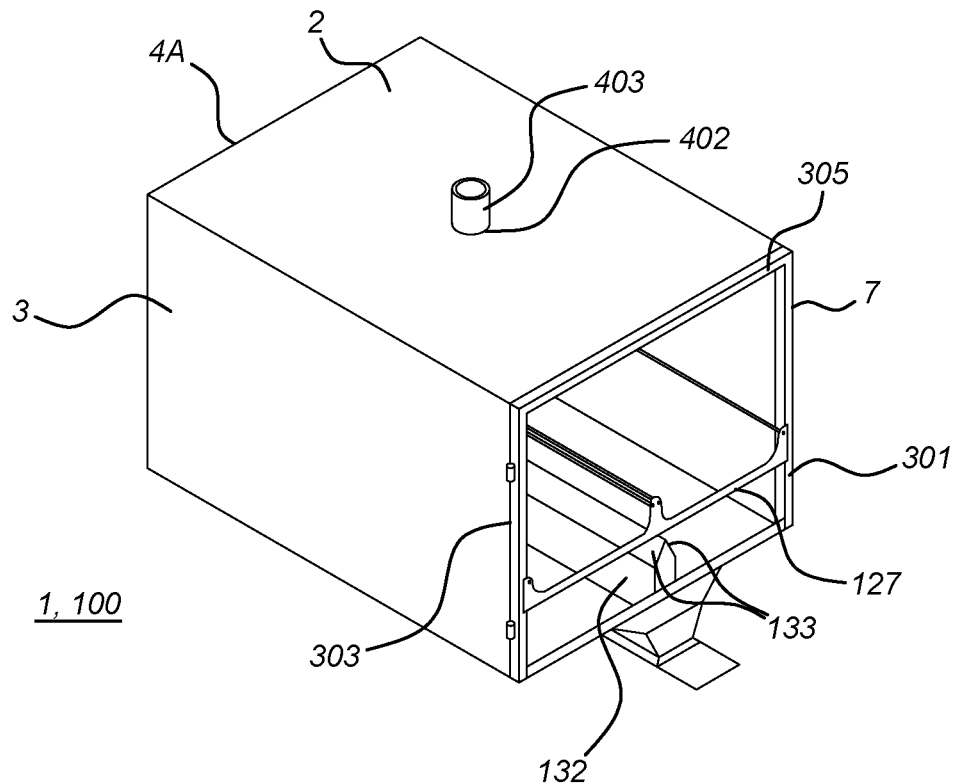
FIG. 17B displays an insects transport device 1, 100 provided with casing 5, 105, wherein said casing comprises thermally insulated side walls and a thermally insulated top wall. For clarity the front side wall 4 is not shown.
Figure 17C:
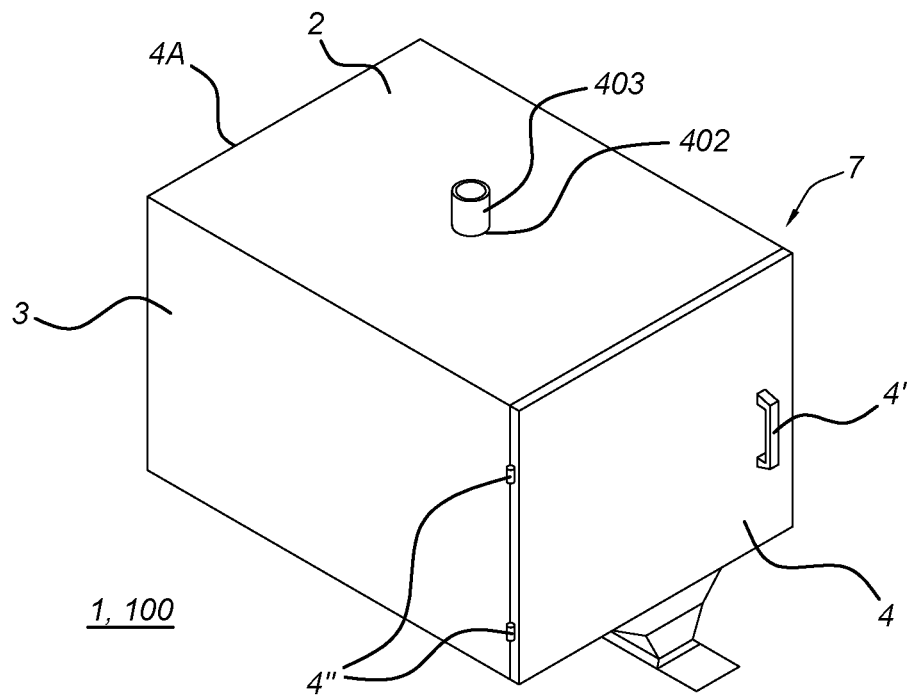
FIG. 17C displays an insects transport device 1, 100 provided with casing 5, 105, wherein said casing comprises thermally insulated side walls and a thermally insulated top wall, according to an embodiment of the invention.

FIG. 17A displays an exploded view of an insects transport device 1, 100, showing the side walls 3, 4, 4A, 7 and top wall 2 of the casing 5, 105, said side walls 3, 4, 4A, 7 and top wall 2a provided with a layer 303, 302, 304, 301, 305 of thermally insulating material respectively, wherein the side wall 4 is an openable door 4 provided with a knob or grip 4' and pivots 4". FIG. 17B displays an insects transport device 1, 100 provided with casing 5, 105, wherein said casing comprises thermally insulated side walls 3, 4, 4A, 7 and an thermally insulated top wall 2. For clarity the front side wall 4 is not shown. For side walls 3, 3a and 7 and for top wall 2, the layers of thermally insulating material 301, 303 and 305 are visualized. The feeder arrangement inside the casing is visible, as well as the cover member 132 inside the casing. In the top wall 2 of the casing, through hole 402 is visualized, together with connector 403, which is part of the air feed channel 5a (see FIG. 10 and FIGS. 15C and D). FIG. 17C displays an insects transport device 1, 100 provided with casing 5, 105, wherein said casing comprises thermally insulated side walls 2, 3, 3a, 4, 4A and a thermally insulated top wall 2, according to an embodiment of the invention. Side wall 4 is an openable door 4 provided with a grip 4' and pivots 4". The top wall 2 of the casing comprised by the insects transport device comprises opening 402 for receiving the connector portion 403 of the air feed channel 5a.

The invention claimed is:
1. An insects transport device comprising:
a gas guiding unit comprising a distal end and a proximal end, and at least one longitudinal gas guiding member comprising a distal end and a proximal end, wherein the distal end of the gas guiding member is arranged at the distal end of the gas guiding unit and wherein the proximal end of the gas guiding member is directed toward the proximal end of the gas guiding unit,
wherein the at least one gas guiding member further comprises a smooth top surface, said smooth top surface being free of elements from a group comprising ridges, protrusions and recesses, and extending from the distal end to the proximal end of the gas guiding member, the smooth top surface comprising a live insect larvae receiving portion between the distal end and proximal end of the at least one gas guiding member;

a first gas discharge member located at the distal end of the gas guiding unit and being configured to connect to a source of gas, wherein the first gas discharge member is further configured to provide a first laminar flow of gas over the smooth top surface of the at least one gas guiding member from the distal end to the proximal end thereof during operation of the transport device; and wherein the transport device further comprises a feeder arrangement located above the live insect larvae receiving portion of the smooth top surface of the gas guiding unit, wherein the feeder arrangement is configured to receive at least one ovisite or tray, with at least one open side, for releasing live insect larvae directly above the live insect larvae receiving portion, wherein the insects transport device further comprises a casing covering the gas guiding unit and the feeder arrangement, and wherein the casing is provided with a thermally insulated top wall and side walls.

2. The insects transport device according to claim 1, wherein the first gas discharge member is further configured to provide a continuously flowing first laminar flow of gas over the smooth top surface of the at least one gas guiding member from the distal end to the proximal end thereof during operation of the transport device.

3. The insects transport device according to claim 1, wherein the feeder arrangement is configured to receive the at least one ovisite or tray for releasing live insects by gravity-driven free fall through gas medium present in the insect transport device, above the insects receiving portion, and therewith in the first laminar flow of gas, such that during operation of the insects transport device insects freely flow from the at least one ovisite or tray into and with the first laminar flow of gas without contacting a surface of the gas guiding member(s).

4. The insects transport device according to claim 1, wherein said transport device comprises at least two imbricatedly coupled longitudinal gas guiding members, the gas guiding members being imbricatedly coupled with a coupler located at the proximal end of a first gas guiding member and the distal end of a second gas guiding member.

5. The insects transport device according to claim 4, wherein the coupler imbricatedly coupling the at least two gas guiding members is provided with a further gas discharge member comprising a connector configured to connect each further gas discharge member to a source of gas, and wherein the further gas discharge member(s) is/are configured to reinforce from below the first laminar flow of gas over the smooth top surface of the at least one gas guiding member from the distal end to the proximal end of the gas guiding unit during operation of the transport device.

6. The insects transport device according to claim 1, wherein the gas is temperature-controlled gas and/or wherein the gas is a relative humidity-controlled gas.

7. The insects transport device according to claim 1, further comprising a live insect discharge member comprising a flat surface with a first end and a second end, the discharge member coupled with its first end to the proximal end of the gas guiding unit.

8. The insects transport device according to claim 7, further comprising a live insects counting device for counting live insects in the first laminar flow exiting the insect transport device at the proximal end of the live insect discharge unit, wherein the counting device is a high-speed camera.

9. The insects transport device according to claim 1, wherein the at least one ovisite or tray for live insects is an insect egg collection interface or an insect egg holder or wherein the ovisite or tray for live insects is a live insect cage provided with a perforated bottom floor.

10. The insect transport device according to claim 1, wherein the casing comprises a side wall at the distal end of the gas guiding unit, said side wall is openable.

11. The insects transport device according to claim 1, wherein the live insects receiving portion further comprises convex side walls located along longitudinal sides of the at least one longitudinal gas guiding member, wherein each convex side wall has a top side and a bottom side and a smooth convex surface arranged between the top and bottom side, the bottom side being connected to a longitudinal side of the at least one gas guiding member, and wherein the top side of each convex side wall is provided with a second gas discharge member comprising a connector configured to connect the second gas discharge member to a source of gas for providing a second laminar flow of gas over the surface of the convex side wall from the top side thereof to the at least one gas guiding member during operation of the insect larvae transport device.

12. The insects transport device according to claim 1, wherein the live insects receiving portion further comprises flat side walls with a flat surface, located along longitudinal sides of the at least one longitudinal gas guiding member, wherein each flat side wall has a top side and a bottom side and a smooth flat surface arranged between the top and bottom side, the bottom side being connected to a longitudinal side of the at least one gas guiding member, and wherein the top side of each flat side wall is provided with a second gas discharge member comprising a connector configured to connect the second gas discharge member to a source of gas for providing a second laminar flow of gas over the surface of the flat side wall from the top side thereof to the at least one gas guiding member during operation of the insect larvae transport device.

13. The insects transport device according to claim 11, further comprising a cover member extending along and above the at least one gas guiding member at a clearance distance with respect thereto.

14. The insects transport device according to claim 13, wherein the cover member comprises a plurality of cover side walls, wherein each cover side wall extends in upward and longitudinal/lengthwise direction along one of the side walls.

15. The insects transport device according to claim 13, wherein the cover member further comprises a sloped roof.

16. The insects transport device according to claim 11, comprising flat side walls or arched convex side walls arranged along the gas guiding unit and air slits and arranged along the top side of the flat side walls or the top side of the arched convex side walls.

17. The insects transport device according to claim 1, wherein the casing covering the gas guiding unit and the feeder arrangement comprises a top wall and side walls defining a closed inner volume in which the at least one ovisite or tray reservoir is arranged, and wherein the insects transport device comprises an air feed channel, wherein said air feed channel comprises a tube and a connector connected to the top wall through an opening, further comprising gas temperature controller and absolute air humidity control unit, configured to provide air of a controllable and desired temperature and/or controllable and desired relative humidity to the inner volume of the casing.

18. The insects transport device according to claim 17, wherein the casing further comprises a secondary top wall arranged below the top wall at a wall distance therefrom defining a cavity space between the top wall and the secondary top wall, wherein the secondary top wall further comprises one or more slits fluidly connecting the cavity space and the inner volume of the casing.

19. The insects transport device according to claim 1, wherein ab inner side of the top wall of the casing is provided with a light source and/or a heater positioned above the feeder arrangement, such that the at least one ovisite or tray positioned in the feeder arrangement is irradiable with light by the light source from above the at least one ovisite or tray and/or heatable with the heater from above the at least one ovisite or tray during operation of the insects transport device.

20. The insects transport device according to claim 1, further comprising a cyclone separation system, wherein the second end of the live insect discharge member is in fluid connection with the cyclone separation system comprising a main cyclone chamber having a top chamber part and a conical shaped bottom chamber part, wherein the top chamber part is connected to one or more intake channels each of which is arranged for fluid connection to the second end of the live insect discharge member of an insects transport device, and
  wherein the bottom chamber part is connected to a discharge nozzle comprising a discharge end having a main discharge conduit for discharging live insects from the cyclone separation system, and
  wherein the discharge end comprises an air injection member for connection to a secondary air source and wherein the air injection member is configured to inject air back into the discharge nozzle.

* * * * *